US011261494B2

(12) United States Patent
Lo et al.

(10) Patent No.: US 11,261,494 B2
(45) Date of Patent: Mar. 1, 2022

(54) METHOD OF MEASURING A FRACTIONAL CONCENTRATION OF TUMOR DNA

(71) Applicant: The Chinese University of Hong Kong, Shatin (CN)

(72) Inventors: Yuk-Ming Dennis Lo, Homantin (CN); Rossa Wai Kwun Chiu, Shatin (CN); Kwan Chee Chan, Mei Foo Sun Chuen (CN); Peiyong Jiang, Shatin (CN)

(73) Assignee: The Chinese University of Hong Kong, Shatin (HK)

( * ) Notice: Subject to any disclaimer, the term of this patent is extended or adjusted under 35 U.S.C. 154(b) by 441 days.

(21) Appl. No.: 13/801,748

(22) Filed: Mar. 13, 2013

(65) Prior Publication Data

US 2014/0100121 A1  Apr. 10, 2014

Related U.S. Application Data

(60) Provisional application No. 61/662,878, filed on Jun. 21, 2012, provisional application No. 61/682,725, filed on Aug. 13, 2012, provisional application No. 61/695,795, filed on Aug. 31, 2012, provisional application No. 61/711,172, filed on Oct. 8, 2012.

(51) Int. Cl.
*C12Q 1/6886* (2018.01)
*G16B 20/00* (2019.01)
*G16B 30/00* (2019.01)
*G16B 20/20* (2019.01)
*G16B 30/10* (2019.01)
*B01J 19/00* (2006.01)
*C12N 15/10* (2006.01)
*C12Q 1/6806* (2018.01)
*C12Q 1/6855* (2018.01)
*G01N 33/574* (2006.01)

(52) U.S. Cl.
CPC ........ *C12Q 1/6886* (2013.01); *B01J 19/0046* (2013.01); *C12N 15/1065* (2013.01); *C12Q 1/6806* (2013.01); *C12Q 1/6855* (2013.01); *G01N 33/574* (2013.01); *G16B 20/00* (2019.02); *G16B 20/20* (2019.02); *G16B 30/00* (2019.02); *G16B 30/10* (2019.02); *C12Q 2525/191* (2013.01); *C12Q 2535/122* (2013.01); *C12Q 2600/106* (2013.01); *C12Q 2600/112* (2013.01); *C12Q 2600/166* (2013.01)

(58) Field of Classification Search
None
See application file for complete search history.

(56) References Cited

U.S. PATENT DOCUMENTS

| 7,704,687 | B2 | 4/2010 | Wang et al. |
| 8,741,811 | B2 | 6/2014 | Lo et al. |
| 2003/0219765 | A1 | 11/2003 | Costa |
| 2005/0164241 | A1 | 7/2005 | Hahn et al. |
| 2005/0282196 | A1 | 12/2005 | Costa |
| 2007/0122823 | A1 | 5/2007 | Bianchi et al. |
| 2007/0202525 | A1 | 8/2007 | Quake et al. |
| 2009/0029377 | A1 | 1/2009 | Lo et al. |
| 2009/0087847 | A1 | 4/2009 | Lo et al. |
| 2010/0041048 | A1 | 2/2010 | Diehl et al. |
| 2010/0112575 | A1* | 5/2010 | Fan ...................... C12Q 1/6883 435/6.11 |
| 2010/0136560 | A1 | 6/2010 | Vogelstein et al. |
| 2013/0040824 | A1 | 2/2013 | Lo et al. |
| 2013/0237431 | A1 | 9/2013 | Lo et al. |
| 2014/0100121 | A1 | 4/2014 | Lo et al. |
| 2014/0274740 | A1 | 9/2014 | Srinivasan et al. |
| 2015/0087529 | A1 | 3/2015 | Lo et al. |
| 2016/0333416 | A1 | 11/2016 | Babiarz et al. |
| 2017/0211143 | A1 | 7/2017 | Shendure et al. |

FOREIGN PATENT DOCUMENTS

| EA | 005140 B1 | 12/2004 |
| EA | 010571 B1 | 10/2008 |
| EA | 011608 B1 | 4/2009 |
| EA | 018444 B1 | 8/2013 |
| EP | 2426217 A1 | 3/2012 |
| GB | 2485635 A | 5/2012 |
| JP | 2005514956 | 5/2005 |
| JP | 2010534068 A | 11/2010 |
| JP | 2010534069 A | 11/2010 |
| JP | 2013509884 | 3/2013 |

(Continued)

OTHER PUBLICATIONS

Meyerson et al. (Nature Reviews, Genetics; Oct. 2010, vol. 11, pp. 685-696).*
Nannya et al. (Cancer Res., 2005, 65:14, pp. 6071-6079).*
Wang, Tian-Li, et al., "Digital Karyotyping," PNAS, Dec. 10, 2002, vol. 99, No. 25, pp. 16156-16161.
Beck, Julia, et al., "Profile of the Circulating DNA in Apparently Healthy Individuals," Clinical Chemistry, 2009, vol. 55, No. 4, pp. 730-738.
Beck, Julia, et al., "Next Generation Sequencing of Serum Circulating Nucleic Acids from Patients with Invasive Ductal Breast Cancer Reveals Differences to Health and Nonmalignant Controls," American Association for Cancer Research, 2010, pp. 335-342, [online], retrieved from the internet URL: www.aacrjournals.org.

(Continued)

*Primary Examiner* — Pablo S Whaley
(74) *Attorney, Agent, or Firm* — Kilpatrick Townsend & Stockton LLP

(57) ABSTRACT

A frequency of somatic mutations in a biological sample (e.g., plasma or serum) of a subject undergoing screening or monitoring for cancer, can be compared with that in the constitutional DNA of the same subject. A parameter can derived from these frequencies and used to determine a classification of a level of cancer. False positives can be filtered out by requiring any variant locus to have at least a specified number of variant sequence reads (tags), thereby providing a more accurate parameter. The relative frequencies for different variant loci can be analyzed to determine a level of heterogeneity of tumors in a patient.

46 Claims, 26 Drawing Sheets

(56) References Cited

FOREIGN PATENT DOCUMENTS

| JP | 2014534507 | | 12/2014 |
|---|---|---|---|
| TW | 201122470 | A | 7/2011 |
| WO | 2000/061612 | A2 | 10/2000 |
| WO | 2004078999 | A1 | 9/2004 |
| WO | 2004/111272 | A2 | 12/2004 |
| WO | 2007028155 | A2 | 3/2007 |
| WO | 2007100911 | A2 | 9/2007 |
| WO | 2008/024009 | A1 | 2/2008 |
| WO | 2008/146309 | A2 | 12/2008 |
| WO | 2009/013492 | A1 | 1/2009 |
| WO | 2009/013496 | A1 | 1/2009 |
| WO | 2009019455 | A2 | 2/2009 |
| WO | 2010112316 | A1 | 10/2010 |
| WO | 2011038507 | A1 | 4/2011 |
| WO | 2011053790 | A2 | 5/2011 |
| WO | 2011054936 | A1 | 5/2011 |
| WO | 2011057094 | A1 | 5/2011 |
| WO | 2011073665 | A1 | 6/2011 |
| WO | 2011/090557 | A1 | 7/2011 |
| WO | 2011/091046 | A1 | 7/2011 |
| WO | 2011/103236 | A2 | 8/2011 |
| WO | 2012/071621 | A1 | 6/2012 |
| WO | 2013086352 | A1 | 6/2013 |
| WO | 2013138510 | A1 | 9/2013 |
| WO | 2014/039556 | A1 | 3/2014 |
| WO | 2014/130890 | A1 | 8/2014 |
| WO | 2016/015058 | A2 | 1/2016 |

OTHER PUBLICATIONS

McDermott, M. B., et al., "Genomics and the Continuum of Cancer Care," The New England Journal of Medicine, Jan. 27, 2011, pp. 340-350, [online], retrieved from the internet URL: www.nejm.org.

Stratton, Michael, R., "Exploring the Genomes of Cancer Cells: Progress and Promise," Science, Mar. 25, 2011, pp. 1553-1558, [online], retrieved from the internet URL: www.sciencemag.org.

Navin, Nicholas, et al., "Future Medical Applications of Single-Cell Sequencing in Cancer," Genome Medicine, 2011, vol. 3, No. 31, 12 pages.

Navin, Nicholas, et al., "Tumour Evolution Inferred by Single-Cell Sequencing," Nature, Apr. 7, 2011, vol. 472, 6 pages.

Diaz, Luis, A., Jr., et al., "The Molecular Evolution of Acquired Resistance to Targeted EGFR Blockade in Colorectal Cancers," Nature, 2012, 4 pages.

Diaz, Luis, A., Jr., et al., "Supplemental Information," Nature, 2012, 25 pages.

Longo, Dan L., "Tumor Heterogeneity and Personalized Medicine," The New England Journal of Medicine, Mar. 8, 2012, 2 pages, [online], retrieved from the internet URL: www.nejm.org.

Yap, Timothy, A., et al., "Intratumor Heterogeneity: Seeing the Wood for the Trees," ScienceTranslationalMedicine, Mar. 28, 2012, vol. 4, Issue 127, 4 pages, [online], retrieved from the internet URL: www.sciencetranslationalmedicine.org.

Gerlinger, Marco, et al., "Intratumor Heterogeneity and Branched Evolution Revealed by Multiregion Sequencing," The New England Journal of Medicine, Mar. 8, 2012, pp. 883-892, [online], retrieved from the internet URL: www.nejm.org.

Hou, Yong, et al., "Single-Cell Exome Sequencing and Monoclonal Evolution of a JAK2-Negative Myeloproliferative Neoplasm," Cell, Mar. 2, 2012, pp. 873-885.

"Single-Cell Sequencing Tackles Basic and Biomedical Questions," Science, May 25, 2012, vol. 336, 2 pages, [online], retrieved from the internet URL: www.sciencemag.org.

Xu, Xun, et al., "Single-Cell Exome Sequencing Reveals Single-Nucleotide Mutation Characteristics of a Kidney Tumor," Cell, Mar. 2, 2012, pp. 886-895.

Leary, Rebecca, J., et al., "Detection of Chromosomal Alterations in the Circulation of Cancer Patients with Whole-Genome Sequencing," ScienceTranslationalMedicine, Nov. 28, 2012, vol. 4, Issue 162, 13 pages, [online], retrieved from the internet URL: www.sciencetranslationalmedicine.org.

Leary, Rebecca, J., et al., Supplemental Materials, ScienceTranslationalMedicine, Nov. 28, 2012, 9 pages.

"Detectable Clonal Mosaicism and its Relationship to Aging and Cancer," Nature Genetics, Jun. 2012, vol. 44, No. 6, pp. 651-660.

Kitzman, Jacob, O., et al., "Noninvasive Whole-Genome Sequencing of a Human Fetus," ScienceTranslationalMedicine, Jun. 6, 2012, vol. 4, Issue 137, 11 pages, [online], retrieved from the internet URL: www.sciencetranslationalmedicine.org.

Kitzman, Jacob, O., et al., "Supplemental Materials," ScienceTranslationalMedicine, Jun. 6, 2012, 11 pages.

Welch, John, S., et al., "The Origin and Evolution and Mutations in Acute Myeloid Leukemia," Cell, Jul. 20, 2012, pp. 264-278.

Liao, Gary J.W., et al., "Targeted Massively Parallel Sequencing of Maternal Plasma DNA Permits Efficient and Unbiased Detection of Fetal Alleles;" 2011; Clinical Chemistry; vol. 57; No. 1; pp. 92-101.

Lun, Fiona M. F., et al., "Noninvasive prenatal diagnosis of monogenic diseases by digital size selection and relative mutation dosage on DNA in maternal plasma;" Dec. 16, 2008; PNAS; vol. 105; No. 50; pp. 19920-19925.

Schwarzenbach, Heidi, et al., "Cell-free nucleic acids as biomarkers in cancer patients;" Jun. 2011; Nature; vol. 11, pp. 426-437.

Prokunina-Olsson, Ludmilla and Chanock, Stephen J., "Cancer Sequencing Gets a Little More Personal;" Feb. 24, 2010; www.ScienceTranslationalMedicine.org; vol. 2; Issue 20; pp. 1-3.

Mueller, Imke, et al., "Identification of Loss of Heterozygosity on Circulating Free DNA in Peripheral Blood of Prostate Cancer Patients: Potential and Technical Improvements;" 2008; Clinical Chemistry; vol. 54; No. 4; pp. 688-696.

Psifidi, Androniki, et al., "Novel Quantitative Real-Time LCR for the Sensitive Detection of SNP Frequencies in Pooled DNA: Method Development, Evaluation and Application;" Jan. 1, 2011; PLoS One; vol. 6; Issue 1; pp. 1-11.

Salani, Ritu, et al., "Benign Effusions Length in Cell-Free DNA Distinguish Malignant versus Measurement of Cyclin E Genomic Copy Number and Strand;" Published online Oct. 1, 2007; Clin Cancer Res 2007; vol. 13; pp. 5805-5809.

Weber, Axel, et al., "Detection of human tumor cells by amplicon fusion site polymerase chain reaction (AFS-PCR);" Feb. 2011; The Journal of Clinical Investigation; vol. 121; No. 2; 545-553.

Chang, Hsueh-Wei, et al., "Assessment of Plasma DNA Levels, Allelic Imbalance, and CA 125 as Diagnostic Tests for Cancer;" Nov. 20, 2002; Journal of the National Cancer Institute; vol. 94; No. 22; pp. 1697-1703.

Hanlon, Katy, et al., "Evaluation of 13q14 Status in Multiple Myeloma by Digital Single Nucleotide Polymorphism Technology;" Sep. 2009; Journal of Molecular Diagnostics; vol. 11; No. 5; pp. 450-457.

Qin, Jian, et al., "Studying copy number variations using a nanofluidic platform;" 2008; Nucleic Acids Research; vol. 36; No. 18; pp. 1-8.

Shaw, Jacqueline A., et al., "Genomic analysis of circulating cell free DNA infers breast cancer dormancy;" published online Oct. 11, 2011; Genome Res; 13 pages.

Snyder, Thomas M., "Universal noninvasive detection of solid organ transplant rejection;" Apr. 12, 2011; PNAS; vol. 108; No. 15; pp. 6229-6234.

Yung, Tony, K.F., et al., "Single-Molecule Detection of Epidermal Growth Factor Receptor Mutations in Plasma by Microfluidics Digital PCR in Non-Small Cell Lung Cancer Patients;" Mar. 15, 2009; Clin Cancer Res 2009; vol. 15, No. 6; pp. 2076-2084.

Diehl, Frank, et al., "Circulating mutant DNA to assess tumor dynamics;" published online Jul. 31, 2008; Nature Medicine; pp. 1-6.

Diehl, Frank, et al., "Detection and quantification of mutations in the plasma of patients with colorectal tumors;" Nov. 8, 2005; PNAS; vol. 102; No. 45; pp. 16368-16373.

Jung, Klaus, et al., "Cell-free DNA in the blood as a solid tumor biomarker—A critical appraisal of the literature;" 2010; Clinica Chimica Acta; vol. 411; pp. 1611-1624.

Leary, Rebecca J., et al., "Development of Personalized Tumor Biomarkers Using Massively Parallel Sequencing;" Feb. 24, 2010; www.ScienceTranslationalMedicine.org; vol. 2; Issue 20; 8 pages.

(56) References Cited

OTHER PUBLICATIONS

Taback, B., et al., "Prognostic Significance of Circulating Microsatellite Markers in the Plasma of Melanoma Patients", Cancer Research, Aug. 1, 2001, vol. 61, pp. 5723-5726.
Tao, et al., "Rapid growth of a hepatocellular carcinoma and the driving mutations revealed by cell-population genetic analysis of whole-genome data," PNAS, 2011, vol. 108, No. 29, pp. 12042-12047.
Chan, K.C.A., et al., "Cancer genome scanning in plasma: detection of tumor-associated copy number aberrations, single-nucleotide variants, and tumoral heterogeneity by massively parallel sequencing," Clinical Chemistry, 2013, vol. 59, No. 1, pp. 211-224.
Chan, K.C.A., et al., "Noninvasive detection of cancer-associated genome-wide hypomethylation and copy number aberrations of plasma DNA bisulfite sequencing," PNAS, Nov. 19, 2013, vol. 110, No. 47, pp. 18761-18768.
Xie, C., et al., "CNV-seq, a new method to detect copy number variation using high-throughput sequencing," BMC Bioinformatics, 2009, vol. 10, No. 80.
International Search Report and Written Opinion dated Dec. 23, 2013 in PCT/IB2013/054898, 16 pages.
Supplemental European Search Report dated Feb. 15, 2016, 11 pages.
Fan, et al., "Whole-Genome Molecular Haplotyping of Single Cells," Nature Biotechnology, vol. 29, No. 1 Jan. 2011, pp. 51-59.
Forshew, et al., "Noninvasive Identification and Monitoring of Cancer Mutations by Targeted Deep Sequencing of Plasma DNA," Science Translational Medicine, May 30, 2012, vol. 4, Issue 136, pp. 1-12.
Mouliere et al., "High Fragmentation Characterizes Tumour-Derived Circulating DNA," PLoS One, Sep. 2011, vol. 6, Issue 9, pp. 1-10.
Su et al., "Inferring Combined CNV/SNP Haplotypes from Genotype Data," Bioinformatics, vol. 26, No. 11, 2010, pp. 1437-1445.
Lafambroise, Thomas et al.; "Allele-Specific Amplification in Cancer Revealed by SNP Array Analysis"; PLoS Computational Biology; 2005; vol. 1, Issue 6; pp. 0507-0517.
Thierry, Alain R. et al.; "Origin and quantification of circulating DNA in mice with human colorectal cancer xenografts"; Nucleic Acids Research; 2010; vol. 38, No. 18; pp. 6159-6175.
Zhao, Xiaojun et al.; "Homozygous Deletions and Chromosome Amplifications in Human Lung Carcinomas Revealed by Single Nucleotide Polymorphism Array Analysis"; Cancer Research; 2005; 65: (13); pp. 5561-5570.
International Search Report and Written Opinion dated Feb. 17, 2012 in International Application No. PCT/AU2011/001562. 8 pages.
Fan, H. Christina et al.; "Analysis of the Size Distributions of Fetal and Maternal Cell-Free DNA by Paired-End Sequencing"; Clinical Chemistry; 2010; 56:8; pp. 1279-1286.
Yu, Stephanie C. Y. et al.; "Size-based molecular diagnostics using plasma DNA for noninvasive prenatal testing"; PNAS; 2014; vol. 111, No. 23; pp. 8583-8588.
Chan, K.C. Allen et al.; "Molecular Characterization of Circulating EBV DNA in the Plasma of Nasopharyngeal Carcinoma and Lymphoma Patients"; Cancer Research; 2003; 63; pp. 2028-2032.
Ellinger, Jörg et al.; "Cell-Free Circulating DNA: Diagnostic Value in Patients With Testicular Germ Cell Cancer"; The Journal of Urology; 2009; vol. 181, pp. 363-371.
International Search Report and Written Opinion dated Jun. 18, 2013 in International Application No. PCT/IB2013/000312. 13 pages.
Lo., Y.M. Dennis et al.; "Maternal Plasma DNA Sequencing Reveals the Genome-Wide Genetic and Mutational Profile of the Fetus"; Science Translational Medicine; 2010; vol. 2, Issue 61; 14 pages; retrieved from the internet URL: www.stm.sciencemag.org.
Fan, H. Christina et al.; "Detection of Aneuploidy with Digital Polymerase Chain Reaction"; Analytical Chemistry; 2007; vol. 79, No. 19; pp. 7576-7579.

Chan, K.C. Allen et al.; "Size Distributions of Maternal and Fetal DNA in Maternal Plasma"; Clinical Chemistry; 2004; 50:1; pp. 88-92.
Ding, Chunming et al.; "MS analysis of single-nucleotide differences in circulating nucleic acids: Application to noninvasive prenatal diagnosis"; PNAS; 2004; vol. 101, No. 29; pp. 10762-10767.
Reed, W. et al.; "Non-invasive determination of the paternal HLA haplotype of a fetus using kinetic PCR to detect fetal microchimerism in maternal plasma"; Bone Marrow Transplantation; 2002; 29; pp. 527-529.
Chiu, Rossa W.K. et al.; "Non-invasive prenatal diagnosis by single molecule counting technologies"; Trends in Genetics; 2009; vol. 25, No. 7; pp. 324-331.
Fan, H. Christina et al.; "Noninvasive diagnosis of fetal aneuploidy by shotgun sequencing DNA from maternal blood"; PNAS; 2008; vol. 105, No. 42; pp. 16266-16271.
Chiu, Rossa W.K. et al.; "Noninvasive prenatal diagnosis of fetal chromosomal aneupoloidy by massively parallel genomic sequencing of DNA in maternal plasma"; PNAS; 2008; vol. 105, No. 51; pp. 20458-20463.
Larrabee, Paige B. et al.; "Microarray Analysis of Cell-Free Fetal DNA in Amniotic Fluid: a Prental Molecular Karyotype"; The American Journal of Human Genetics; 2004; 75; pp. 485-491.
Li, Ying et al.; "Size Separation of Circulatory DNA in Maternal Plasma Permits Ready Detection of Fetal DNA Polymorphisms"; Clinical Chemistry; 2004; 50:6; pp. 1002-1011.
Lo, Y.M. Dennis et al.; "Digital PCR for the molecular detection of fetal chromosomal aneuploidy"; PNAS; 2007; vol. 104, No. 32, pp. 13116-13121.
Peter, Inga et al.; "Cell-free DNA Fragmentation Patterns in Amniotic Fluid Identify Genetic Abnormalities and Changes due to Storage"; Diagnostic Molecular Pathology; 2008; pp. 185-190.
Lapaire, Olav et al.; "Larger Columns and Change of Lysis Buffer Increase the Yield of Cell-Free DNA Extracted from Amniotic Fluid"; Letters to the Editor, Clinical Chemistry; 2006; 52:1; pp. 156-157.
Lapaire, Olav et al.; "Cell-Free Fetal DNA in Amniotic Fluid: Unique Fragmentation Signatures in Euploid and Aneuploid Fetuses"; Clinical Chemistry; 2007; 53:3; pp. 405-411.
Lapaire, Olav et al.; "Array-CGH analysis of cell-free fetal DNA in 10mL of amniotic fluid supernatant"; Prenatal Diagnosis; 2007; 27; pp. 616-621.
Bianchi, Diana W. et al.; "Large Amounts of Cell-free Fetal DNA Are Present in Amniotic Fluid"; Clinical Chemistry; 2001; 47:10; pp. 1867-1869.
Lecoeur, Hervé; "Nuclear Apoptosis Detection by Flow Cytometry: Influence of Endogenous Endonucleases"; Experimental Cell Research; 2002; 277; pp. 1-14.
Jiang, Wei-Wen et al.; "Increased plasma DNA integrity index in head and neck cancer patients"; International Journal of Cancer; 2006; 119; pp. 2673-2676.
Zheng, Yama W.L. et al.; "Nonhematopoietically Derived DNA Is Shorter than Hematopoietically Dervied DNA in Plasma: A Transplantation Model"; Clinical Chemistry; 2012; 58:3; pp. 549-558.
Jahr, Sabine et al.; "DNA Fragments in the Blood Plasma of Cancer Patients: Quantitations and Evidence for Their Origin from Apoptotic and Necrotic Cells"; Cancer Research; 2001; 61; pp. 1659-1665.
International Search Report and Written Opinion dated Apr. 20, 2011 in International Application No. PCT/US2010/055655. 20 pages.
International Search Report and Written Opinion dated Feb. 23, 2011 in International Application No. PCT/EP2010/066935. 13 pages.
English translation of Office Action dated Jul. 26, 2016 in JP Patent Application No. 2015-517896. 11 pages.
Written Opinion dated Aug. 4, 2016 in SG Patent Application No. 11201408113Q. 9 pages.
Miller, Suzanne et al.; "Genome-wide molecular characterization of central nervous system primitive neuroectodermal tumor and pineoblastoma"; Neuro-Oncology; 2011; 13(8); pp. 866-879.

(56) References Cited

OTHER PUBLICATIONS

Nannya, Yasuhito et al.; "A Robust Algorithm for Copy Number Detection Using High-Density Oglionucleotide Single Nucleotide Polymorphism Genotyping Arrays"; Cancer Research; 2005; 65: (14); pp. 6071-6079.
Examination Report No. 1 dated Aug. 17, 2016 in AU Patent Application No. 2013278994. 3 pages.
Office Action dated Mar. 23, 2016 in CA Patent Application No. 2,876,327. 4 pages.
English translation of Office Action dated Oct. 25, 2016 in KR Patent Application 10-2015-7001225. 8 pages.
English translation of Office Action dated Feb. 8, 2017 in TW Patent Application No. 102122036. 3 pages.
Communication pursuant to Article 94(3) EPC dated Feb. 27, 2017 in EP Patent Application No. 13807105.5. 10 pages.
Official Notification dated Mar. 10, 2017 in EA Patent Application No. 201500027, with English translation. 19 pages.
English translation of Office Action dated Aug. 14, 2017 in IL Patent Application No. 235967. 4 pages.
Palomaki, Glenn E. et al.; "DNA sequencing of maternal plasma to detect Down syndrome: An international clinical validation study"; Genetics in Medicine; Nov. 2011; vol. 13, No. 11; pp. 913-920 and online material appendices (73 pages).
Office Action dated Jul. 7, 2017 in CA Patent Application No. 2,876,327. 4 pages.
Stratton, Michael R. et al.; "The cancer genome"; Nature; Apr. 9, 2009; vol. 458; doi:10.1038/nature07943; pp. 719-724.
Written Opinion dated Aug. 16, 2017 in SG Patent Application No. 11201408113Q. 8 pages.
English translation of Office Action dated Dec. 19, 2017 in EA Patent Application No. 201500027. 3 pages.
Daniels, Melissa et al.; "Whole genome sequencing for lung cancer"; Journal of Thoracic Disease; Apr. 2012; vol. 4, No. 2; pp. 155-163.
English translation of Office Action dated Apr. 10, 2018 in IL Patent Application No. 235967. 3 pages.
Written Opinion dated Jun. 19, 2018 in SG Patent Application No. 11201706529T. 8 pages.
Snyder, Matthew W. et al.; "Noninvasive fetal genome sequencing: a primer"; Prenatal Diagnosis; NIH Public Access Author Manuscript; published online Apr. 1, 2013; doi 10.1002/pd.4097; published in final edited form Jun. 2013; vol. 33, No. 6; pp. 547-544 (14 pages).
Karlsson, Kasper et al.; "Amplification-free sequencing of cell-free DNA for prenatal non-invasive diagnosis of chromosomal aberrations"; Genomics; 2015; vol. 105, No. 3; pp. 150-158.
Notice of Allowance dated Jun. 28, 2018 in U.S. Appl. No. 15/362,631, filed Nov. 28, 2016. 7 pages.
Notice of Allowance dated Aug. 10, 2018 in U.S. Appl. No. 15/362,631, filed Nov. 28, 2016. 5 pages.
International Search Report and Written Opinion dated Jan. 12, 2016 in International Patent Application No. PCT/US2015/042310. 16 pages.
Murtaza, Muhammed et al.; "Non-invasive analysis of acquired resistance to cancer therapy by sequencing of plasma DNA"; Nature; Letter; May 2, 2013; vol. 497; pp. 108-112 (6 pages).
Illumina, Inc.; "TruSeq DNA PCR-Free Sample Preparation Kit"; Data Sheet: Sequencing [online]; © 2013 Illumina, Inc.; Retrieved from the internet: <URL: https://www.encodeproject.org/documents/06fd4dd5-4669-4f8e-ab41-397080e9804e/%40%40download/attachment/PCR_Free_WGS.pdf>; retrieved on Aug. 9, 2018; 4 pages.
Razavi et al.; "Many cell-free DNA (cfDNA) mutations are derived from clonal hematopoiesis: Implications for interpretation of liquid biopsy tests" [online]; GRAIL-MSK WBC Poster; ASCO; Jun. 2017; Retrieved from the internet: <URL: https://grail.com/publication/many-cell-free-dna-cfdna-mutations-are-derived-from-clonal-hematopoiesis-implications-for-interpretation-of-liquid-biopsy-tests/>; retrieved on Aug. 23, 2018; 1 page (followed by 40 pages of enlarged sections for the sake of legibility).
Razavi et al.; "Performance of a high-intensity 508-gene circulating-tumor DNA (ctDNA) assay in patients with metastatic breast, lung, and prostate cancer" [online]; GRAIL-MSK concordance Poster; ASCO; Jun. 2017; Retrieved from the internet: <URL: https://grail.com/wp-content/uploads/2018/05/ASCO_2017_Razavi_Concordance_POS_Final.pdf>; 1 page (followed by 40 pages of enlarged sections for the sake of legibility).
Snyder, Matthew W. et al.; "Cell-free DNA Comprises an In Vivo Nucleosome Footprint that Informs Its Tissues-Of-Origin"; Cell; Jan. 14, 2016; 164; 57-68 (30 pages).
English translation of Office Action dated Oct. 22, 2018 in EA Patent Application No. 201500027. 5 pages.
Notice of Allowance dated Oct. 31, 2018 in U.S. Appl. No. 15/362,631, filed Nov. 28, 2016. 5 pages.
Examination Report No. 1 dated Nov. 21, 2018 in AU Patent Application No. 2017204558. 11 pages.
Mitchell, William Marvin et al.; "High Sensitivity and Specificity of Chromosomal Pertubations in Human Invasive Breast Cancer (BrCa) Associated with Circulating Nucleic Acids (CNA) Using Concatemers of Short Sequence DNA Tags in Next Generation Sequencing (NGS)"; Experimental Biology Meeting 2011; Washington, DC, USA; Apr. 9-13, 2011; The FASEB Journal; vol. 25, No. 1_supplement; Apr. 2011 PREV201300063370; 1 page.
Larkin, J.M.G. et al.; "A phase II trial of nilotinib in the treatment of patients with KIT mutated advanced acral and mucosal melanoma (NICAM)" (online conference poster); Retrieved from the internet: <URL: https://media4.asco.org/102/6682/59779/59779_poster_big_1.jpg>; retrieved on Jan. 24, 2019; 1 page (followed by 4 pages of enlarged sections for the sake of legibility).
Larkin, J.M.G. et al.; "A phase II trial of nilotinib in the treatment of patients with KIT mutated advanced acral and mucosal melanoma (NICAM)"; Journal of Clinical Oncology (2011), vol. 29, No. 15_suppl, TPS229-TPS229; 3 pages.
Extended European Search Report dated Nov. 29, 2018 in EP Patent Application No. 18185290.6. 18 pages.
English translation of Office Action dated Nov. 29, 2018 in IL Patent Application No. 235967. 3 pages.
English translation of Office Action dated Feb. 6, 2018 in JP Patent Application No. 2015-517896. 4 pages.
Aird, Daniel et al.; "Analyzing and minimizing PCR amplification bias in Illumina sequencing libraries"; Genome Biology; 2011; 12:R18; http://genomebiology.com/2011/12/2/R18; 14 pages.
Goode, David L. et al.; "A simple consensus approach improves somatic mutation prediction accuracy"; Genome Medicine; Sep. 30, 2013; doi: 10.1186/gm494; vol. 5, No. 9.; 14 pages.
Heidary, Maryam et al.; "The dynamic range of circulating tumor DNA in metastatic breast cancer"; Breast Cancer Research; Aug. 9, 2014; doi: 10.1186/s13058-014-0421-y; vol. 16, No. 4; 10 pages.
Kinde, Isaac et al.; "Detection and quantification of rare mutations with massively parallel sequencing"; Jun. 7, 2011; PNAS; vol. 108, No. 23; pp. 9530-9535.
Kozarewa, Iwanka et al.; "Amplification-free Illumina sequencing-library preparation facilitates improved mapping and assembly of (G+C)-biased genomes"; Nature Methods; Apr. 2009; vol. 6, No. 4; pp. 291-295.
Van Dijk, Erwin L. et al.; "Library preparation methods for next-generation sequencing: Tone down the bias"; Experimental Cell Research; 2014; vol. 322; http://dx.doi.org/10.1016/j.yexcr.2014.01.008; pp. 12-20.
English translation of Office Action dated Sep. 3, 2018 in KR Patent Application No. 10-2018-7021883. 5 pages.
Extended European Search Report dated Sep. 18, 2018 in EP Patent Application No. 16748745.3. 9 pages.
Cibulskis, Kristian et al; "Sensitive detection of somatic point mutations in impure and heterogeneous cancer samples"; Nature Biotechnology; Mar. 2013; vol. 31, No. 3; pp. 213-219.
Office Action dated Feb. 8, 2019 in CA Patent Application No. 2,876,327. 4 pages.
English translation of Office Action dated Mar. 22, 2019 in KR Patent Application No. 10-2018-7021883. 5 pages.
English translation of Office Action dated Sep. 17, 2019 in JP Patent Application No. 2018-132118. 6 pages.

(56) References Cited

OTHER PUBLICATIONS

Notice of Eligibility for Grant (with Examination Report) dated May 14, 2019 in SG Patent Application No. 11201706529T. 7 pages.
English translation of Office Action dated Oct. 30, 2020 in TW Patent Application No. 107128593. 5 pages.
English translation of Office Action dated Jul. 1, 2020 in KR Patent Application No. 10-2020-7009028. 5 pages.
English translation of Search Report dated Aug. 31, 2020 in TW Patent Application No. 105104407. 2 pages.
Examination Report No. 1 dated Jun. 28, 2021 in AU Patent Application No. 2020200122. 5 pages.

* cited by examiner

300

310 — Align at least a portion of the sequence tags from biological sample to the reference genome

320 — Identify a first number (A) of potential variants relative to the reference genome

330 — Determine constitutional genome by aligning sequence tags obtained by sequencing DNA fragments from a constitutional sample to the reference genome

340 — Identify a second number (B) of loci where an aligned sequence tag of the CG has a variant at a locus relative to the reference genome

350 — Subtract B from A to identify variants (SNMs) that are present in the sample genome but not in CG.

FIG. 3

| No. of times seen | 1x | | 2x | | 3x | | 4x | | 5x | | 6x | |
|---|---|---|---|---|---|---|---|---|---|---|---|---|
| Sequencing Depth | Expect no. false positives loci for sequencing errors | Expect no. of mutations identified | Expect no. false positives loci for sequencing errors | Expect no. of mutations identified | Expect no. false positives loci for sequencing errors | Expect no. of mutations identified | Expect no. false positives loci for sequencing errors | Expect no. of mutations identified | Expect no. false positives loci for sequencing errors | Expect no. of mutations identified | Expect no. false positives loci for sequencing errors | Expect no. of mutations identified |
| 1 | 2,998,500 | 146 | 1,499 | 4 | 0 | 0 | 0 | 0 | 0 | 0 | 0 | 0 |
| 10 | 29,850,499 | 1,180 | 45,000 | 271 | 40 | 43 | 0 | 5 | 0 | 1 | 0 | 0 |
| 20 | 59,403,980 | 1,896 | 190,000 | 793 | 380 | 241 | 1 | 57 | 0 | 11 | 0 | 2 |
| 40 | 117,631,683 | 2,594 | 780,000 | 1,782 | 3,293 | 970 | 10 | 429 | 0 | 158 | 0 | 50 |
| 60 | 174,706,399 | 2,851 | 1,770,000 | 2,403 | 11,407 | 1,730 | 54 | 1,058 | 0 | 554 | 0 | 252 |
| 80 | 230,650,961 | 2,945 | 3,160,000 | 2,725 | 27,387 | 2,286 | 176 | 1,700 | 1 | 1,113 | 0 | 645 |
| 100 | 285,487,746 | 2,980 | 4,950,000 | 2,879 | 53,900 | 2,626 | 436 | 2,205 | 3 | 1,679 | 0 | 1,152 |
| 120 | 339,238,690 | 2,993 | 7,140,000 | 2,948 | 93,613 | 2,814 | 913 | 2,546 | 7 | 2,145 | 0 | 1,663 |
| 140 | 391,925,294 | 2,997 | 9,730,000 | 2,978 | 149,193 | 2,911 | 1,703 | 2,755 | 15 | 2,481 | 0 | 2,098 |
| 160 | 443,568,633 | 2,999 | 12,720,000 | 2,991 | 223,307 | 2,959 | 2,922 | 2,873 | 30 | 2,701 | 0 | 2,426 |
| 180 | 494,189,366 | 3,000 | 16,110,000 | 2,996 | 318,620 | 2,981 | 4,700 | 2,936 | 55 | 2,835 | 1 | 2,653 |
| 200 | 543,807,741 | 3,000 | 19,900,000 | 2,999 | 437,800 | 2,992 | 7,187 | 2,969 | 94 | 2,912 | 1 | 2,799 |

| no. of times seen | 1x | | 2x | | 3x | | 4x | | 5x | | 6x | |
|---|---|---|---|---|---|---|---|---|---|---|---|---|
| Sequencing depth | Expect no. false positives loci for sequencing errors | Expect no. of mutations identified | Expect no. false positives loci for sequencing errors | Expect no. of mutations identified | Expect no. false positives loci for sequencing errors | Expect no. of mutations identified | Expect no. false positives loci for sequencing errors | Expect no. of mutations identified | Expect no. false positives loci for sequencing errors | Expect no. of mutations identified | Expect no. false positives loci for sequencing errors | Expect no. of mutations identified |
| 1 | 2,998,500 | 74 | 1,499 | 1 | 0 | 0 | 0 | 0 | 0 | 0 | 0 | 0 |
| 10 | 29,850,499 | 664 | 45,000 | 79 | 40 | 6 | 0 | 0 | 0 | 0 | 0 | 0 |
| 20 | 59,403,980 | 1,180 | 190,000 | 271 | 380 | 43 | 1 | 5 | 0 | 1 | 0 | 0 |
| 40 | 117,631,683 | 1,896 | 780,000 | 793 | 3,293 | 241 | 10 | 57 | 0 | 11 | 0 | 2 |
| 60 | 174,706,399 | 2,331 | 1,770,000 | 1,327 | 11,407 | 573 | 54 | 197 | 0 | 56 | 0 | 13 |
| 80 | 230,650,961 | 2,594 | 3,160,000 | 1,782 | 27,387 | 970 | 176 | 429 | 1 | 158 | 0 | 50 |
| 100 | 285,487,746 | 2,754 | 4,950,000 | 2,138 | 53,900 | 1,369 | 436 | 727 | 3 | 326 | 0 | 126 |
| 120 | 339,238,690 | 2,851 | 7,140,000 | 2,403 | 93,613 | 1,730 | 913 | 1,058 | 7 | 554 | 0 | 252 |
| 140 | 391,925,294 | 2,909 | 9,730,000 | 2,592 | 149,193 | 2,037 | 1,703 | 1,390 | 15 | 824 | 0 | 427 |
| 160 | 443,568,633 | 2,945 | 12,720,000 | 2,725 | 223,307 | 2,286 | 2,922 | 1,700 | 30 | 1,113 | 0 | 645 |
| 180 | 494,189,366 | 2,967 | 16,110,000 | 2,817 | 318,620 | 2,479 | 4,700 | 1,973 | 55 | 1,404 | 1 | 891 |
| 200 | 543,807,741 | 2,980 | 19,900,000 | 2,879 | 437,800 | 2,626 | 7,187 | 2,205 | 94 | 1,679 | 1 | 1,152 |

FIG. 5

| Case | No. of SNVs detected in the tumor tissue | Time point | No. of tumor-associated SNVs sequenced from plasma (% of SNVs seen in tumor tissue) | No. of plasma DNA sequence reads showing SNVs ($p$) | No. of plasma DNA sequence reads showing wildtype sequence ($q$) | Deduced fractional concentration of tumor-derived DNA by SNV analysis ($\frac{2p}{p+q}$) | Deduced fractional concentration of tumor-derived DNA by GAAL analysis |
|---|---|---|---|---|---|---|---|
| HCC1 | 2,840 | Pre-Tx | 2,569 (94%) | 11,389 | 31,602 | 53% | 52% |
|  |  | Post-Tx | 44 (1.5%) | 91 | 46,898 | 0.4% | 1.4% |
| HCC2 | 3,105 | Pre-Tx | 1,097 (35%) | 1,490 | 57,865 | 5.0% | 4.3% |
|  |  | Post-Tx | 72 (2.3%) | 206 | 66,692 | 0.6% | 0.9% |
| HCC3 | 3,171 | Pre-Tx | 461 (15%) | 525 | 48,886 | 2.1% | 5.6% |
|  |  | Post-Tx | 31 (1%) | 67 | 58,862 | 0.2% | 0.9% |
| HCC4 | 1,334 | Pre-Tx | 201 (15%) | 248 | 18,527 | 2.6% | 7.6% |
|  |  | Post-Tx | 74 (5.5%) | 149 | 22,144 | 1.3% | 2.7% |

| Controls | HCC1 SNVs | | HCC2 SNVs | | HCC3 SNVs | | HCC4 SNVs | | All SNVs | | Fractional concentration of all tumor-associated SNVs in plasma ($\frac{2p}{p+q}$) |
|---|---|---|---|---|---|---|---|---|---|---|---|
| | Plasma DNA sequence reads showing tumor-associated SNVs | Plasma DNA sequence reads showing wildtype sequence | Plasma DNA sequence reads showing tumor-associated SNVs | Plasma DNA sequence reads showing wildtype sequence | Plasma DNA sequence reads showing tumor-associated SNVs | Plasma DNA sequence reads showing wildtype sequence | Plasma DNA sequence reads showing tumor-associated SNVs | Plasma DNA sequence reads showing wildtype sequence | Plasma DNA sequence reads showing tumor-associated SNVs (p) | Plasma DNA sequence reads showing wildtype sequence (q) | |
| C01 | 40 | 31,261 | 66 | 38,172 | 30 | 33,823 | 69 | 14,389 | 205 | 117,645 | 0.35% |
| C02 | 60 | 34,368 | 112 | 42,660 | 37 | 37,462 | 58 | 16,097 | 267 | 130,587 | 0.41% |
| C03 | 55 | 37,931 | 100 | 46,297 | 50 | 41,181 | 74 | 17,039 | 279 | 142,448 | 0.39% |
| C04 | 41 | 40,277 | 87 | 48,441 | 39 | 43,541 | 87 | 17,358 | 254 | 149,617 | 0.34% |
| C05 | 42 | 31,655 | 71 | 38,787 | 46 | 34,566 | 70 | 14,821 | 229 | 119,829 | 0.38% |
| C06 | 41 | 34,604 | 97 | 43,999 | 26 | 37,477 | 79 | 16,762 | 243 | 132,842 | 0.37% |
| C07 | 52 | 38,664 | 118 | 47,200 | 61 | 41,840 | 72 | 17,601 | 303 | 145,305 | 0.42% |
| C08 | 57 | 38,514 | 131 | 46,464 | 42 | 41,662 | 81 | 17,275 | 311 | 143,915 | 0.43% |
| C09 | 41 | 34,945 | 115 | 43,760 | 33 | 38,039 | 81 | 16,503 | 270 | 133,247 | 0.40% |
| C10 | 44 | 35,197 | 89 | 43,622 | 51 | 38,370 | 65 | 16,009 | 249 | 133,198 | 0.37% |
| C11 | 41 | 36,693 | 95 | 45,108 | 39 | 39,732 | 72 | 16,801 | 247 | 138,334 | 0.36% |
| C12 | 45 | 39,506 | 104 | 50,085 | 46 | 42,536 | 91 | 18,598 | 286 | 150,725 | 0.38% |
| C13 | 36 | 33,799 | 71 | 40,309 | 39 | 36,241 | 70 | 14,450 | 216 | 124,799 | 0.35% |
| C14 | 42 | 38,199 | 104 | 47,832 | 42 | 41,245 | 91 | 17,807 | 279 | 145,083 | 0.38% |
| C15 | 49 | 36,106 | 90 | 43,129 | 41 | 38,432 | 73 | 16,154 | 253 | 133,821 | 0.38% |
| C16 | 38 | 33,633 | 66 | 40,023 | 41 | 36,431 | 52 | 14,502 | 197 | 124,589 | 0.32% |
| | | | | | | | | | | Mean | 0.38% |

| No. of times detected in plasma (N) | No. of potential mutations detected N times in plasma | No. of potential mutations detected ≥ N times in plasma | Tumor mutations detected N times in plasma | Tumor mutations detected ≥N times in plasma | Percentage of mutations detected compared with N=1 | Positive predictive value |
|---|---|---|---|---|---|---|
| 1 | 3,605,085 | 3,623,970 | 61 | 2,064 | 100% | 0.06% |
| 2 | 13,518 | 18,885 | 35 | 2,003 | 97% | 11% |
| 3 | 2,029 | 5,367 | 71 | 1,968 | 95% | 37% |
| 4 | 766 | 3,338 | 83 | 1,897 | 92% | 57% |
| 5 | 437 | 2,572 | 140 | 1,814 | 88% | 71% |
| 6 | 313 | 2,135 | 161 | 1,674 | 81% | 78% |
| 7 | 265 | 1,822 | 165 | 1,513 | 73% | 83% |
| 8 | 261 | 1,557 | 192 | 1,348 | 65% | 87% |
| 9 | 231 | 1,296 | 185 | 1,156 | 56% | 89% |
| 10 | 191 | 1,065 | 160 | 971 | 47% | 91% |
| 11 | 179 | 874 | 165 | 811 | 39% | 93% |
| 12 | 148 | 695 | 137 | 646 | 31% | 93% |
| 13 | 122 | 547 | 109 | 509 | 25% | 93% |
| 14 | 99 | 425 | 92 | 400 | 19% | 94% |
| 15 | 74 | 326 | 71 | 308 | 15% | 94% |
| 16 | 54 | 252 | 49 | 237 | 11% | 94% |
| 17 | 39 | 198 | 39 | 188 | 9% | 95% |
| 18 | 35 | 159 | 33 | 149 | 7% | 94% |
| 19 | 24 | 124 | 23 | 116 | 6% | 94% |
| 20 | 20 | 100 | 20 | 93 | 5% | 93% |
| 21 | 18 | 80 | 17 | 73 | 4% | 91% |
| 22 | 11 | 62 | 10 | 56 | 3% | 90% |
| 23 | 9 | 51 | 9 | 46 | 2% | 90% |
| 24 | 8 | 42 | 5 | 37 | 2% | 88% |
| 25 | 6 | 34 | 6 | 32 | 2% | 94% |
| 26 | 7 | 28 | 5 | 26 | 1% | 93% |
| 27 | 8 | 21 | 8 | 21 | 1% | 100% |
| 28 | 1 | 13 | 1 | 13 | 1% | 100% |
| 29 | 4 | 12 | 4 | 12 | 1% | 100% |
| 30 | 8 | 8 | 8 | 8 | 0% | 100% |

| No. of times detected in plasma (N) | No. of potential mutations detected N times in plasma | No. of potential mutations detected ≥ N times in plasma | Tumor mutations detected N times in plasma | Tumor mutations detected ≥N times in plasma | Percentage of mutations detected compared with N=1 | Positive predictive value |
|---|---|---|---|---|---|---|
| 1 | 3,155,634 | 3,167,144 | 51 | 54 | 100% | <0.01% |
| 2 | 9,835 | 11,510 | 2 | 3 | 6% | 0.03% |
| 3 | 1,123 | 1,675 | 1 | 1 | 2% | 0.06% |
| 4 | 314 | 552 | - | - | - | - |
| 5 | 132 | 238 | - | - | - | - |
| 6 | 49 | 106 | - | - | - | - |
| 7 | 22 | 57 | - | - | - | - |
| 8 | 11 | 35 | - | - | - | - |
| 9 | 6 | 24 | - | - | - | - |
| 10 | 5 | 18 | - | - | - | - |
| 11 | 4 | 13 | - | - | - | - |
| 12 | 2 | 9 | - | - | - | - |
| 13 | 2 | 7 | - | - | - | - |
| 14 | 3 | 5 | - | - | - | - |
| 15 | - | 2 | - | - | - | - |
| 16 | - | 2 | - | - | - | - |
| 17 | 1 | 2 | - | - | - | - |
| 18 | - | 1 | - | - | - | - |
| 19 | 1 | 1 | - | - | - | - |
| 20 | - | - | - | - | - | - |
| 21 | - | - | - | - | - | - |
| 22 | - | - | - | - | - | - |
| 23 | - | - | - | - | - | - |
| 24 | - | - | - | - | - | - |
| 25 | - | - | - | - | - | - |
| 26 | - | - | - | - | - | - |
| 27 | - | - | - | - | - | - |
| 28 | - | - | - | - | - | - |
| 29 | - | - | - | - | - | - |
| 30 | - | - | - | - | - | - |

| Sequencing depth | Pre-treatment plasma ||| Post-treatment plasma |||
|---|---|---|---|---|---|---|
| | Percentage of nucleotides with the specified sequencing depth | Total no. nucleotide positions with single nucleotide variations detected in plasma | No. of sites with corresponding changes in tumor | Percentage of nucleotides with the specified sequencing depth | Total no. nucleotide positions with single nucleotide variations detected in plasma | No. of sites with corresponding changes in tumor |
| <50 | 36.3% | 9 | 8 | 30.5% | 0 | 0 |
| 50 – 125 | 29.9% | 15 | 15 | 31.2% | 0 | 0 |
| 126 – 235 | 18.6% | 21 | 21 | 20.8% | 0 | 0 |
| 236 – 380 | 9.4% | 7 | 6 | 10.9% | 0 | 0 |
| 381 – 560 | 4.2% | 2 | 2 | 4.8% | 0 | 0 |
| 561 – 760 | 1.6% | 3 | 3 | 1.7% | 0 | 0 |
| Total | | 57 | 55 | | 0 | 0 |

FIG. 14B  1450

| Sequencing depth | Pre-treatment plasma ||| Post-treatment plasma |||
|---|---|---|---|---|---|---|
| | Percentage of nucleotides with the specified sequencing depth | Total no. nucleotide positions with single nucleotide variations detected in plasma | No. of sites with corresponding changes in tumor | Percentage of nucleotides with the specified sequencing depth | Total no. nucleotide positions with single nucleotide variations detected in plasma | No. of sites with corresponding changes in tumor |
| <50 | 30.0% | 0 | 0 | 27.1% | 0 | 0 |
| 50 – 125 | 33.6% | 2 | 2 | 32.5% | 0 | 0 |
| 126 – 235 | 21.6% | 6 | 6 | 22.2% | 0 | 0 |
| 236 – 380 | 10.2% | 5 | 5 | 11.5% | 0 | 0 |
| 381 – 560 | 3.7% | 4 | 4 | 4.9% | 0 | 0 |
| 561 – 760 | 0.9% | 1 | 1 | 1.7% | 0 | 0 |
| Total | | 18 | 18 | | 0 | 0 |

FIG. 15A 1500

| Sequencing depth | Pre-treatment plasma ||| Post-treatment plasma |||
|---|---|---|---|---|---|---|
| | Percentage of nucleotides with the specified sequencing depth | Total no. nucleotide positions with single nucleotide variations detected in plasma | No. of sites with corresponding changes in tumor | Percentage of nucleotides with the specified sequencing depth | Total no. nucleotide positions with single nucleotide variations detected in plasma | No. of sites with corresponding changes in tumor |
| <50 | 38.8% | 0 | 0 | 18.5% | 0 | 0 |
| 50 – 125 | 45.7% | 0 | 0 | 28.6% | 0 | 0 |
| 126 – 235 | 15.2% | 0 | 0 | 25.1% | 0 | 0 |
| 236 – 380 | 0.2% | 0 | 0 | 16.2% | 0 | 0 |
| 381 – 560 | <0.1% | 0 | 0 | 8.3% | 0 | 0 |
| 561 – 760 | <0.1% | 0 | 0 | 3.4% | 0 | 0 |
| Total | | 0 | 0 | | 0 | 0 |

FIG. 15B 1550

| Sequencing depth | Pre-treatment plasma ||| Post-treatment plasma |||
|---|---|---|---|---|---|---|
| | Percentage of nucleotides with the specified sequencing depth | Total no. nucleotide positions with single nucleotide variations detected in plasma | No. of sites with corresponding changes in tumor | Percentage of nucleotides with the specified sequencing depth | Total no. nucleotide positions with single nucleotide variations detected in plasma | No. of sites with corresponding changes in tumor |
| <50 | 26.7% | 0 | 0 | 24.4% | 0 | 0 |
| 50 – 125 | 35.9% | 1 | 1 | 31.2% | 1 | 1 |
| 126 – 235 | 24.7% | 2 | 2 | 23.1% | 0 | 0 |
| 236 – 380 | 10.4% | 0 | 0 | 13.1% | 0 | 0 |
| 381 – 560 | 2.2% | 0 | 0 | 6.0% | 0 | 0 |
| 561 – 760 | 0.1% | 0 | 0 | 2.2% | 0 | 0 |
| Total | | 3 | 3 | | 1 | 1 |

| Sequencing depth | Pre-treatment plasma | | | Post-treatment plasma | | |
|---|---|---|---|---|---|---|
| | Percentage of nucleotides with the specified sequencing depth | Total no. nucleotide positions with single nucleotide variations detected in plasma | No. of sites with corresponding changes in tumor | Percentage of nucleotides with the specified sequencing depth | Total no. nucleotide positions with single nucleotide variations detected in plasma | No. of sites with corresponding changes in tumor |
| <50 | 31.1% | 7 | 7 | 30.8% | 0 | 0 |
| 50 – 125 | 30.3% | 14 | 14 | 33.2% | 1 | 0 |
| 126 – 235 | 20.5% | 19 | 19 | 21.6% | 0 | 0 |
| 236 – 380 | 11.3% | 13 | 13 | 10.3% | 0 | 0 |
| 381 – 560 | 5.2% | 7 | 4 | 3.5% | 0 | 0 |
| 561 – 760 | 1.8% | 4 | 2 | 0.7% | 0 | 0 |
| Total | | 64 | 59 | | 1 | 0 |

| Sequencing depth (folds) | Sensitivity when mutant is defined as being seen in the tumor tissue sequencing data for at least n times, where n= | | | | | |
|---|---|---|---|---|---|---|
| | 4 | 5 | 6 | 7 | 8 | 9 |
| 20 | 73% | 56% | 38% | 24% | 13% | 7% |
| 21 | 77% | 60% | 43% | 28% | 16% | 9% |
| 22 | 80% | 64% | 47% | 31% | 19% | 11% |
| 23 | 83% | 68% | 51% | 35% | 22% | 13% |
| 24 | 85% | 71% | 55% | 39% | 26% | 15% |
| 25 | 87% | 75% | 59% | 43% | 29% | 18% |
| 26 | 89% | 78% | 63% | 47% | 33% | 21% |
| 27 | 90% | 80% | 67% | 51% | 36% | 24% |
| 28 | 92% | 83% | 70% | 55% | 40% | 27% |
| 29 | 93% | 85% | 73% | 59% | 44% | 30% |
| 30 | 94% | 87% | 76% | 62% | 48% | 34% |
| 31 | 95% | 89% | 78% | 66% | 51% | 37% |
| 32 | 96% | 90% | 81% | 69% | 55% | 41% |
| 33 | 96% | 91% | 83% | 72% | 58% | 44% |
| 34 | 97% | 93% | 85% | 74% | 61% | 48% |
| 35 | 97% | 94% | 87% | 77% | 65% | 51% |
| 36 | 98% | 95% | 88% | 79% | 68% | 54% |
| 37 | 98% | 95% | 90% | 82% | 70% | 58% |
| 38 | 99% | 96% | 91% | 84% | 73% | 61% |
| 39 | 99% | 97% | 92% | 85% | 76% | 64% |
| 40 | 99% | 97% | 93% | 87% | 78% | 67% |
| 41 | 99% | 98% | 94% | 88% | 80% | 69% |
| 42 | 99% | 98% | 95% | 90% | 82% | 72% |
| 43 | 99% | 98% | 96% | 91% | 84% | 75% |
| 44 | 100% | 98% | 96% | 92% | 86% | 77% |
| 45 | 100% | 99% | 97% | 93% | 87% | 79% |
| 46 | 100% | 99% | 97% | 94% | 89% | 81% |
| 47 | 100% | 99% | 98% | 95% | 90% | 83% |
| 48 | 100% | 99% | 98% | 95% | 91% | 84% |
| 49 | 100% | 99% | 98% | 96% | 92% | 86% |
| 50 | 100% | 99% | 99% | 97% | 93% | 88% |
| 51 | 100% | 100% | 99% | 97% | 94% | 89% |
| 52 | 100% | 100% | 99% | 97% | 95% | 90% |
| 53 | 100% | 100% | 99% | 98% | 95% | 91% |
| 54 | 100% | 100% | 99% | 98% | 96% | 92% |
| 55 | 100% | 100% | 99% | 98% | 96% | 93% |
| 56 | 100% | 100% | 99% | 99% | 97% | 94% |
| 57 | 100% | 100% | 100% | 99% | 97% | 95% |
| 58 | 100% | 100% | 100% | 99% | 98% | 95% |
| 59 | 100% | 100% | 100% | 99% | 98% | 96% |
| 60 | 100% | 100% | 100% | 99% | 98% | 96% |
| 61 | 100% | 100% | 100% | 99% | 98% | 97% |
| 62 | 100% | 100% | 100% | 99% | 99% | 97% |
| 63 | 100% | 100% | 100% | 100% | 99% | 97% |
| 64 | 100% | 100% | 100% | 100% | 99% | 98% |
| 65 | 100% | 100% | 100% | 100% | 99% | 98% |
| 66 | 100% | 100% | 100% | 100% | 99% | 98% |
| 67 | 100% | 100% | 100% | 100% | 99% | 99% |
| 68 | 100% | 100% | 100% | 100% | 99% | 99% |
| 69 | 100% | 100% | 100% | 100% | 100% | 99% |
| 70 | 100% | 100% | 100% | 100% | 100% | 99% |

| Sequencing depth (folds) | No. of false positives in the whole genome when a mutant is defined as being seen in the tumor sequencing data for at least n times, where n= | | | | | |
|---|---|---|---|---|---|---|
| | 4 | 5 | 6 | 7 | 8 | 9 |
| 20 | 1 | 0 | 0 | 0 | 0 | 0 |
| 21 | 1 | 0 | 0 | 0 | 0 | 0 |
| 22 | 1 | 0 | 0 | 0 | 0 | 0 |
| 23 | 1 | 0 | 0 | 0 | 0 | 0 |
| 24 | 1 | 0 | 0 | 0 | 0 | 0 |
| 25 | 1 | 0 | 0 | 0 | 0 | 0 |
| 26 | 2 | 0 | 0 | 0 | 0 | 0 |
| 27 | 2 | 0 | 0 | 0 | 0 | 0 |
| 28 | 2 | 0 | 0 | 0 | 0 | 0 |
| 29 | 3 | 0 | 0 | 0 | 0 | 0 |
| 30 | 3 | 0 | 0 | 0 | 0 | 0 |
| 31 | 3 | 0 | 0 | 0 | 0 | 0 |
| 32 | 4 | 0 | 0 | 0 | 0 | 0 |
| 33 | 5 | 0 | 0 | 0 | 0 | 0 |
| 34 | 5 | 0 | 0 | 0 | 0 | 0 |
| 35 | 6 | 0 | 0 | 0 | 0 | 0 |
| 36 | 7 | 0 | 0 | 0 | 0 | 0 |
| 37 | 7 | 0 | 0 | 0 | 0 | 0 |
| 38 | 8 | 0 | 0 | 0 | 0 | 0 |
| 39 | 9 | 0 | 0 | 0 | 0 | 0 |
| 40 | 10 | 0 | 0 | 0 | 0 | 0 |
| 41 | 11 | 0 | 0 | 0 | 0 | 0 |
| 42 | 12 | 0 | 0 | 0 | 0 | 0 |
| 43 | 14 | 0 | 0 | 0 | 0 | 0 |
| 44 | 15 | 0 | 0 | 0 | 0 | 0 |
| 45 | 17 | 0 | 0 | 0 | 0 | 0 |
| 46 | 18 | 0 | 0 | 0 | 0 | 0 |
| 47 | 20 | 0 | 0 | 0 | 0 | 0 |
| 48 | 22 | 0 | 0 | 0 | 0 | 0 |
| 49 | 24 | 0 | 0 | 0 | 0 | 0 |
| 50 | 26 | 0 | 0 | 0 | 0 | 0 |
| 51 | 28 | 0 | 0 | 0 | 0 | 0 |
| 52 | 30 | 0 | 0 | 0 | 0 | 0 |
| 53 | 33 | 0 | 0 | 0 | 0 | 0 |
| 54 | 35 | 0 | 0 | 0 | 0 | 0 |
| 55 | 38 | 0 | 0 | 0 | 0 | 0 |
| 56 | 41 | 0 | 0 | 0 | 0 | 0 |
| 57 | 44 | 0 | 0 | 0 | 0 | 0 |
| 58 | 47 | 0 | 0 | 0 | 0 | 0 |
| 59 | 51 | 0 | 0 | 0 | 0 | 0 |
| 60 | 54 | 0 | 0 | 0 | 0 | 0 |
| 61 | 58 | 0 | 0 | 0 | 0 | 0 |
| 62 | 62 | 0 | 0 | 0 | 0 | 0 |
| 63 | 66 | 0 | 0 | 0 | 0 | 0 |
| 64 | 71 | 0 | 0 | 0 | 0 | 0 |
| 65 | 75 | 0 | 0 | 0 | 0 | 0 |
| 66 | 80 | 0 | 0 | 0 | 0 | 0 |
| 67 | 85 | 0 | 0 | 0 | 0 | 0 |
| 68 | 90 | 0 | 0 | 0 | 0 | 0 |
| 69 | 96 | 0 | 0 | 0 | 0 | 0 |
| 70 | 102 | 0 | 0 | 0 | 0 | 0 |

FIG. 18
1800

| Category | No. of loci with a mutation | Pre-treatment plasma | | | Post-treatment plasma | | |
|---|---|---|---|---|---|---|---|
| | | No. of DNA fragments carrying wildtype alleles | No. of DNA fragments carrying mutant alleles | Fractional concentration of tumor-derived DNA | No. of DNA fragments carrying wildtype alleles | No. of DNA fragments carrying mutant alleles | Fractional concentration of tumor-derived DNA |
| A | 71 | 3,321 | 37 | 2.20% | 2,149 | 5 | 0.46% |
| B | 122 | 5,633 | 8 | 0.28% | 3,516 | 1 | 0.06% |
| C | 168 | 8,507 | 51 | 1.19% | 5,438 | 2 | 0.07% |
| D | 248 | 10,880 | 26 | 0.48% | 7,060 | 2 | 0.06% |
| AB | 10 | 423 | 21 | 9.46% | 297 | 0 | 0.00% |
| CD | 12 | 569 | 3 | 1.05% | 333 | 0 | 0.00% |
| ABCD | 2129 | 70,940 | 21,344 | 46.26% | 61,417 | 54 | 0.18% |

| Cat. | No. of loci | TC1 | TC2 | TC3 | TC4 | TC5 | TC6 | TC7 | TC8 | TC9 | TC10 | TC11 | TC12 | TC13 | TC14 | TC15 | TC16 |
|---|---|---|---|---|---|---|---|---|---|---|---|---|---|---|---|---|---|
| | | | | | | | | Healthy control subject — No (fractional concentration) of mutant alleles in plasma | | | | | | | | | |
| A | 71 | 0 | 1 (0.17%) | 1 (0.18%) | 0 | 1 (0.17%) | 1 (0.18%) | 1 (0.07%) | 1 (0.20%) | 0 | 6 (0.17%) | 0 | 0 | 1 (0.17%) | 2 (0.38%) | 0 | 2 (0.38%) |
| B | 122 | 0 | 0 | 0 | 0 | 0 | 0 | 1 (0.04%) | 0 | 1 (0.11%) | 3 (0.05%) | 1 (0.10%) | 1 (0.12%) | 0 | 0 | 0 | 1 (0.11%) |
| C | 168 | 0 | 0 | 0 | 0 | 0 | 0 | 2 (0.06%) | 0 | 2 (0.16%) | 0 | 0 | 0 | 1 (0.07%) | 0 | 0 | 0 |
| D | 248 | 0 | 0 | 1 (0.06%) | 0 | 0 | 0 | 0 | 0 | 0 | 1 (0.01%) | 0 | 0 | 1 (0.05%) | 0 | 0 | 0 |
| AB | 10 | 0 | 0 | 0 | 0 | 0 | 0 | 0 | 0 | 0 | 0 | 0 | 0 | 0 | 0 | 0 | 0 |
| CD | 12 | 0 | 0 | 0 | 0 | 0 | 0 | 0 | 0 | 0 | 1 (0.16%) | 0 | 0 | 1 (0.92%) | 0 | 0 | 0 |
| ABCD | 2129 | 11 (0.07%) | 3 (0.02%) | 2 (0.01%) | 8 (0.06%) | 5 (0.03%) | 5 (0.03%) | 10 (0.02%) | 4 (0.03%) | 4 (0.03%) | 19 (0.02%) | 3 (0.02%) | 0 | 1 (0.01%) | 5 (0.03%) | 2 (0.01%) | 4 (0.03%) |

METHOD OF MEASURING A FRACTIONAL CONCENTRATION OF TUMOR DNA

CROSS-REFERENCES TO RELATED APPLICATION

This application is a non-provisional of and claims the benefit of U.S. Provisional Patent Application No. 61/662,878, entitled "MUTATIONAL ANALYSIS OF PLASMA DNA FOR CANCER DETECTION," filed on Jun. 21, 2012; U.S. Provisional Patent Application No. 61/682,725, entitled "MUTATIONAL ANALYSIS OF PLASMA DNA FOR CANCER DETECTION," filed on Aug. 13, 2012; U.S. Provisional Patent Application No. 61/695,795, entitled "MUTATIONAL ANALYSIS OF PLASMA DNA FOR CANCER DETECTION," filed on Aug. 31, 2012; and U.S. Provisional Patent Application No. 61/711,172, entitled "MUTATIONAL ANALYSIS OF PLASMA DNA FOR CANCER DETECTION," filed on Oct. 8, 2012, which are herein incorporated by reference in its entirety for all purposes.

BACKGROUND

It has been shown that tumor-derived DNA is present in the cell-free plasma/serum of cancer patients (Chen X Q et al. Nat Med 1996; 2: 1033-1035). Most current methods are based on the direct analysis of mutations known to be associated with cancer (Diehl F et al. Proc Natl Acad Sci 2005; 102: 16368-16373; Forshew T et al. Sci Transl Med 2012; 4: 136ra68). Another method has investigated cancer-associated copy number variations detected by random sequencing of plasma DNA (U.S. Patent Publication 2013/0040824 by Lo et al.).

It is known that with time, more than one cancer cell would acquire growth advantage and produce multiple clones of daughter cells. Ultimately, the tumorous growth and/or its metastatic foci would contain a conglomerate of groups of clonal cancer cells. This phenomenon is typically referred as tumor heterogeneity (Gerlinger M et al. N Engl J Med 2012; 366: 883-892; Yap T A et al. Sci Transl Med 2012; 4: 127ps10).

Cancers are known to be highly heterogeneous, i.e. mutation profile of cancers of the same tissue type can vary widely. Therefore, the direct analysis of specific mutations can typically detect only a subset of the cases within a particular cancer type known to be associated with those specific mutations. Additionally, tumor-derived DNA is usually the minor species of DNA in human plasma; the absolute concentration of DNA in plasma is low. Therefore, the direct detection of one or a small group of cancer-associated mutations in plasma or serum may achieve low analytical sensitivity even among patients with cancers known to be harboring the targeted mutations. Furthermore, it has been shown that there is significant intratumoral heterogeneity in terms of mutations even within a single tumor. The mutations can be found in only a subpopulation of the tumor cells. The difference in the mutational profiles between the primary tumor and the metastatic lesions is even bigger. One example of intratumoral and primary-metastasis heterogeneity involves the KRAS, BRAF and PIK3CA genes in patients suffering from colorectal cancers (Baldus et al. Clin Cancer Research 2010. 16:790-9).

In a scenario in which a patient has a primary tumor (carrying a KRAS mutation but not a PIK3CA mutation) and a concealed metastatic lesion (carrying a PIK3CA mutation but not a KRAS mutation), if one focused on the detection of the KRAS mutation in the primary tumor, the concealed metastatic lesion cannot be detected. However, if one included both mutations in the analysis, both the primary tumor and the concealed metastatic lesion can be detected. Hence, the test involving both mutations would have a higher sensitivity in the detection of residual tumor tissues. Such a simple example becomes more complex when one is screening for cancer, and as one has little or no clue of the types of mutations that might occur.

It is therefore desirable to provide new techniques to perform a broad screening, detection, or assessment for cancer

SUMMARY

Embodiments can observe a frequency of somatic mutations in a biological sample (e.g., plasma or serum) of a subject undergoing screening or monitoring for cancer, when compared with that in the constitutional DNA of the same subject. Random sequencing can be used to determine these frequencies. A parameter can derived from these frequencies and used to determine a classification of a level of cancer. False positives can be filtered out by requiring any variant locus to have at least a specified number of variant sequence reads (tags), thereby providing a more accurate parameter. The relative frequencies for different variant loci can be analyzed to determine a level of heterogeneity of tumors in a patient.

In one embodiment, the parameter can be compared with the same parameter derived from a group of subjects without cancer, or with a low risk of cancer. A significant difference in the parameter obtained from the test subject and that from the group of subjects without cancer, or with a low risk of cancer, can indicate an increased risk that the test subject has cancer or a premalignant condition or would develop cancer in the future. Thus, in one embodiment, plasma DNA analysis can be conducted without prior genomic information of the tumor. Such an embodiment is thus especially useful for the screening of cancer.

In another embodiment, embodiments can also be used for monitoring a cancer patient following treatment and to see if there is residual tumor or if the tumor has relapsed. For example, a patient with residual tumor or in whom the tumor has relapsed would have a higher frequency of somatic mutations than one in whom there is no residual tumor or in whom no tumor relapse is observed. The monitoring can involve obtaining samples from a cancer patient at multiple time points following treatment for ascertaining the temporal variations of tumor-associated genetic aberrations in bodily fluids or other samples with cell-free nucleic acids, e.g. plasma or serum.

According to one embodiment, a method detects cancer or premalignant change in a subject. A constitutional genome of the subject is obtained. One or more sequence tags are received for each of a plurality of DNA fragments in a biological sample of the subject, where the biological sample includes cell-free DNA. Genomic positions are determined for the sequence tags. The sequence tags are compared to the constitutional genome to determine a first number of first loci. At each first loci, a number of the sequence tags having a sequence variant relative to the constitutional genome is above a cutoff value, where the cutoff value is greater than one. A parameter is determined based on a count of sequence tags having a sequence variant at the first loci. The parameter is compared to a threshold value to determine a classification of a level of cancer in the subject.

According to another embodiment, a method analyzes a heterogeneity of one or more tumors of a subject. A constitutional genome of the subject is obtained. One or more sequence tags are received for each of a plurality of DNA fragments in a biological sample of the subject, where the biological sample includes cell-free DNA. Genomic positions are determined for the sequence tags. The sequence tags are compared to the constitutional genome to determine a first number of first loci. At each first loci, a number of the sequence tags having a sequence variant relative to the constitutional genome is above a cutoff value, where the cutoff value is greater than one. A measure of heterogeneity of the one or more tumors is calculated based on the respective first numbers of the set of first genomic locations.

According to another embodiment, a method determines a fractional concentration of tumor DNA in a biological sample including cell-free DNA. One or more sequence tags are received for each of a plurality of DNA fragments in the biological sample. Genomic positions are determined for the sequence tags. For each of a plurality of genomic regions, a respective amount of DNA fragments within the genomic region is determined from sequence tags having a genomic position within the genomic region. The respective amount is normalized to obtain a respective density. The respective density is compared to a reference density to identify whether the genomic region exhibits a 1-copy loss or a 1-copy gain. A first density is calculated from respective densities identified as exhibiting a 1-copy loss or from respective densities identified as exhibiting a 1-copy gain. The fractional concentration is calculated by comparing the first density to another density to obtain a differential, wherein the differential is normalized with the reference density.

Other embodiments are directed to systems and computer readable media associated with methods described herein.

A better understanding of the nature and advantages of the present invention may be gained with reference to the following detailed description and the accompanying drawings.

BRIEF DESCRIPTION OF THE DRAWINGS

FIG. 3 shows a flowchart of a method 300 comparing the sample genome (SG) to the constitutional genome (CG) using the reference genome (RG) according to embodiments of the present invention.

FIG. 4 is a table 400 showing the number of cancer-associated single nucleotide mutations correctly identified using different number of occurrences as the criterion for classifying a mutation as being present in the sample according to embodiments of the present invention when the fractional concentration of tumor-derived DNA in the sample is assumed to be 10%.

FIG. 5 is a table showing the expected number of false-positive loci and the expected number of mutations identified when the fractional concentration of tumor-derived DNA in the sample is assumed to be 5%.

FIG. 8 is a table 800 showing results for 4 HCC patients before and after treatment, including fractional concentrations of tumor-derived DNA in plasma according to embodiments of the present invention.

FIG. 9 is a table 900 showing detection of the HCC-associated SNVs in 16 healthy control subjects according to embodiments of the present invention.

FIG. 13A shows a table 1300 of the analysis of mutations in the plasma of the patient with ovarian cancers and a breast cancer at the time of diagnosis according to embodiments of the present invention.

FIG. 13B shows a table 1350 of the analysis of mutations in the plasma of the patient with bilateral ovarian cancers and a breast cancer after tumor resection according to embodiments of the present invention.

FIG. 14A is a table 1400 showing detection of single nucleotide variations in plasma DNA for HCC1. FIG. 14B is a table 1450 showing detection of single nucleotide variations in plasma DNA for HCC2.

FIG. 15A is a table 1500 showing detection of single nucleotide variations in plasma DNA for HCC3. FIG. 15B is a table 1550 showing detection of single nucleotide variations in plasma DNA for HCC4.

FIG. 16 is a table 1600 showing detection of single nucleotide variations in plasma DNA for the patient with ovarian (and breast) cancer.

FIG. 17 is a table 1700 showing the predicted sensitivities of different requirements of occurrence and sequencing depths.

FIG. 18 is a table 1800 showing the predicted numbers of false positive loci for different cutoffs and different sequencing depths.

FIG. 20 is a table 2000 showing the number of fragments carrying the tumor-derived mutations in the pre-treatment and post-treatment plasma sample.

DEFINITIONS

Figure 1:
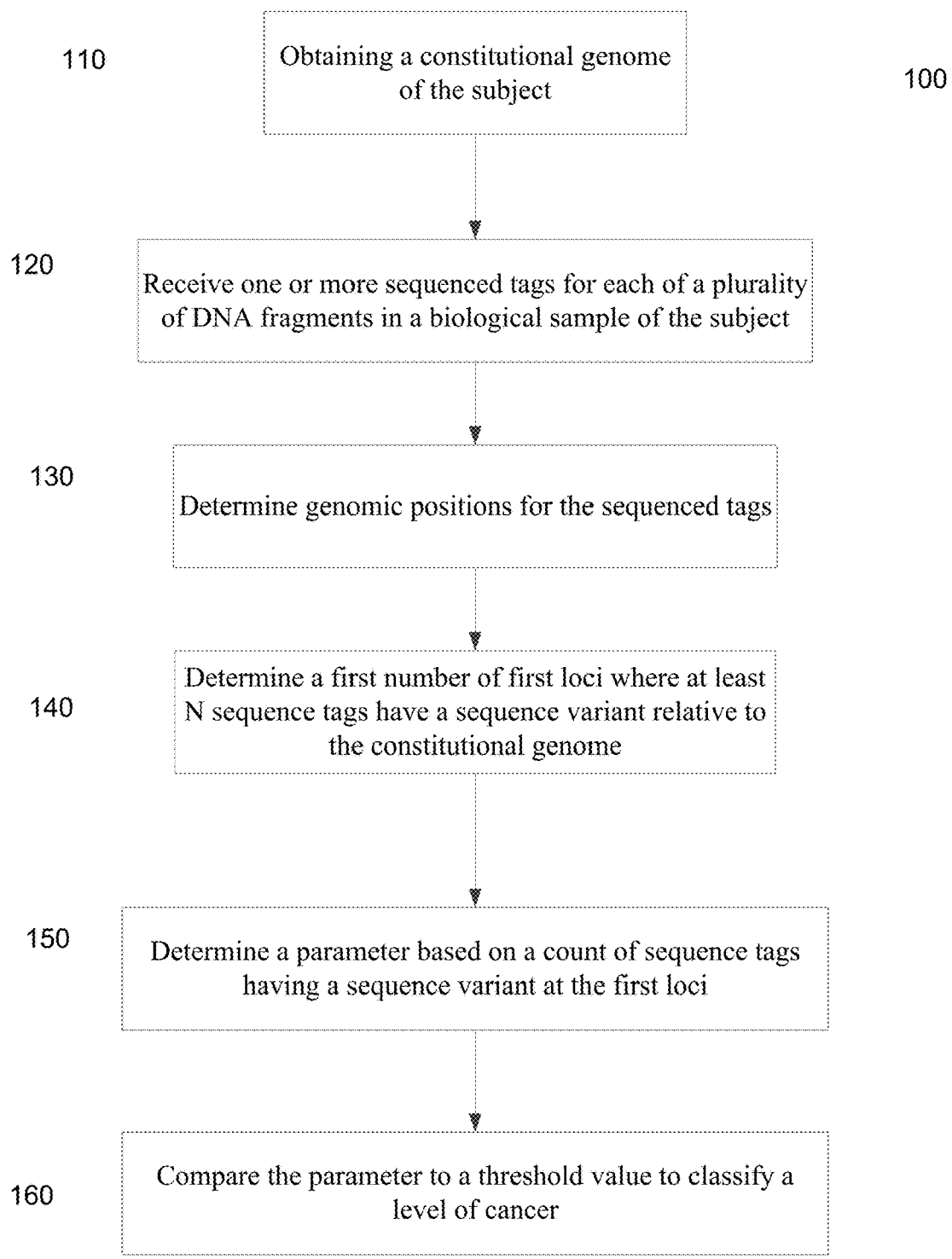
FIG. 1 is a flowchart of a method 100 for detecting cancer or premalignant change in a subject according to embodiments of the present invention.

As used herein, the term "locus" or its plural form "loci" is a location or address of any length of nucleotides (or base pairs) which may have a variation across genomes. A "bin" is a region of predetermined length in a genome. A plurality of bins may have a same first length (resolution), while a different plurality can have a same second length. In one embodiment, the bins do not overlap each other.

The term "random sequencing" as used herein refers to sequencing whereby the nucleic acid fragments sequenced have not been specifically identified or predetermined before the sequencing procedure. Sequence-specific primers to target specific gene loci are not required. The term "universal sequencing" refers to sequencing where sequencing can start on any fragment. In one embodiment, adapters are added to the end of a fragment, and the primers for sequencing attached to the adapters. Thus, any fragment can be sequenced with the same primer, and thus the sequencing can be random.

The term "sequence tag" (also referred to as sequence read) as used herein refers to string of nucleotides sequenced from any part or all of a nucleic acid molecule. For example, a sequenced tag may be a short string of nucleotides (e.g., ~30) sequenced from a nucleic acid fragment, a short string of nucleotides at both ends of a nucleic acid fragment, or the sequencing of the entire nucleic acid fragment that exists in the biological sample. A nucleic acid fragment is any part of a larger nucleic acid molecule. A fragment (e.g. a gene) may exist separately (i.e. not connected) to the other parts of the larger nucleic acid molecule.

The term "constitutional genome" (also referred to a CG) is composed of the consensus nucleotides at loci within the genome, and thus can be considered a consensus sequence. The CG can cover the entire genome of the subject (e.g., the human genome), or just parts of the genome. The constitutional genome (CG) can be obtained from DNA of cells as well as cell-free DNA (e.g., as can be found in plasma). Ideally, the consensus nucleotides should indicate that a locus is homozygous for one allele or heterozygous for two alleles. A heterozygous locus typically contains two alleles which are members of a genetic polymorphism. As an example, the criteria for determining whether a locus is heterozygous can be a threshold of two alleles each appearing in at least a predetermined percentage (e.g., 30% or 40%) of reads aligned to the locus. If one nucleotide appears at a sufficient percentage (e.g., 70% or greater) then the locus can be determined to be homozygous in the CG. Although the genome of one healthy cell can differ from the genome of another healthy cell due to random mutations spontaneously occurring during cell division, the CG should not vary when such a consensus is used. Some cells can have genomes with genomic rearrangements, e.g., B and T lymphocytes, such as involving antibody and T cell receptor genes. Such large scale differences would still be a relatively small population of the total nucleated cell population in blood, and thus such rearrangements would not affect the determination of the constitutional genome with sufficient sampling (e.g., sequencing depth) of blood cells. Other cell types, including buccal cells, skin cells, hair follicles, or biopsies of various normal body tissues, can also serve as sources of CG.

The term "constitutional DNA" refers to any source of DNA that is reflective of the genetic makeup with which a subject is born. For a subject, examples of "constitutional samples", from which constitutional DNA can be obtained, include healthy blood cell DNA, buccal cell DNA and hair root DNA. The DNA from these healthy cells defines the CG of the subject. The cells can be identified as healthy in a variety of ways, e.g., when a person is known to not have cancer or the sample can be obtained from tissue that is not likely to contain cancerous or premalignant cells (e.g., hair root DNA when liver cancer is suspected). As another example, a plasma sample may be obtained when a patient is cancer-free, and the determined constitutional DNA compared against results from a subsequent plasma sample (e.g., a year or more later). In another embodiment, a single biologic sample containing <50% of tumor DNA can be used for deducing the constitutional genome and the tumor-associated genetic alterations. In such a sample, the concentrations of tumor-associated single nucleotide mutations would be lower than those of each allele of heterozygous SNPs in the CG. Such a sample can be the same as the biological sample used to determine a sample genome, described below.

The term "biological sample" as used herein refers to any sample that is taken from a subject (e.g., a human, a person with cancer, a person suspected of having cancer, or other organisms) and contains one or more cell-free nucleic acid molecule(s) of interest. A biological sample can include cell-free DNA, some of which can have originated from healthy cells and some from tumor cells. For example, tumor DNA can be found in blood or other fluids, e.g., urine, pleural fluid, ascitic fluid, peritoneal fluid, saliva, tears or cerebrospinal fluid. A non-fluid example is a stool sample, which may be mixed with diarrheal fluid. For some of such samples, the biological sample can be obtained non-invasively. In some embodiments, the biological sample can be used as a constitutional sample.

The term "sample genome" (also referred to as SG) is a collection of sequence reads that have been aligned to locations of a genome (e.g., a human genome). The sample genome (SG) is not a consensus sequence, but includes nucleotides that may appear in only a sufficient number of reads (e.g., at least 2 or 3, or higher cutoff values). If an allele appears a sufficient number of times and it is not part of the CG (i.e., not part of the consensus sequence), then that allele can indicate a "single nucleotide mutation" (also referred to as an SNM). Other types of mutations can also be detected using the current invention, e.g. mutations involving two or more nucleotides, (such as affect the number of tandem repeat units in a microsatellite or simple tandem repeat polymorphism), chromosomal translocation (which can be intrachromosomal or interchromosomal) and sequence inversion.

The term "reference genome" (also referred to as RG) refers to a haploid or diploid genome to which sequence reads from the biological sample and the constitutional sample can be aligned and compared. For a haploid genome, there is only one nucleotide at each locus. For a diploid genome, heterozygous loci can be identified, with such a locus having two alleles, where either allele can allow a match for alignment to the locus.

The term "level of cancer" can refer to whether cancer exists, a stage of a cancer, a size of tumor, and/or other measure of a severity of a cancer. The level of cancer could be a number or other characters. The level could be zero. The level of cancer also includes premalignant or precancerous conditions (states) associated with mutations or a number of mutations. The level of cancer can be used in various ways. For example, screening can check if cancer is present in someone who is not known previously to have cancer. Assessment can investigate someone who has been diagnosed with cancer. Detection can mean 'screening' or can mean checking if someone, with suggestive features of cancer (e.g. symptoms or other positive tests), has cancer.

DETAILED DESCRIPTION

Embodiments are provided for the detection of cancer by the analysis of a biological sample (e.g., a blood plasma/serum sample) that is not taken directly from a tumor and includes cell-free nucleic acids. The cell-free nucleic acids can originate for various types of tissue throughout the body. In this manner, a broad analysis for the detection of various cancers can be performed.

Genetic aberrations (including single nucleotide mutations, deletions, amplifications, and rearrangements) accumulate in the tumor cells during the development of cancers. In embodiments, massively parallel sequencing can be used to detect and quantify the single nucleotide mutations (SNMs), also called single nucleotide variations (SNVs), in body fluids (e.g. plasma, serum, saliva, ascitic fluid, pleural fluid and cerebrospinal fluid) so as to detect and monitor cancers. A quantification of the number of SNMs (or other types of mutations) can provide a mechanism for identifying early stages of cancer as part of screening tests. In various implementations, care is taken to distinguish sequencing errors and to distinguish spontaneous mutations occurring in healthy cells (e.g., by requiring multiple SNMs to be identified at a particular locus, e.g., at least 3, 4, or 5).

Some embodiments also provide noninvasive methods for the analysis of tumor heterogeneity, which can involve cells within the same tumor (i.e. intratumoral heterogeneity) or cells from different tumors (from either the same site or from different sites) within a body. For example, one can noninvasively analyze the clonal structure of such tumor heterogeneity, including an estimation of the relative tumor cell mass containing each mutation. Mutations that are present in higher relative concentrations are present in a larger number of malignant cells in the body, e.g., cells that have occurred earlier on during the tumorigenic process relative to other malignant cells still in the body (Welch J S et al. Cell 2012; 150: 264-278). Such mutations, due to their higher relative abundance, are expected to exhibit a higher diagnostic sensitivity for detecting cancer DNA than those with lower relative abundance. A serial monitoring of the change of the relative abundance of mutations would allow one to noninvasively monitor the change in the clonal architecture of tumors, either spontaneously as the disease progresses, or in response to treatment. Such information would be of use in assessing prognosis or in the early detection of tumor resistance to treatment.

I. INTRODUCTION

Mutations can occur during cell division because of errors in DNA replication and/or DNA repair. One type of such mutations involve the alteration of single nucleotides, which can involve multiple sequences from different parts of the genome. Cancers are generally believed to be due to the clonal expansion of a single cancer cell which has acquired growth advantage. This clonal expansion would lead to the accumulation of mutations (e.g. single nucleotide mutations) in all the cancer cells originating from the ancestral cancer cell. These progeny tumor cells would share a set of mutations (e.g. single nucleotide mutations). As described herein, cancer-associated single nucleotide mutations are detectable in the plasma/serum of cancer patients.

Some embodiments can effectively screen for all mutations in a biological sample (e.g., the plasma or serum). As the number of mutations are not fixed (hundreds, thousands, or millions of cancer-associated mutations from different subpopulations of tumor cells can be detected), embodiments can provide a better sensitivity than techniques that detect specific mutations. The number of mutations can be used to detect cancer.

To provide such a screening of many or all mutations, embodiments can perform a search (e.g., a random search) for genetic variations in a biological sample (e.g., bodily fluids, including plasma and serum), which could contain tumor-derived DNA. The use of a sample, such as plasma, obviates the need to perform an invasive biopsy of the tumor or cancer. Also, as the screening can cover all or large regions of the genome, the screening is not limited to any enumerable and known mutations, but can use the existence of any mutation. Moreover, since the number of mutations is summed across all or large regions of the genome, a higher sensitivity can be obtained.

However, there are polymorphic sites, including single nucleotide polymorphisms (SNPs), in the human genome, which should not be counted in the mutations. Embodiments can ascertain whether genetic variations that have been detected are likely to be cancer-associated mutations or are polymorphisms in the genome. For example, as part of determining between cancer-associated mutations and polymorphisms in the genome, embodiments can determine a constitutional genome, which can include polymorphisms. The polymorphisms of the constitutional genome (CG) can be confined to polymorphisms that are exhibited with a sufficiently high percentage (e.g., 30-40%) in the sequencing data.

The sequences obtained from the biological sample can then be aligned to the constitutional genome and variations that are single nucleotide mutations (SNMs), or other types of mutations, identified. These SNMs would be variations that are not included in the known polymorphisms, and thus can be labeled as cancer-associated, and not part of the constitutional genome. A healthy person may have a certain number of SNMs due to random mutations among healthy cells, e.g., created during cell division, but a person with cancer would have more.

For example, for a person with cancer, the number of SNMs detectable in a bodily fluid would be higher than the polymorphisms present in the constitutional genome of the same person. A comparison can be made between the amounts of variations detected in a bodily fluid sample containing tumor-derived DNA and a DNA sample containing mostly constitutional DNA. In one embodiment, the term 'mostly' would mean more than 90%. In another preferred embodiment, the term 'mostly' would mean more than 95, 97%, 98%, or 99%. When the amount of variations in the bodily fluid exceeds that of the sample with mostly constitutional DNA, there is an increased likelihood that the bodily fluid might contain tumor-derived DNA.

One method that could be used to randomly search for variations in DNA samples is random or shotgun sequencing (e.g., using massively parallel sequencing). Any massively parallel sequencing platform may be used, including a sequencing-by-ligation platform (e.g. the Life Technologies SOLiD platform), the Ion Torrent/Ion Proton, semiconductor sequencing, Roche 454, single molecular sequencing platforms (e.g. Helicos, Pacific Biosciences and nanopore). Yet, it is known that sequencing errors can occur and may be misinterpreted as a variation in the constitutional DNA or as mutations derived from tumor DNA. Thus, to improve the specificity of our proposed approach, the probability of the sequencing error or other components of analytical errors can be accounted for, e.g., by using an appropriate sequencing depth along with requiring at least a specified number (e.g., 2 or 3) of detected alleles at a locus for it to be counted as an SNM.

As described herein, embodiments can provide evidence for the presence of tumor-derived DNA in a biological sample (e.g., a bodily fluid) when the amount of randomly detected genetic variations present in the sample exceeds that expected for constitutional DNA and variations that may be inadvertently detected due to analytical errors (e.g., sequencing errors). The information could be used for the screening, diagnosis, prognostication and monitoring of cancers. In the following sections, we describe analytical steps that can be used for the detection of single nucleotide mutations in plasma/serum or other samples (e.g., bodily fluids). Bodily fluids could include plasma, serum, cerebrospinal fluid, pleural fluid, ascitic fluid, nipple discharge, saliva, bronchoalveolar lavage fluid, sputum, tears, sweat and urine. In addition to bodily fluids, the technology can also be applied to stools sample, as the latter has been shown to contain tumor DNA from colorectal cancer (Berger B M, Ahlquist D A. Pathology 2012; 44: 80-88).

II. GENERAL SCREENING METHOD

FIG. 1 is a flowchart of a method 100 for detecting cancer or premalignant change in a subject according to embodiments of the present invention. Embodiments can analyze cell-free DNA in a biological sample from the subject to detect variations in the cell-free DNA likely resulting from a tumor. The analysis can use a constitutional genome of the subject to account for polymorphisms that are part of healthy cells, and can account for sequencing errors. Method 100 and any of the methods described herein may be totally or partially performed with a computer system including one or more processors.

In step 110, a constitutional genome of the subject is obtained. The constitutional genome (CG) can be determined from the constitutional DNA of the tested subject. In various embodiments, the CG can be read from memory or actively determined, e.g., by analyzing sequence reads of constitutional DNA, which may be in cells from the sample that includes the cell-free DNA. For example, when a non-hematological malignancy is suspected, blood cells can be analyzed to determine the constitutional DNA of the subject.

In various implementations, the analysis of the constitutional DNA could be performed using massively parallel sequencing, array-based hybridization, probe-based in-solution hybridization, ligation-based assays, primer extension reaction assays, and mass spectrometry. In one embodiment, the CG can be determined at one time point in a subject's life, e.g., at birth or even in the prenatal period (which could be done using fetal cells or via cell-free DNA fragment, see U.S. Publication 2011/0105353), and then be referred to when bodily fluids or other samples are obtained at other times of the subject's life. Thus, the CG may simply be read from computer memory. The constitutional genome may be read out as a list of loci where the constitutional genome differs from a reference genome.

In step 120, one or more sequence tags are received for each of a plurality of DNA fragments in a biological sample of the subject, where the biological sample includes cell-free DNA. In one embodiment, the one or more sequence tags are generated from a random sequencing of DNA fragments in the biological sample. More than one sequence tag may be obtained when paired-end sequencing is performed. One tag would correspond to each end of the DNA fragment.

The cell-free DNA in the sample (e.g., plasma, serum or other body fluid) can be analyzed to search for genetic variations. The cell-free DNA can be analyzed using the same analytical platform as that has been used to analyze the constitutional DNA. Alternatively, a different analytical platform could be used. For example, the cell-free DNA sample can be sequenced using massively parallel sequencing or parts of the genome could be captured or enriched before massively parallel sequencing. If enrichment is used, one could, for example, use solution-phase or solid-phase capture of selected parts of the genome. Then, massively parallel sequencing can be carried out on the captured DNA.

In step 130, genomic positions for the sequence tags are determined. In one embodiment, the sequence tags are aligned to a reference genome, which is obtained from one or more other subjects. In another embodiment, the genomic sequence tags are aligned to the constitutional genome of the tested subject. The alignment can be performed using techniques known to one skilled in the art, e.g., using Basic Local Alignment Search Tool (BLAST).

In step 140, a first number of loci are determined where at least N sequence tags have a sequence variant relative to the constitutional genome (CG). N is equal to or greater than two. As discussed in more detail below, sequencing errors as well as somatic mutations occurring randomly in cells (e.g., due to cell division) can be removed by having N equal 2, 3, 4, 5, or higher. The loci that satisfy one or more specified criteria can be identified as a mutation (variant) or mutation loci (variant loci), whereas a locus having a variant but not satisfying the one or more criteria (e.g., as just one variant sequence tag) is referred to as a potential or putative mutation. The sequence variant could be for just one nucleotide or multiple nucleotides.

N may be determined as percentage of total tags for a locus, as opposed to an absolute value. For example, a variant locus can be identified when the fractional concentration of tumor DNA inferred from the variant reads is determined to be equal to or greater than 10% (or some other percentage). In other words, when the locus is covered by 200 sequence reads, a criterion of at least 10 sequence reads showing the variant allele can be required to define the variant as a mutation. The 10 sequence reads of the variant allele and 190 reads of the wildtype allele would give an fractional concentration of tumor DNA of 10% (2×10/(10+190)).

In one embodiment, the sequence tags (collectively referred to as the sample genome) can be compared directly to the CG to determine the variants. In another embodiment, the sample genome (SG) is compared to the CG via a reference genome (RG) to determine the variants. For example, both the CG and SG can be compared to the RG to determine respective numbers (e.g., sets) of loci exhibiting variants, and then a difference can be taken to obtain the first number of loci. The first number can simply be obtained as a number or may correspond to a specific set of loci, which may then be analyzed further to determine a parameter from the sequence tags at the first loci.

In one implementation, sequencing results of constitutional DNA and plasma DNA are compared to determine if a single nucleotide mutation is present in the plasma DNA. The regions at which the constitutional DNA is homozygous can be analyzed. For illustration purposes, assume the genotype of a particular locus is homozygous in the constitutional DNA and is AA. Then in the plasma, the presence of an allele other than A would indicate the potential presence of a single nucleotide mutation (SNM) at the particular locus. The loci indicating the potential presence of an SNM can form the first number of loci in step 140.

In one embodiment, it could be useful to target parts of the genome that are known to be particularly prone to mutation in a particular cancer type or in a particular subset of the population. Of relevance to the latter aspect, embodiments can look for types of mutations that are particularly prevalent in a specific population group, e.g. mutations that are especially common in subjects who are carriers of hepatitis B virus (for liver cancer) or human papillomavirus (for cervical cancer) or who have genetic predisposition to somatic mutations or subjects with germline mutations in a DNA mismatch repair gene. The technology would also be useful to screen for mutations in ovarian and breast cancers in subjects with BRCA1 or BRCA2 mutations. The technology would similarly be useful to screen for mutations in colorectal cancer in subjects with APC mutations.

In step 150, a parameter is determined based on a count of sequence tags having a sequence variant at the first loci. In one example, the parameter is the first number of loci where at least N DNA fragments have a sequence variant at a locus relative to the constitutional genome. Thus, the count can be used simply to ensure that a locus has more than N copies of a particular variant identified before being included in the first number. In another embodiment, the parameter can be or include the total number of sequence tags having a sequence variant relative to the constitutional genome at the first loci.

In step 160, the parameter for the subject is compared to a threshold value (e.g., derived from one or more other subjects) to determine a classification of a level of cancer in the subject. Examples of a level of cancer includes whether the subject has cancer or a premalignant condition, or an increased likelihood of developing cancer. In one embodiment, the threshold value may be determined from a previously obtained sample from the subject.

In another embodiment, the one or more other subjects may be determined to not have cancer or a low risk of cancer. Thus, threshold value may be a normal value, a normal range, or indicate a statistically significant deviation from a normal value or range. For example, the number of mutations relative to the CG of a specific subject, detectable in the plasma of subjects without a cancer or with a low risk of cancer, can be used as the normal range to determine if the number of mutations detected in the tested subject is normal. In another embodiment, the other subjects could be known to have cancer, and thus a similar number of mutations can indicate cancer.

In one implementation, the other subjects can be selected to have clinical characteristics that are matched to those of the test subject, e.g. sex, age, diet, smoking habit, drug history, prior disease, family history, genotypes of selected genomic loci, status for viral infections (e.g. hepatitis B or C virus or human papillomavirus or human immunodeficiency virus or Epstein-Barr virus infection) or infections with other infectious agents (such as bacteria (e.g. *Helicobacter pylori*) and parasites (e.g. *Clonorchis sinensis*), etc. For example, subjects who are carriers of hepatitis B or C virus have an increased risk of developing hepatocellular carcinoma. Thus, test subjects who have a similar number or pattern of mutations as a carrier of hepatitis B or C can be considered to have an increased risk of developing hepatocellular carcinoma. On the other hand, a hepatitis B or C patient who exhibits more mutations than another hepatitis patient can properly be identified as having a higher classification of a level of cancer, since the proper baseline (i.e. relative to another hepatitis patient) is used. Similarly, subjects who are carriers of human papillomavirus infection have increased risk for cervical cancer, and head and neck cancer. Infection with the Epstein-Barr virus has been associated with nasopharyngeal carcinoma, gastric cancer, Hodgkin's lymphoma and non-Hodgkin's lymphoma. Infection with *Helicobacter pylori* has been associated with gastric cancer. Infection with *Clonorchis sinensis* has been associated with cholangiocarcinoma.

The monitoring of the changes of the number of mutations at different time points can be used for monitoring of the progress of the cancer and the treatment response. Such monitoring can also be used to document the progress of a premalignant condition or change in the risk that a subject would develop cancer.

The amount of sequence tags showing variations can also be used to monitor. For example, a fractional concentration of variant reads at a locus can be used. In one embodiment, an increase in the fractional concentrations of tumor-associated genetic aberrations in the samples during serial monitoring can signify the progression of the disease or imminent relapse. Similarly, a decrease in the fractional concentrations of tumor-associated genetic aberrations in the samples during serial monitoring can signify response to treatment and/or remission and/or good prognosis.

III. DETERMINING GENOMES

The various genomes discussed above are explained in more detail below. For example, the reference genome, constitutional genome, and the sample genome are discussed.

A. Reference Genome

The reference genome (RG) refers to a haploid or diploid genome of a subject or consensus of a population. The reference genome is known and thus can be used to compare sequencing reads from new patients. The sequence reads from a sample of a patient can be aligned and compared to identify variations in the reads from the RG. For a haploid genome, there is only one nucleotide at each locus, and thus each locus can be considered hemizygous. For a diploid genome, heterozygous loci can be identified, with such a locus having two alleles, where either allele can allow a match for alignment to the locus.

A reference genome can be the same among a population of subjects. This same reference genome can be used for healthy subjects to determine the appropriate threshold to be used for classifying the patient (e.g., having cancer or not). However, different reference genomes can be used for different populations, e.g., for different ethnicities or even for different families.

B. Constitutional Genome

The constitutional genome (CG) for a subject (e.g., a human or other diploid organism) refers to a diploid genome of the subject. The CG can specify heterozygous loci where a first allele is from a first haplotype and a different second allele is from a second haplotype. Note that the structures of two haplotypes that cover two heterozygous loci need not be known, i.e., which allele on one heterozygous locus is on the same haplotype as an allele of another heterozygous locus need not be known. Just the existence of the two alleles at each heterozygous locus can be sufficient.

The CG can differ from the RG due to polymorphisms. For example, a locus on the RG can be homozygous for T, but the CG is heterozygous for T/A. Thus, the CG would exhibit a variation at this locus. The CG can also be different from the RG due to inherited mutations (e.g., that run in families) or de novo mutations (that occur in a fetus, but which are not present in its parents). The inherited mutation is typically called 'germline mutation'. Some of such mutations are associated with predisposition to cancer, such as a BRCA1 mutation that runs in a family. Such mutations are different from 'somatic mutations' that can occur due to cell division during one's lifetime and can push a cell and its progeny on the way to become a cancer.

A goal of determining the CG is to remove such germline mutations and de novo mutations from the mutations of the sample genome (SG) in order to identify the somatic mutations. The amount of somatic mutations in the SG can then be used to assess the likelihood of cancer in the subject. These somatic mutations can be further filtered to remove sequencing errors, and potentially to remove somatic mutations that occur rarely (e.g., only one read showing a variant), as such somatic mutations are not likely related to cancer.

In one embodiment, a CG can be determined using cells (buffy coat DNA). However, the CG can also be determined from cell-free DNA (e.g. plasma or serum) as well. For a sample type in which most of the cells are non-malignant, e.g. the buffy coat from a healthy subject, then the majority or consensus genome is the CG. For the CG, each genomic locus consists of the DNA sequence possessed by the majority of cells in the sampled tissue. The sequencing depth should be sufficient to elucidate heterozygous sites within the constitutional genome.

As another example, plasma can be used as the constitutional sample to determine the CG. For example, for cases in which the tumor DNA in plasma is less than 50% and an SNM is in a heterozygous state, e.g., the mutation is the addition of a new allele, then the new allele can have a concentration of less than 25%. Whereas, the concentration of the heterozygous alleles of SNPs in the CG should amount to approximately 50%. Thus, a distinction can be made between a somatic mutation and a polymorphism of the CG. In one implementation, a suitable cutoff can be between 30-40% for determining a somatic mutation from a polymorphism when using plasma, or other mixtures with significant tumor concentration. A measurement of tumor DNA concentration can be useful to ensure that the tumor DNA in plasma is less than 50%. Examples of determining a tumor DNA concentration are described herein.

C. Sample Genome

The sample genome (SG) is not simply a haploid or diploid genome as is the case for the RG and CG. The SG is a collection of reads from the sample, and can include: reads from constitutional DNA that correspond to the CG, reads from tumor DNA, reads from healthy cells that show random mutations relative to the CG (e.g., due to mutations resulting from cell division), and sequencing errors. Various parameters can be used to control exactly which reads are included in the SG. For example, requiring an allele to show up in at least 5 reads can decrease the sequencing errors present in the SG, as well as decrease the reads due to random mutations.

As an example, assume the subject is healthy, i.e., does not have cancer. For illustration purposes, the DNA from 1000 cells is in 1 ml of plasma (i.e. 1000 genome-equivalents of DNA) obtained from this subject. Plasma DNA typically consists of DNA fragments of about 150 bp. As the human genome is $3 \times 10^9$ bp, there would be about $2 \times 10^7$ DNA fragments per haploid genome. As the human genome is diploid, there would be about $4 \times 10^7$ DNA fragments per ml of plasma.

As millions to billions of cells are releasing their DNA in the plasma per unit time and fragments from these cells would mix together during circulation, the $4 \times 10^7$ DNA fragments could have come from $4 \times 10^7$ different cells. If these cells do not bear a recent (as opposed to distant, e.g., the original zygote) clonal relationship to each other (i.e. that they do not share a recent ancestral cell), then it is statistically likely that no mutation will be seen more than once amongst these fragments.

On the other hand, if amongst the 1000 genome-equivalents per ml of plasma DNA, there is a certain percentage of cells that share a recent ancestral cell (i.e., they are related to each other clonally), then one could see the mutations from this clone to be preferentially represented in the plasma DNA (e.g. exhibiting a clonal mutational profile in plasma). Such clonally related cells could be cancer cells, or cells that are on their way to become a cancer but not yet there (i.e. pre-neoplastic). Thus, requiring a mutation to show up more than once can remove this natural variance in the "mutations" identified in the sample, which can leave more mutations related to cancer cells or pre-neoplastic cells, thereby allowing detection, especially early detection of cancer or precancerous conditions.

In one approximation, it has been stated that on average, one mutation will be accumulated in the genome following every cell division. Previous work has shown that most of the plasma DNA is from hematopoietic cells (Lui Y Y et al. Clin Chem 2002: 48: 421-427). It has been estimated that hematopoietic stem cells replicate once every 25-50 weeks (Catlin S N, et al. Blood 2011; 117: 4460-4466). Thus, as a simplistic approximation, a healthy 40-year-old subject would have accumulated some 40 to 80 mutations per hematopoietic stem cell.

If there are 1000 genome-equivalents per ml in this person's plasma, and if each of these cells is derived from a different hematopoietic stem cell, then 40,000 to 80,000 mutations might be expected amongst the $4 \times 10^{10}$ DNA fragments (i.e. $4 \times 10^7$ DNA fragments per genome, and 1000 genome-equivalents per ml of plasma). However, as each mutation would be seen once, each mutation can still be below a detection limit (e.g., if cutoff value N is greater than 1), and thus these mutations can be filtered out, thereby allowing the analysis to focus on mutations that are more likely to result from cancerous conditions. The cutoff value can be any value (integer or non-integer) greater than one, and may be dynamic for different loci and regions. The sequencing depth and fractional concentration of tumor DNA can also affect the sensitivity of detecting mutations (e.g., percentage of mutations detectable) from cancer cells or pre-neoplastic cells.

IV. COMPARING SG DIRECTLY TO CG

Some embodiments can identify nucleotide positions that the CG is homozygous, but where a minority species (i.e. the tumor DNA) in the SG is heterozygous. When sequencing a position in high depth (e.g., over 50-fold coverage), one can detect if there are one or two alleles at that position in the DNA mixture of healthy and cancer cells. When there are two alleles detected, either (1) the CG is heterozygous or (2)

the CG is homozygous but the SG is heterozygous. These two scenarios can be differentiated by looking at the relative counts of the major and the minor alleles. In the former scenario, the two alleles would have similar numbers of counts; but for the latter scenario, there would be a large difference in their numbers of counts. This comparison of the relative allele counts of the reads from the test sample is one embodiment for comparing sequence tags to the constitutional genome. The first loci of method 100 can be determined as loci where the number of alleles is below an upper threshold (threshold corresponding to a polymorphism in the CG) and above a lower threshold (threshold corresponding to errors and somatic mutations occurring at a sufficiently low rate to not be associated with a cancerous condition). Thus, the constitutional genome and the first loci can be determined at the same time.

In another embodiment, a process for identifying mutations can determine the CG first, and then determine loci having a sufficient number of mutations relative to the CG. The CG can be determined from a constitutional sample that is different from the test sample.

Figure 2:
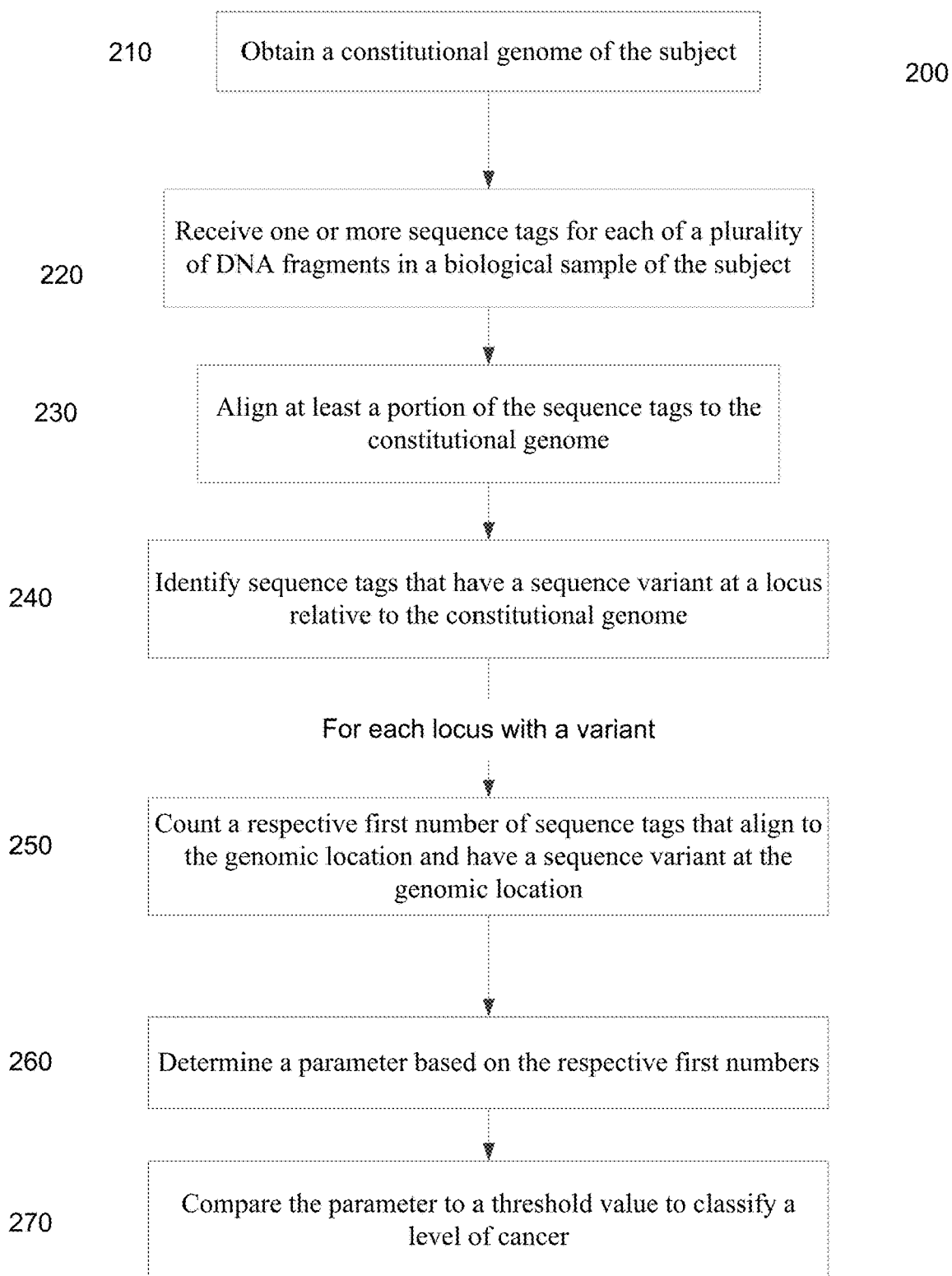
FIG. 2 shows a flowchart of a method comparing the sample genome (SG) directly to the constitutional genome (CG) according to embodiments of the present invention.

FIG. 2 shows a flowchart of a method 200 comparing the sample genome (SG) directly to the constitutional genome (CG) according to embodiments of the present invention. At block 210, a constitutional genome of the subject is obtained. The constitutional genome can be obtained, for example, from a sample taken previously in time or a constitutional sample that is obtained and analyzed just before method 200 is implemented.

At block 220, one or more sequence tags are received for each of a plurality of DNA fragments in a biological sample of the subject. The sequencing may be performed using various techniques, as mentioned herein. The sequence tags are a measurement of what the sequence of a fragment is believed to be. But, one or more bases of a sequence tag may be in error.

At block 230, at least a portion of the sequence tags are aligned to the constitutional genome. The alignment can account for the CG being heterozygous at various loci. The alignment would not require an exact match so that variants could be detected.

At block 240, sequence tags that have a sequence variant at a locus relative to the constitutional genome are identified. It is possible that a sequence tag could have more than one variant. The variants for each locus and for each sequence tag can be tracked. A variant could be any allele that is not in the CG. For example, the CG could be heterozygous for A/T and the variant could be G or C.

At block 250, for each locus with a variant, a computer system can count a respective first number of sequence tags that align to the locus and have a sequence variant at the locus. Thus, each locus can have an associated count of the number of variants seen at the locus. Typically, fewer variants will be seen at a locus compared to sequence tags that correspond to the CG, e.g., due to the tumor DNA concentration being less than 50%. However, some samples may have a concentration of tumor DNA that is greater than 50%.

At block 260, a parameter is determined based on the respective first numbers. In one embodiment, if a respective number is greater than a cutoff value (e.g., greater than two), then the respective number can be added to a sum, which is the parameter or is used to determine the parameter. In another embodiment, the number of loci having a respective number greater than the cutoff value is used as the parameter.

At block 270, the parameter is compared to a threshold value to classify a level of cancer. As described above, the threshold value may be determined from the analysis of samples from other subjects. Depending on the healthy or cancer state of these other subjects, the classification can be determined. For example, if the other subjects had stage 4 cancer, then if the current parameter was close (e.g., within a specific range) to the value of the parameter obtained from the other subjects, then the current subject might be classified as having stage 4 cancer. However, if the parameter is exceeds the threshold (i.e., greater than or less, depending on how the parameter is defined), then the classification can be identified as being less than stage 4. A similar analysis can be made when the other subjects do not have cancer.

Multiple thresholds may be used to determine the classification, where each threshold is determined from a different set of subjects. Each set of subjects may have a common level of cancer. Thus, the current parameter may be compared to the values for each set of subjects, which can provide a match to one of the sets or provide a range. For example, the parameter might be about equal to the parameter obtained for subjects that are precancerous or at stage 2. As another example, the current parameter can fall in a range that can possibly match to several different levels of cancer. Thus, the classification can include more than one level of cancer.

V. USING REFERENCE GENOME

The genomic sequences of both the constitutional DNA and the DNA from the biological sample can be compared to the human reference genome. When there are more changes in the plasma sample than the constitutional DNA as compared with the reference genome, then there is a higher probability for cancer. In one embodiment, the homozygous loci in the reference genome are studied. The amounts of heterozygous loci in both the constitutional DNA and DNA from the biological sample are compared. When the amount of heterozygous sites detected from the DNA of the biological sample exceeds that of the constitutional DNA, there is a higher probability of cancer.

The analysis could also be limited to loci that are homozygous in the CG. SNMs can be defined for heterozygous loci as well, but this would generally require the generation of a third variant. In other words, if the heterozygous locus is A/T, a new variant would be either C or G. Identifying SNMs for homozygous loci is generally easier.

The degree to which an increase in the amount of heterozygous loci in the biological sample DNA relative to the constitutional DNA can be suggestive of cancer or a premalignant state when compared to the rate of change seen in healthy subjects. For example, if the degree of increase in such sites exceeds that observed in healthy subjects by a certain threshold, one can consider the data to be suggestive of cancer or a premalignant state. In one embodiment, the distribution of mutations in subjects without cancer is ascertained and a threshold can be taken as a certain number of standard deviations (e.g., 2 or 3 standard deviations).

One embodiment can require at least a specified number of variants at a locus before that locus is counted. Another embodiment provides a test even for the data based on seeing a change once. For example, when the total number of variations (errors+genuine mutations or polymorphisms) seen in plasma is statistically significantly higher than that in the constitutional DNA, then there is evidence for cancer.

FIG. 3 shows a flowchart of a method 300 comparing the sample genome (SG) to the constitutional genome (CG) using the reference genome (RG) according to embodiments of the present invention. Method 300 assumes that the RG is already obtained, and that the sequence tags for the biological sample have already been received.

At block 310, at least a portion of the sequence tags are aligned to the reference genome. The alignment can allow mismatches as variations are being detected. The reference genome can be from a similar population as the subject. The aligned sequence tags effectively comprise the sample genome (SG)

At block 320, a first number (A) of potential variants, e.g., single nucleotide mutations (SNMs), are identified. The potential SNMs are loci where a sequence tag of the SG shows a nucleotide that is different from the RG. Other criteria may be used, e.g., the number of sequence tags showing a variation must be greater than a cutoff value and whether a locus is homozygous in the RG. The set of potential SNMs may be represented as set A when specific loci are identified and tracked by storing the loci in memory. The specific loci may be determined or simply a number of such SNMs can be determined.

At block 330, a constitutional genome is determined by aligning sequence tags obtained by sequencing DNA fragments from a constitutional sample to a reference genome. This step could have been performed at any time previously and using a constitutional sample obtained at any time previously. The CG could simply be read from memory, where the aligning was previously done. In one embodiment, the constitutional sample could be blood cells.

At block 340, a second number (B) of loci where an aligned sequence tag of the CG has a variant (e.g., an SNM) at a locus relative to the reference genome are identified. If a set of loci is specifically tracked, then B can represent the set, as opposed to just a number.

At block 350, set B is subtracted from set A to identify variants (SNMs) that are present in the sample genome but not in CG. In one embodiment, the set of SNMs can be limited to nucleotide positions that the CG is homozygous. To achieve this filtering, specific loci where the CG is homozygous can be identified in set C. In another embodiment, a locus is not counted in the first number A or the second number B, if the CG is not homozygous at the locus. In another embodiment, any known polymorphism (e.g. by virtue of its presence in a SNP database) can be filtered out.

In one embodiment, the subtraction in block 350 can simply be a subtraction of numbers, and thus specific potential SNMs are not removed, but simply a value is subtracted. In another embodiment, the subtraction takes a difference between set A and set B (e.g., where set B is a subset of set A) to identify the specific SNMs that are not in set B. In logical values, this can be expressed as [A AND NOT(B)]. The resulting set of identified variants can be labeled C. The parameter can be determined as the number C or determined from the set C.

In some embodiments, the nature of the mutations can be taken into consideration and different weighting attributed to different classes of mutations. For example, mutations that are commonly associated with cancer can be attributed a higher weighting (also called an importance value when referring to relative weightings of loci). Such mutations can be found in databases of tumor-associated mutations, e.g., the Catalogue of Somatic Mutations in Cancer (COSMIC) (www.sanger.ac.uk/genetics/CGP/cosmic/). As another example, mutations associated with non-synonymous changes can be attributed a higher weighting.

Thus, the first number A could be determined as a weighted sum, where the count of tags showing a variant at one locus may have a different weighting than the count of tags at another locus. The first number A can reflect this weighted sum. A similar calculation can be performed B, and thus the number C and the parameter can reflect this weighting. In another embodiment, the weightings are accounted for when a set C of specific loci is determined. For example, a weighted sum can be determined for the counts for the loci of set C. Such weights can be used for other methods described herein.

Accordingly, the parameter that is compared to a threshold to determine the classification of a level of cancer can be the number of loci exhibiting a variation for the SG and the CG relative to the RG. In other embodiments, the total number of DNA fragments (as counted via the sequence tags) showing a variation can be counted. In other embodiments, such numbers can be used in another formula to obtain the parameter.

In one embodiment, the concentration of the variant at each locus can be a parameter and compared with a threshold. This threshold can be used to determine if a locus is a potential variant locus (in addition to the cutoff of a specific number of reads showing the variant), and then have the locus be counted. The concentration could also be used as a weighting factor in a sum of the SNMs.

VI. DECREASING FALSE POSITIVES USING CUTOFF VALUES

As mentioned above, the single nucleotide mutations can be surveyed in a large number of cell-free DNA fragments (e.g. circulating DNA in plasma) for a large genomic region (e.g. the entire genome) or a number of genomic regions to improve the sensitivity of the approach. However, analytical errors such as sequencing errors can affect the feasibility, accuracy and specificity of this approach. Here, we use the massively parallel sequencing platform as an example to illustrate the importance of sequencing errors. The sequencing error rate of the Illumina sequencing-by-synthesis platform is approximately 0.1% to 0.3% per sequenced nucleotide (Minoche et al. Genome Biol 2011, 12:R112). Any massively parallel sequencing platform may be used, including a sequencing-by-ligation platform (e.g. the Life Technologies SOLiD platform), the Ion Torrent/Ion Proton, semiconductor sequencing, Roche 454, single molecular sequencing platforms (e.g. Helicos, Pacific Biosciences and nanopore).

In a previous study on hepatocellular carcinoma, it was shown that there are approximately 3,000 single nucleotide mutations for the whole cancer genome (Tao Y et al. 2011 Proc Natl Acad Sci USA; 108: 12042-12047). Assuming that only 10% of the total DNA in the circulation is derived from the tumor cells and we sequence the plasma DNA with an average sequencing depth of one fold haploid genome coverage, we would encounter 9 million ($3\times10^9\times0.3\%$) single nucleotide variations (SNVs) due to sequencing errors. However, most of the single nucleotide mutations are expected to occur on only one of the two homologous chromosomes. With a sequencing depth of one-fold haploid genome coverage of a sample with 100% tumor DNA, we expect to detect only half of the 3,000 mutations, i.e. 1,500 mutations. When we sequence the plasma sample containing 10% tumor-derived DNA to one haploid genome coverage, we expect to detect only 150 (1,500×10%) cancer-associated single nucleotide mutations. Thus, the signal-to-noise ratio for the detection of cancer-associated mutations is 1 in 60,000. This very low signal-to-noise ratio suggests that the accuracy of using this approach for differentiating normal and cancer cases would be very low if we simply use all the single nucleotide changes in the biological sample (e.g., plasma) as a parameter.

It is expected that with the progress in sequencing technologies, there would be continual reduction in the sequencing error rate. One can also analyze the same sample using more than one sequencing platform and through a comparison of the cross-platform sequencing results, pinpoint the reads likely to be affected by sequencing errors. Another approach is to analyze two samples taken at different times from the same subject. However, such approaches are time consuming.

In one embodiment, one way to enhance the signal-to-noise ratio in the detection of single nucleotide mutations in the plasma of cancer patients is to count a mutation only if there are multiple occurrences of the same mutation in the sample. In selected sequencing platforms, the sequencing errors involving particular nucleotide substitutions might be more common and would affect the sequencing results of the test sample and the constitutional DNA sample of both the test subject and the control subjects. However, in general, sequencing errors occur randomly.

The chance of having a sequencing error is exponentially lower when one observes the same change at the same nucleotide position in multiple DNA fragments. On the other hand, the chance of detecting a genuine cancer-associated mutational change in the sample is affected by the sequencing depth and the fractional concentration of the tumoral DNA in the sample. The chance of observing the mutation in multiple DNA fragments would increase with the sequencing depth and fractional concentration of tumoral DNA. In various embodiments using samples with cell-free tumoral DNA (such as in plasma), the fractional concentration can be 5%, 10%, 20%, and 30%. In one embodiment, the fractional concentration is less than 50%.

FIG. 4 is a table 400 showing the number of cancer-associated single nucleotide mutations correctly identified using different number of occurrences as the criterion for classifying a mutation as being present in the sample according to embodiments of the present invention. The numbers of nucleotide positions that are falsely identified as having mutation because of sequencing error based on the same classification criteria are also shown. The sequencing error rate is assumed to be 0.1% (Minoche et al. Genome Bio 2011, 12:R112). The fractional concentration of tumor-derived DNA in the sample is assumed to be 10%.

FIG. 4 shows that the ratio between the number of cancer-associated mutations detected in the plasma and the number of false-positive calls would increase exponentially with the increasing number of times the same change is seen in the sample for defining a mutation, when the fractional concentration of tumor-derived DNA in the sample is assumed to be 10%. In other words, both the sensitivity and specificity for cancer mutation detection would improve. In addition, the sensitivity for detecting the cancer-associated mutations is affected by the sequencing depth. With 100-fold haploid genome coverage of sequencing, 2,205 (73.5%) of the 3,000 mutations can be detected even using the criterion of the occurrence of the particular mutation in at least 4 DNA fragments in the sample. Other values for the minimum number of fragments may be used, such as 3, 5, 8, 10, and greater than 10.

FIG. 5 is a table 500 showing the expected number of false-positive loci and the expected number of mutations identified when the fractional concentration of tumor-derived DNA in the sample is assumed to be 5%. With a lower fractional concentration of tumor-derived DNA in the sample, a higher sequencing depth would be required to achieve the same sensitivity of detecting the cancer-associated mutations. A more stringent criterion would also be required to maintain the specificity. For example, the criterion of the occurrence of the particular mutation in at least 5 DNA fragments, instead of the criterion of at least 4 occurrences in the situation of 10% tumor DNA fraction, in the sample would need to be used. Tables 400 and 500 provide guidance for the cutoff value to use given the fold coverage and a tumor DNA concentration, which can be assumed or measured as described herein.

Another advantage of using the criteria of detecting a single nucleotide change more than one time to define a mutation is that this is expected to minimize false positives detection because of single nucleotide changes in non-malignant tissues. As nucleotide changes can occur during mitosis of normal cells, each healthy cell in the body can harbor a number of single nucleotide changes. These changes may potentially lead to false positive results. However, the changes of a cell would be present in the plasma/serum when the cell dies. While different normal cells are expected to carry different sets of mutations, the mutations occurring in one cell are unlikely to be present in numerous copies in the plasma/serum. This is in contrast to mutations within tumor cells where multiple copies are expected to be seen in plasma/serum because tumor growth is clonal in nature. Thus, multiple cells from a clone would die and release the signature mutations representative of the clones.

In one embodiment, target enrichment for specific genomic regions can be performed before sequencing. This target enrichment step can increase the sequencing depth of the regions of interest with the same total amount of sequencing performed. In yet another embodiment, a round of sequencing with relatively low sequencing depth can first be performed. Then regions showing at least one single nucleotide change can be enriched for a second round of sequencing which has higher fold coverage. Then, the criterion of multiple occurrences can be applied to define a mutation for the sequencing results with target enrichment.

VII. DYNAMIC CUTOFFS

As described above, a cutoff value N for the number of reads supporting a variant (potential mutation) can be used to determine whether a locus qualifies as a mutation (e.g., an SNM) to be counted. Using such a cutoff can reduce false positives. The discussion below provides methods for selecting a cutoff for different loci. In the following embodiments, we assume that there is a single predominant cancer clone. Similar analysis can be carried out for scenarios involving multiple clones of cancer cells releasing different amounts of tumor DNA into the plasma.

A. Number of Cancer-Associated Mutations Detected in Plasma

The number of cancer-associated mutations detectable in plasma can be affected by a number of parameters, for example: (1) The number of mutations in the tumor tissue ($N_T$)—the total number of mutations present in the tumor tissue is the maximum number of tumor-associated mutations detectable in the plasma of the patient; (2) The fractional concentration of tumor-derived DNA in the plasma (f)—the higher the fractional concentration of tumor-derived DNA in the plasma, the higher the chance of detecting the tumor-associated mutations in the plasma would be; (3) Sequencing depth (D)—Sequencing depth refers to the number of times the sequenced region is covered by the sequence reads. For example, an average sequencing depth of 10-fold means that each nucleotide within the sequenced region is covered on average by 10 sequence reads. The chance of detecting a cancer-associated mutation would increase when the sequencing depth is increased; and (4) The minimum number of times a nucleotide change that is detected in the plasma so as to define it as a potential cancer-associated mutation (r), which is a cutoff value used to discriminate sequencing errors from real cancer-associated mutations.

In one implementation, the Poisson distribution is used to predict the number of cancer-associated mutations detected in plasma. Assuming that a mutation is present in a nucleotide position on one of the two homologous chromosomes, with a sequencing depth of D, the expected number of times a mutation is present in the plasma ($M_P$) is calculated as: $M_P=D\times f/2$.

The probability of detecting the mutation in the plasma (Pb) at a particular mutation site is calculated as:

$$Pb = 1 - \sum_{i=0}^{r-1} \text{Poisson}(i, M_P)$$

where r (cutoff value) is the number of times that a nucleotide change is seen in the plasma so as to define it as a potential tumor-associated mutation; Poisson (i,$M_P$) is the Poisson distribution probability of having i occurrences with an average number of $M_P$.

The total number of cancer-associated mutations expected to be detected in the plasma (NP) can be calculated as: $N_P=N_T\times Pb$, where $N_T$ is the number of mutations present in the tumor tissue. The following graphs show the percentages of tumor-associated mutations expected to be detected in the plasma using different criteria of occurrences (r) for calling a potential mutation and different sequencing depths.

Figure 6A:
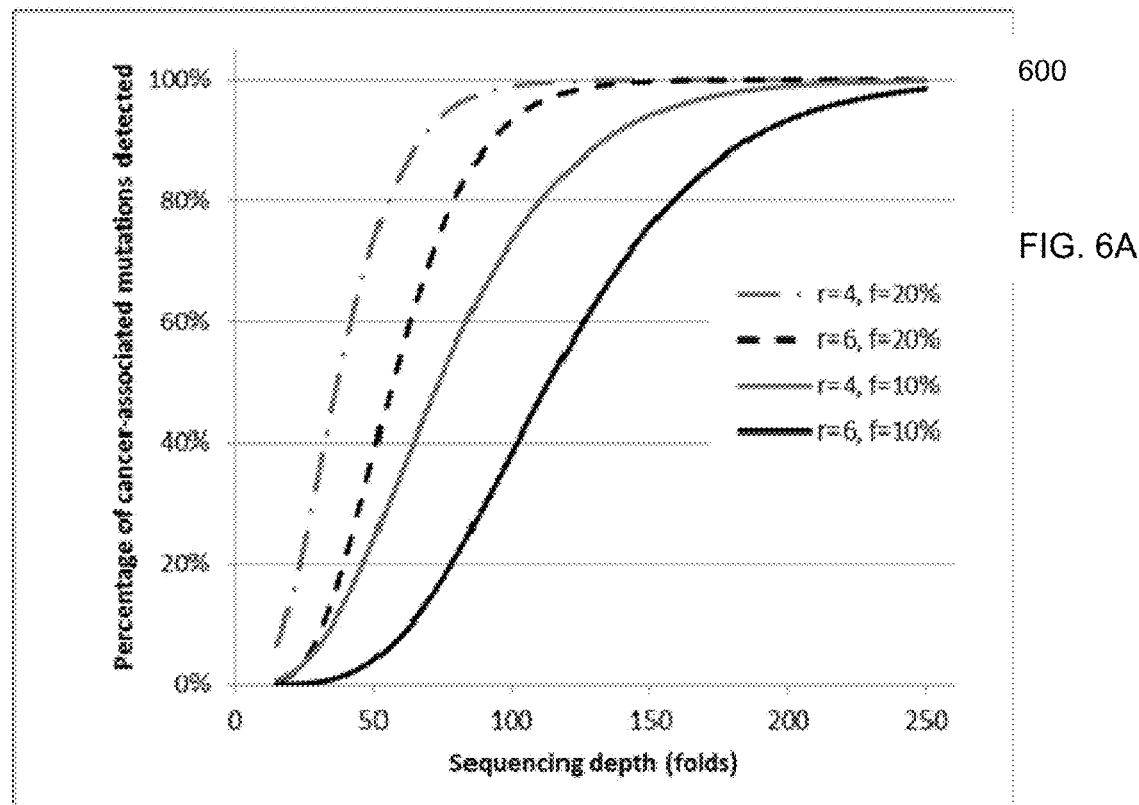
FIG. 6A is a graph 600 showing the detection rate of cancer-associated mutations in plasma with 10% and 20% plasma fractional concentrations of tumor-derived DNA and using four and six occurrences (r) as criteria for calling potential cancer-associated mutations.

FIG. 6A is a graph 600 showing the detection rate of cancer-associated mutations in plasma with 10% and 20% plasma fractional concentrations of tumor-derived DNA and using four and six occurrences (r) as criteria for calling potential cancer-associated mutations. With the same r, a higher fractional concentration of tumor-derived DNA in plasma would result in a higher number of cancer-associated mutations detectable in the plasma. With the same fractional concentration of tumor-derived DNA in plasma, a higher r would result in a smaller number of detected mutations.

B. Number of False-Positive Single Detected Due to Errors

Single nucleotide changes in the plasma DNA sequencing data can occur due to sequencing and alignment errors. The number of nucleotide positions with false-positive single nucleotide changes can be predicted mathematically based on a binomial distribution. The parameters affecting the number of false-positive sites ($N_{FP}$) can include: (1) Sequencing error rate (E)—Sequencing error rate is defined as the proportion of sequenced nucleotide being incorrect; (2) Sequencing depth (D)—With a higher sequencing depth, the number of nucleotide positions showing a sequencing error would increase; (3) The minimum number of occurrences of the same nucleotide change for defining a potential cancer-associated mutation (r); and (4) The total number of nucleotide positions within the region-of-interest ($N_I$).

The occurrence of mutations can generally be regarded as a random process. Therefore, with the increase of the criteria of occurrence for defining a potential mutation, the number of false-positive nucleotide positions would exponentially decrease with r. In some of the existing sequencing platforms, certain sequence contexts are more prone to having sequencing errors. Examples of such sequencing contexts include the GGC motif, homopolymers (e.g. AAAAAAA), and simple repeats (e.g. ATATATATAT). These sequence contexts will substantially increase the single nucleotide change or insertion/deletion artifacts (Nakamura K et al. Nucleic Acids Res 2011; 39, e90 and Minoche A E et al. Genome Biol 2011; 12, R112). In addition, repeat sequences, such as homopolymers and simple repeats, would computationally introduce ambiguities in alignment and, hence, lead to false-positive results for single nucleotide variations.

The larger the region-of-interest, the higher the number of false-positive nucleotide positions would be observed. If one is looking for mutations in the whole genome, then the region-of-interest would be the whole genome and the number of nucleotides involved would be 3 billion. On the other hand, if one focuses on the exons, then the number of nucleotides encoding the exons, i.e. approximately 45 million, would constitute the region-of-interest.

The number of false-positive nucleotide positions associated with sequencing errors can be determined based on the following calculations. The probability ($P_{Er}$) of having the same nucleotide change at the same position due to sequencing errors can be calculated as:

$$P_{Er} = C(D,r)E\left(\frac{E}{3}\right)^{r-1}$$

where C(D,r) is the number of possible combinations for choosing r elements from a total of D elements; r is the number of occurrences for defining a potential mutation; D is the sequencing depth; and E is the sequencing error rate. C(D,r) can be calculated as:

$$C(D,r) = \frac{D!}{r!(D-r)!}$$

The number of nucleotide positions ($N_{FP}$) being false-positives for mutations can be calculated as:

$$N_{FP}=N_I P_{Er}$$

where $N_I$ is the total number of nucleotide positions in the region-of-interest.

Figure 6B:
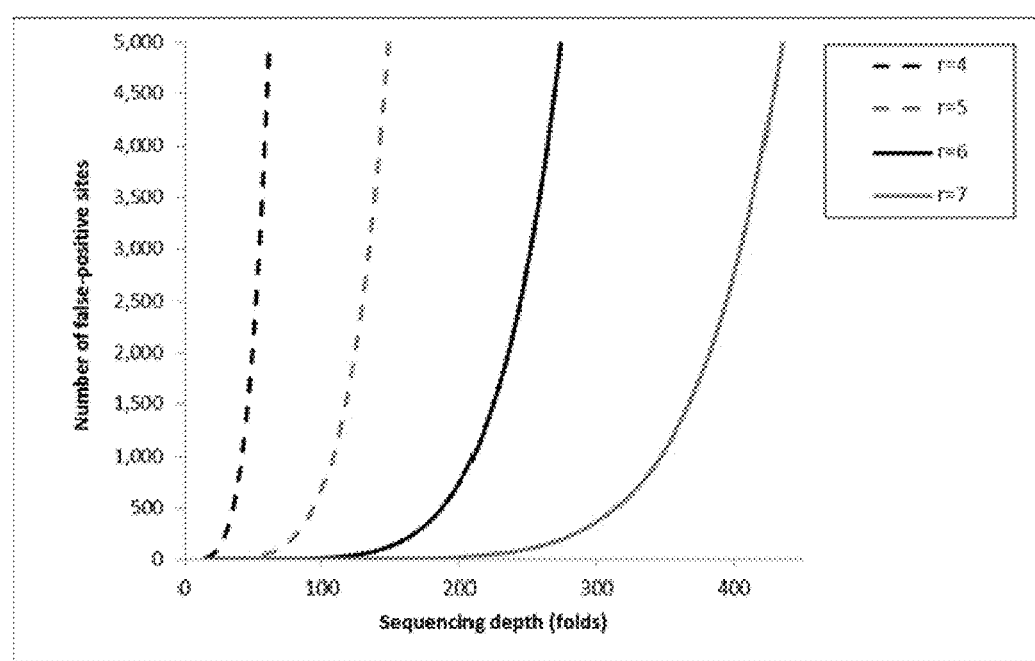
FIG. 6B is a graph 650 showing the expected number of nucleotide positions falsely classified as having a nucleotide change using criteria of occurrence (r) of 4, 5, 6 and 7 vs. sequencing depth.

FIG. 6B is a graph 650 showing the expected number of nucleotide positions falsely classified as having a nucleotide change using criteria of occurrence (r) of 4, 5, 6 and 7 vs. sequencing depth. The region-of-interest is assumed to be the whole genome (3 billion nucleotide positions) in this calculation. The sequencing error rate is assumed to be 0.3% of the sequenced nucleotides. As one can see, the value of r has a significant impact on the false positives. But, as can be seen from FIG. 6A, a higher value of r also reduces the number of mutations detected, at least until significantly higher sequencing depths are used.

C. Choosing Minimum Occurrence (r)

As discussed above, the number of true cancer-associated mutation sites and false-positive sites due to sequencing errors would increase with sequencing depth. However, their rates of increase would be different. Therefore, it is possible to make use of the choice of sequencing depth and the value of r to maximize the detection of true cancer-associated mutations while keeping the number of false-positive sites at a low value.

Figure 7A:
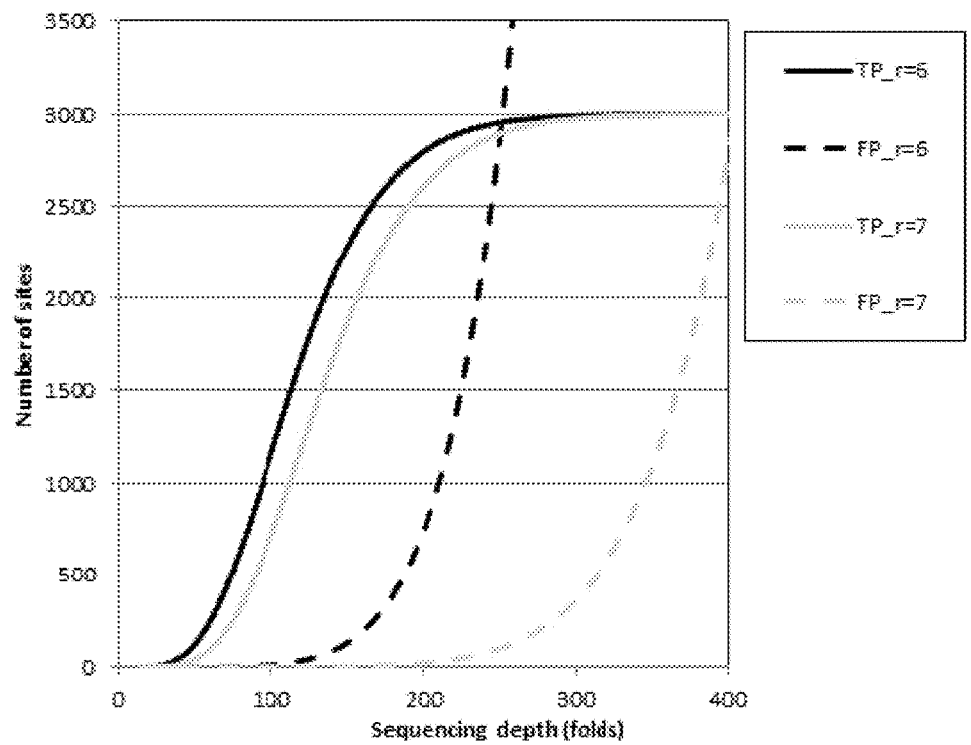
FIG. 7A is a graph 700 showing the number of true cancer-associated mutation sites and false-positive sites with difference sequencing depths when the fractional concentration of tumor-derived DNA in the sample is assumed to be 5%.

FIG. 7A is a graph 700 showing the number of true cancer-associated mutation sites and false-positive sites with difference sequencing depths. The total number of cancer-associated mutations in the tumor tissue is assumed to be 3,000 and the fractional concentration of tumor-derived DNA in the plasma is assumed to be 10%. The sequencing error rate is assumed to be 0.3%. In the legend, TP denotes the true-positive sites at which a corresponding mutation is present in the tumor tissue, and FP denotes false-positive sites at which no corresponding mutation is present in the tumor tissue and the nucleotide changes present in the sequencing data are due to sequencing errors.

From graph 700, at a sequencing depth of 110-fold, approximately 1,410 true cancer-associated mutations would be detected if we use the minimum occurrence of 6 as the criterion (r=6) to define a potential mutation site in the plasma. Using this criterion, only approximately 20 false-positive sites would be detected. If we use the minimum of 7 occurrences (r=7) as the criterion to define a potential mutation, the number of cancer-associated mutations that could be detected would be reduced by 470 to approximately 940. Therefore, the criterion of r=6 would make the detection of cancer-associated mutations in plasma more sensitive.

On the other hand, at a sequencing depth of 200-fold, the number of true cancer-associated mutations detected would be approximately 2,800 and 2,600, if we use the criteria of minimum occurrence (r) of 6 and 7, respectively, to define potential mutations. Using these two values of r, the numbers of false-positive sites would be approximately 740 and 20, respectively. Therefore, at a sequencing depth of 200-fold, the use of a more stringent criterion of r=7 for defining a potential mutation can greatly reduce the number of false-positive sites without significantly adversely affecting the sensitivity for detecting the true cancer-associated mutations.

D. Dynamic Cutoff for Sequencing Data for Defining Potential Mutations in Plasma The sequencing depth of each nucleotide within the region-of-interest would be different. If we apply a fixed cutoff value for the occurrence of a nucleotide change to define a potential mutation in plasma, the nucleotides that are covered by more sequence reads (i.e. a higher sequencing depth) would have higher probabilities of being falsely labeled as having nucleotide variation in the absence of such a change in the tumor tissue due to sequencing errors compared with nucleotides that have lower sequencing depths. One embodiment to overcome this problem is to apply a dynamic cutoff value of r to different nucleotide positions according to the actual sequencing depth of the particular nucleotide position and according to the desired upper limit of the probability for calling false-positive variations.

In one embodiment, the maximum allowable false-positive rate can be fixed at 1 in $1.5 \times 10^8$ nucleotide positions. With this maximum allowable false-positive rate, the total number of false-positive sites being identified in the whole genome would be less than 20. The value of r for different sequencing depths can be determined according to the curves shown in FIG. 6B and these cutoffs are shown in Table 1. In other embodiments, other different maximum allowable false-positive rates, e.g. 1 in $3 \times 10^8$, 1 in $10^8$ or 1 in $6 \times 10^7$, can be used. The corresponding total number of false-positive sites would be less than 10, 30 and 50, respectively.

TABLE 1

The minimum number of occurrences of a nucleotide change present in plasma to define a potential mutation (r) for different sequencing depths of the particular nucleotide position. The maximum false-positive rate is fixed at 1 in $1.5 \times 10^8$ nucleotides.

| Sequencing depth of a particular nucleotide position | Minimum number of occurrence of a nucleotide change to be present in the plasma DNA sequencing data to define a potential mutation (r) |
| --- | --- |
| <50 | 5 |
| 50-110 | 6 |
| 111-200 | 7 |
| 201-310 | 8 |
| 311-450 | 9 |
| 451-620 | 10 |
| 621-800 | 11 |

E. Target-Enrichment Sequencing

As shown in FIG. 7A, a higher sequencing depth can result in a better sensitivity for detecting cancer-associated mutations while keeping the number false-positive sites low by allowing the use of a higher value of r. For example, at a sequencing depth of 110-fold, 1,410 true cancer-associated mutations can be detected in the plasma using an r value of 6 whereas the number of true cancer-associated mutations detected would be 2,600 when the sequencing depth increases to 200-fold and an r value of 7 is applied. The two sets of data would give an expected number of false-positive sites of approximately 20.

While the sequencing of the whole genome to a depth of 200-fold is relatively expensive at present, one possible way of achieving such a sequencing depth would be to focus on a smaller region-of-interest. The analysis of a target region can be achieved for example by, but not limited to, the use of DNA or RNA baits to capture genomic regions of interest by hybridization. The captured regions are then pulled down, e.g., by magnetic means and then subjected to sequencing. Such target capture can be performed, for example, using the Agilent SureSelect target enrichment system, the Roche Nimblegen target enrichment system and the Illumina targeted resequencing system. Another approach is to perform PCR amplification of the target regions and then perform sequencing. In one embodiment, the region-of-interest is the exome. In such an embodiment, target capturing of all exons can be performed on the plasma DNA, and the plasma DNA enriched for exonic regions can then be sequenced.

In addition to having higher sequencing depth, the focus on specific regions instead of analyzing the whole genome would significantly reduce the number of nucleotide positions in the search space and would lead to a reduction in the number of false-positive sites given the same sequencing error rate.

Figure 7B:
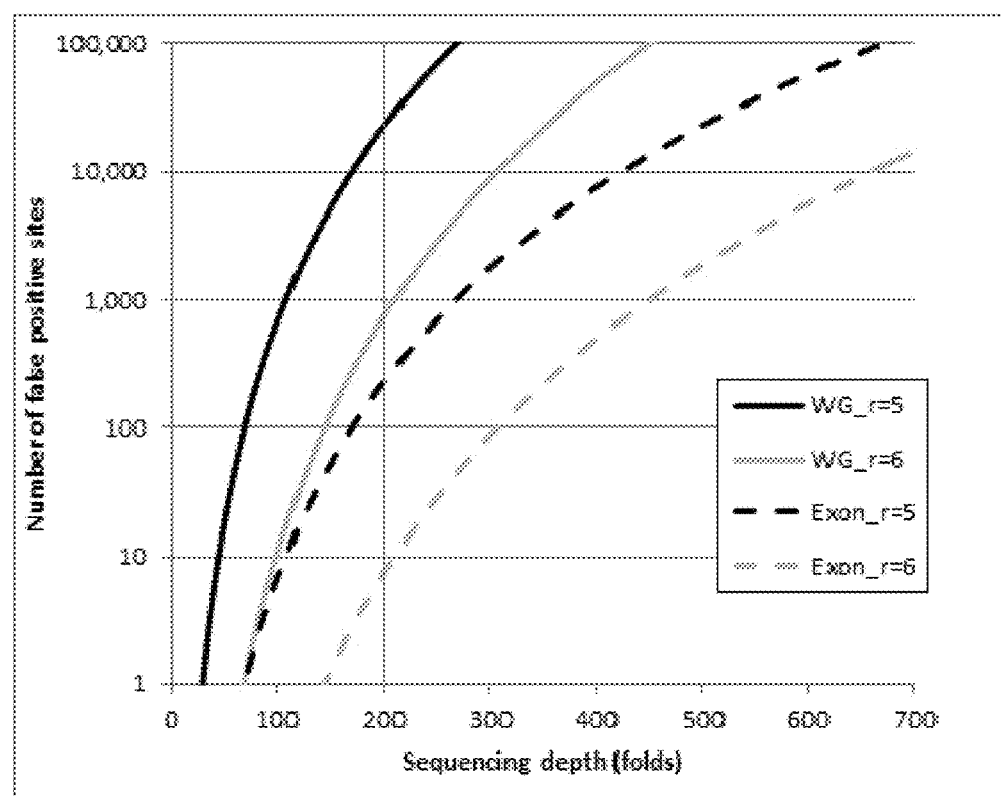
FIG. 7B is a graph 750 showing the predicted number of false-positive sites involving the analysis of the whole genome (WG) and all exons.

FIG. 7B is a graph 750 showing the predicted number of false-positive sites involving the analysis of the whole genome (WG) and all exons. For each type of analysis, two different values, 5 and 6, for r are used. At a sequencing depth of 200-fold, if r=5 is used to define mutations in plasma, the predicted number of false-positive sites are approximately 23,000 and 230 for the whole genome and all exons, respectively. If r=6 is used to define mutations in plasma, the predicted number of false-positive sites are 750 and 7, respectively. Therefore, the limit of the number of nucleotides in the region-of-interest can significantly reduce the number of false-positives in plasma mutational analysis.

In exon-capture or even exome-capture sequencing, the number of nucleotides in the search space is reduced. Therefore, even if we allow a higher false-positive rate for the detection of cancer-associated mutations, the absolute number of false-positive sites can be kept as a relatively low level. The allowance of higher false-positive rate would allow a less stringent criterion of minimum occurrences (r) for defining a single nucleotide variation in plasma to be used. This would result in a higher sensitivity for the detection of true cancer-associated mutations.

In one embodiment, we can use a maximum allowable false-positive rate of $1.5 \times 10^6$. With this false-positive rate, the total number of false-positive sites within the targeted exons would only be 20. The values of r for different sequencing depths using a maximum allowable false-positive rate of $1.5 \times 10^6$ are shown in Table 2. In other embodiments, other different maximum allowable false-positive rates, e.g. 1 in $3 \times 10^6$, 1 in $10^6$ or 1 in $6 \times 10^5$, can be used. The corresponding total number of false-positive sites would be less than 10, 30 and 50, respectively. In one embodiment, different classes of mutations can be attributed different weightings, as described above.

TABLE 2

The minimum number of occurrence of a nucleotide change present in plasma to define a potential mutation (r) for different sequencing depths of the particular nucleotide position. The maximum false-positive rate is fixed at 1 in $1.5 \times 10^6$ nucleotides.

| Sequencing depth of a particular nucleotide position | Minimum number of occurrence of a nucleotide change to be present in the plasma DNA sequencing data to define a potential mutation (r) |
|---|---|
| <50 | 4 |
| 50-125 | 5 |
| 126-235 | 6 |
| 236-380 | 7 |
| 381-560 | 8 |
| 561-760 | 9 |

VIII. CANCER DETECTION

As mentioned above, the counts of sequence tags at variant loci can be used in various ways to determine the parameter, which is compared to a threshold to classify a level of cancer. The fractional concentration of variant reads relative to all reads at a locus or many loci is another parameter that may be used. Below are some examples of calculating the parameter and the threshold.

A. Determination of Parameter

If the CG is homozygous at a particular locus for a first allele and a variant allele is seen in the biological sample (e.g., plasma), then the fractional concentration can be calculated as $2p/(p+q)$, where p is the number of sequence tags having the variant allele and q is the number of sequence tags having the first allele of the CG. This formula assumes that that only one of the haplotypes of the tumor has the variant, which would typically be the case. Thus, for each homozygous locus a fractional concentration can be calculated. The fractional concentrations can be averaged. In another embodiment, the count p can include the number of sequence tags for all of the loci, and similarly for the count q, to determine the fractional concentration. An example is now described.

The genomewide detection of tumor derived single nucleotide variants (SNVs) in the plasma of the 4 HCC patients was explored. We sequenced tumor DNA and buffy coat DNA to mean depths of 29.5-fold (range, 27-fold to 33-fold) and 43-fold (range, 39-fold to 46-fold) haploid genome coverage, respectively. The MPS data from the tumor DNA and the buffy coat DNA from each of the 4 HCC patients were compared, and SNVs present in the tumor DNA but not in the buffy coat DNA were mined with a stringent bioinformatics algorithm. This algorithm required a putative SNV to be present in at least a threshold number of sequenced tumor DNA fragments (i.e. in a corresponding sequenced tag) before it would be classified as a true SNV. The threshold number was determined by taking into account the sequencing depth of a particular nucleotide and the sequencing error rate, e.g., as described herein.

FIG. 8 is a table 800 showing results for 4 HCC patients before and after treatment, including fractional concentrations of tumor-derived DNA in plasma according to embodiments of the present invention. The number of tumor-associated SNVs ranged from 1,334 to 3,171 in the 4 HCC cases. The proportions of such SNVs that were detectable in plasma are listed before and after treatment. Before treatment, 15%-94% of the tumor associated SNVs were detected in plasma. After treatment, the percentage was between 1.5%-5.5%. Thus, the number of detected SNVs does correlate to a level of cancer. This shows that the number of SNVs can be used as a parameter to classify a level of cancer.

The fractional concentrations of tumor-derived DNA in plasma were determined by the fractional counts of the mutant with respect to the total (i.e., mutant plus wild type) sequences. The formula is $2p/(p+q)$, where the 2 accounts for just one haplotype being mutated on the tumor. These fractional concentrations were well correlated with those determined with genomewide aggregated allelic loss (GAAL) analysis (Chan K C et al. Clin Chem 2013; 59:211-24) and were reduced after surgery. Thus, the fractional concentration is also shown to be a usable parameter for determining a level of cancer.

The fractional concentration from the SNV analysis can convey a tumor load. A cancer patient with a higher tumor load (e.g., a higher deduced fractional concentration) will have a higher frequency of somatic mutations than one with a lower tumor load. Thus, embodiments can also be used for prognostication. In general, cancer patients with higher tumor loads have worse prognosis than those with lower tumor loads. The former group would thus have a higher chance of dying from the disease. In some embodiments, if the absolute concentration of DNA in a biological sample, e.g. plasma, can be determined (e.g. using real-time PCR or fluorometry), then the absolute concentration of tumor-associated genetic aberrations can be determined and used for clinical detection and/or monitoring and/or prognostication.

B. Determining of Threshold

Table 800 may be used to determine a threshold. As mentioned above, the number of SNVs and a fractional concentration determined by SNV analysis correlate to a level of cancer. The threshold can be determined on an individual basis. For example, the pre-treatment value can be used to determine the threshold. In various implementations, the threshold could be a relative change from the pre-treatment of an absolute value. A suitable threshold could be a reduction in number of SNVs or fractional concentration by 50%. Such a threshold would provide a classification of a lower level of cancer for each of the cases in table 800. Note that such threshold may be dependent on the sequencing depth.

In one embodiment, a threshold could be used across samples, and may or may not account for pre-treatment values for the parameter. For example, a threshold of 100 SNVs could be used to classify the subject as having no cancer or a low level of cancer. This threshold of 100 SNVs is satisfied by each of the four cases in table 800. If the fractional concentration was used as the parameter, a threshold of 1.0% would classify HCC1-HCC3 as practically zero level of cancer, and a second threshold of 1.5% would classify HCC4 as a low level of cancer. Thus, more than one threshold may be used to obtain more than two classifications.

To illustrate other possible thresholds, we analyzed the plasma of the healthy controls for the tumor-associated SNVs. Numerous measurements can be made of healthy subjects to determine a range of how many variations are expected from the biological sample relative to the constitutional genome.

FIG. 9 is a table 900 showing detection of the HCC-associated SNVs in 16 healthy control subjects according to embodiments of the present invention. Table 900 can be used to estimate the specificity of an SNV analysis approach. The 16 healthy controls are listed as different rows. The columns investigate the SNVs detected for the specific HCC patients, and show the number of sequence reads at variant loci having the variant allele and the number of sequence reads with the wildtype allele (i.e., the allele from the CG). For example, for HCC1, control C01 had 40 variant reads at such variant loci, but 31,261 reads of the wildtype allele. The last column shows the total fractional concentration across all of the SNVs for the HCC1 patients. As the HCC-associated SNVs were specific for the HCC patients, the presence of the HCC-associated SNVs represent false-positives. If a cutoff values, as described herein, are applied to these apparent sequence variants, all of these false-positives would be filtered away.

The presence of a small number of these putative tumor-associated mutations in the plasma of the 16 healthy controls represented the "stochastic noise" of this method and was likely due to sequencing errors. The mean fractional concentration estimated from such noise was 0.38%. These values show a range for healthy subjects. Thus, a threshold value for a classification of zero level of cancer for HCC could be about 0.5%, since the highest fractional concentration was 0.43%. Thus, if all the cancer cells are removed from an HCC patient, these low fractional concentrations would be expected.

Referring back to table 800, if 0.5% was used as a threshold for zero level of cancer, then the post-treatment plasma data for HCC1 and HCC3 would be determined as having zero level based on the SNV analysis. HCC2 might be classified as one level up from zero. HCC4 might also be classified as one level up from zero, or some higher level, but still a relatively low level compared to the pre-treatment samples.

In one embodiment where the parameter corresponds to the number of variant loci, the threshold could be zero (i.e., one variant locus could indicate a non-zero level of cancer). However, with many settings (e.g., of depth), the threshold would be higher, e.g., an absolute value of 5 or 10. In one implementation where a person is monitored after treatment, the threshold can be a certain percentage of SNVs (identified by analyzing the tumors directly) showing up in the sample. If the cutoff value for the number of variant reads required at a locus was large enough, just having one variant loci might be indicative of a non-zero level of cancer.

Thus, quantitative analysis of variations (e.g., single nucleotide variations) in DNA from a biological sample (e.g., plasma) can be used for the diagnosis, monitoring and prognostication of cancer. For the detection of cancer, the number of single nucleotide variations detected in the plasma of a tested subject can be compared with that of a group of healthy subjects. In the healthy subjects, the apparent single nucleotide variations in plasma can be due to sequencing errors, non-clonal mutations from the blood cells and other organs. It has been shown that the cells in normal healthy subjects could carry a small number of mutations (Conrad D F et al. Nat Genet 2011; 43:712-4), as shown in table 900. Thus, the overall number of apparent single nucleotide variations in the plasma of a group of apparently healthy subjects can be used as a reference range to determine if the tested patient has an abnormally high number of single nucleotide variations in plasma corresponding to a non-zero level of cancer.

The healthy subjects used for establishing the reference range can be matched to the tested subject in terms of age and sex. In a previous study, it has been shown that the number of mutations in the somatic cells would increase with age (Cheung N K et al, JAMA 2012; 307:1062-71). Thus, as we grow older, then it would be 'normal' for one to accumulate clones of cells, even though they are relatively benign most of the time, or would take a very long time to become clinically significant. In one embodiment, reference levels can be generated for different subject groups, e.g. different age, sex, ethnicity, and other parameters (e.g. smoking status, hepatitis status, alcohol, drug history).

The reference range can vary based on the cutoff value used (i.e., the number of variant sequence tags required at a locus), as well as the assumed false positive rate and other variables (e.g., age). Thus, the reference range may be determined for a particular set of one or more criteria, and the same criteria would be used to determine a parameter for a sample. Then, the parameter can be compared to the reference range, since both were determined using the same criteria.

As mentioned above, embodiments may use multiple thresholds for determining a level of cancer. For example, a first level could determine no signs of cancer for parameters below the threshold, and at least a first level of cancer, which could be a pre-neoplastic level. Other levels could correspond to different stages of cancer.

C. Dependency on Experimental Variables

The depth of sequencing can be important for establishing the minimum detection threshold of the minority (e.g. tumor) genome. For example, if one uses a sequencing depth of 10 haploid genomes, then the minimum tumoral DNA concentration that one could detect even with a sequencing technology without any error is ⅕, i.e. 20%. On the other hand, if one uses a sequencing depth of 100 haploid genomes, then one could go down to 2%. This analysis is referring to the scenario that only one mutation locus is being analyzed. However, when more mutation loci are analyzed, the minimum tumoral DNA concentration can be lower and is governed by a binomial probability function. For example, if the sequencing depth is 10 folds and the fractional concentration of tumoral DNA is 20%, then the chance of detecting the mutation is 10%. However, if we have 10 mutations, then the chance of detecting at least one mutation would be $1-(1-10\%)^{10}=65\%$.

There are several effects for increasing the sequencing depth. The higher the sequencing depth, the more sequencing errors would be seen, see FIGS. 4 and 5. However, with a higher sequencing depth, one can more easily differentiate sequencing errors from mutations due to clonal expansion of a subpopulation of cells (e.g. cancer cells) because the sequencing errors would occur randomly in the genome but the mutations would occur at the same location for the given population of cells.

The higher the sequencing depth, the more mutations from the "healthy cells" would be identified. However, when there is no clonal expansion of these healthy cells and their mutational profiles are different, then the mutations in these healthy cells can be differentiated from the mutations by their frequencies of occurrence in the plasma (e.g., by using a cutoff N for a required number of reads exhibiting the mutation, such as having N equal to 2, 3, 4, 5, or larger).

As mentioned above, the threshold can depend on an amount of mutations in healthy cells that would be clonally expanded, and thus might not be filtered out through other mechanisms. This variance that one would expect can be obtained by analyzing healthy subjects. As clonal expansion occurs over time, the age of patient can affect a variance that one sees in healthy subjects, and thus the threshold can be dependent on age.

D. Combination with Targeted Approaches

In some embodiments, a random sequencing can be used in combination with targeted approaches. For example, one can perform random sequencing of a plasma sample upon presentation of a cancer patient. The sequencing data of plasma DNA can be analyzed for copy number aberrations and SNVs. The regions showing aberrations (e.g., amplification/deletion or high density of SNVs) can be targeted for serial monitoring purposes. The monitoring can be done over a period of time, or done immediately after the random sequencing, effectively as a single procedure. For the targeted analysis, solution-phase hybridization-based capture approaches have been successfully used to enrich plasma DNA for noninvasive prenatal diagnosis (Liao G J et al. Clin Chem 2011; 57:92-101). Such techniques are mentioned above. Thus, the targeted and random approaches can be used in combination for cancer detection and monitoring.

Thus, one could perform targeted sequencing of the loci that are found to be potentially mutated using the non-targeted, genomewide approach mentioned above. Such targeted sequencing could be performed using solution- or solid-phase hybridization techniques (e.g. using the Agilent SureSelect, NimbleGen Sequence Capture, or Illumina targeted resequencing system) followed by massively parallel sequencing. Another approach is to perform amplification (e.g. PCR based) system for targeted sequencing (Forshew T et al. Sci Transl Med 2012; 4: 135ra68).

IX. FRACTIONAL CONCENTRATION

The fractional concentration of tumor DNA can be used to determine the cutoff value for the required number of variations at a locus before the locus is identified as a mutation. For example, if the fractional concentration was known to be relatively high, then a high cutoff could be used to filter out more false positives, since one knows that a relatively high number of variant reads should exist for true SNVs. On the other hand, if the fractional concentration was low, then a lower cutoff might be needed so that some SNVs are not missed. In this case, the fractional concentration would be determined by a different method than the SNV analysis, where it is used as a parameter.

Various techniques may be used for determining the fractional concentration, some of which are described herein. These techniques can be used to determine the fractional concentration of tumor-derived DNA in a mixture, e.g. a biopsy sample containing a mixture of tumor cells and nonmalignant cells or a plasma sample from a cancer patient containing DNA released from tumor cells and DNA released from nonmalignant cells.

A. GAAL

Genomewide aggregated allelic loss (GAAL) analyzes loci that have lost heterozygosity (Chan K C et al. Clin Chem 2013; 59:211-24). For a site of the constitutional genome CG that is heterozygous, a tumor often has a locus that has a deletion of one of the alleles. Thus, the sequence reads for such a locus will show more of one allele than another, where the difference is proportional to the fractional concentration of tumor DNA in the sample. An example of such a calculation follows.

DNA extracted from the buffy coat and the tumor tissues of the HCC patients was genotyped with the Affymetrix Genome-Wide Human SNP Array 6.0 system. The microarray data were processed with the Affymetrix Genotyping Console version 4.1. Genotyping analysis and single-nucleotide polymorphism (SNP) calling were performed with the Birdseed v2 algorithm. The genotyping data for the buffy coat and the tumor tissues were used for identifying loss-of-heterozygosity (LOH) regions and for performing copy number analysis. Copy number analysis was performed with the Genotyping Console with default parameters from Affymetrix and with a minimum genomic-segment size of 100 bp and a minimum of 5 genetic markers within the segment.

Regions with LOH were identified as regions having 1 copy in the tumor tissue and 2 copies in the buffy coat, with the SNPs within these regions being heterozygous in the buffy coat but homozygous in the tumor tissue. For a genomic region exhibiting LOH in a tumor tissue, the SNP alleles that were present in the buffy coat but were absent from or of reduced intensity in the tumor tissues were considered to be the alleles on the deleted segment of the chromosomal region. The alleles that were present in both the buffy coat and the tumor tissue were deemed as having been derived from the non-deleted segment of the chromosomal region. For all the chromosomal regions with a single copy loss in the tumor, the total number of sequence reads carrying the deleted alleles and the non-deleted alleles were counted. The difference of these two values was used to infer the fractional concentration of tumor-derived DNA ($F_{GAAL}$) in the sample using the following equation:

$$F_{GAAL} = \frac{N_{non\text{-}del} - N_{del}}{N_{non\text{-}del}}$$

where $N_{non\text{-}del}$ represents the total number of sequence reads carrying the non-deleted alleles and $N_{del}$ represents the total number of sequence reads carrying the deleted alleles.

B. Estimation Using Genomic Representation

A problem with the GAAL technique is that particular loci (i.e. ones exhibiting LOH) are identified and only sequence reads aligning to such loci are used. Such requirement can add additional steps, and thus costs. An embodiment is now described which uses only copy number, e.g., a sequence read density.

Chromosomal aberrations, for example, amplifications and deletions are frequently observed in cancer genomes. The chromosomal aberrations observed in cancer tissues typically involve subchromosomal regions and these aberrations can be shorter than 1 Mb. And, the cancer-associated chromosomal aberrations are heterogeneous in different patients, and thus different regions may be affected in different patients. It is also not uncommon for tens, hundreds or even thousands of copy number aberrations to be found in a cancer genome. All of these factors make determining tumor DNA concentration difficult.

Embodiments involve the analysis of quantitative changes resulted from tumor-associated chromosomal aberrations. In one embodiment, the DNA samples containing DNA derived from cancer cells and normal cells are sequenced using massively parallel sequencing, for example, by the Illumina HiSeq2000 sequencing platform. The derived DNA may be cell-free DNA in plasma or other suitable biological sample.

Chromosomal regions that are amplified in the tumor tissues would have increased probability of being sequenced and regions that are deleted in the tumor tissues would have reduced probability of being sequenced. As a result, the density of sequence reads aligning to the amplified regions would be increased and that aligning to the deleted regions would be reduced. The degree of variation is proportional to the fractional concentration of the tumor-derived DNA in the DNA mixture. The higher the proportion of DNA from the tumor tissue, the larger the change would be caused by the chromosomal aberrations.

1. Estimation in Sample with High Tumor Concentration

DNA was extracted from the tumor tissues of four hepatocellular carcinoma patients. The DNA was fragmented using the Covaria DNA sonication system and sequenced using the Illumina HiSeq2000 platform as described (Chan K C et al. Clin Chem 2013; 59:211-24). The sequence reads were aligned to the human reference genome (hg18). The genome was then divided into 1 Mb bins (regions) and the sequence read density was calculated for each bin after adjustment for GC-bias as described (Chen E Z et al. PLoS One. 2011; 6:e21791).

After sequence reads are aligned to a reference genome, a sequence read density can be computed for various regions. In one embodiment, the sequence read density is a proportion determined as the number of reads mapped to a particular bin (e.g., 1 Mb region) divided by the total sequence reads that can be aligned to the reference genome (e.g., to a unique position in the reference genome). Bins that overlap with chromosomal regions amplified in the tumor tissue are expected to have higher sequence read densities than those from bins without such overlaps. On the other hand, bins that overlap with chromosomal regions that are deleted are expected to have lower sequence read densities than those without such overlaps. The magnitude of the difference in sequence read densities between regions with and without chromosomal aberrations is mainly affected by the proportion of tumor-derived DNA in the sample and the degree of amplification/deletion in the tumor cells.

Various statistical models may be used to identify the bins having sequence read densities corresponding to different types of chromosomal aberrations. In one embodiment, a normal mixture model (McLachlan G and Peel D. Multvariate normal mixtures. In Finite mixture models 2004: p 81-116. John Wiley & Sons Press) can be used. Other statistical models, for example the binomial mixture model and Poisson regression model (McLachlan G and Peel D. Mixtures with non-normal components, Finite mixture models 2004: p 135-174. John Wiley & Sons Press), can also be used.

The sequence read density for a bin can be normalized using the sequence read density of the same bin as determined from the sequencing of the buffy coat DNA. The sequence read densities of different bins may be affected by the sequence context of a particular chromosomal region, and thus the normalization can help to more accurately identify regions showing aberration. For example, the mappability (which refers to the probability of aligning a sequence back to its original position) of different chromosomal regions can be different. In addition, the polymorphism of copy number (i.e. copy number variations) would also affect the sequence read densities of the bins. Therefore, normalization with the buffy coat DNA can potentially minimize the variations associated with the difference in the sequence context between different chromosomal regions.

Figure 10A:
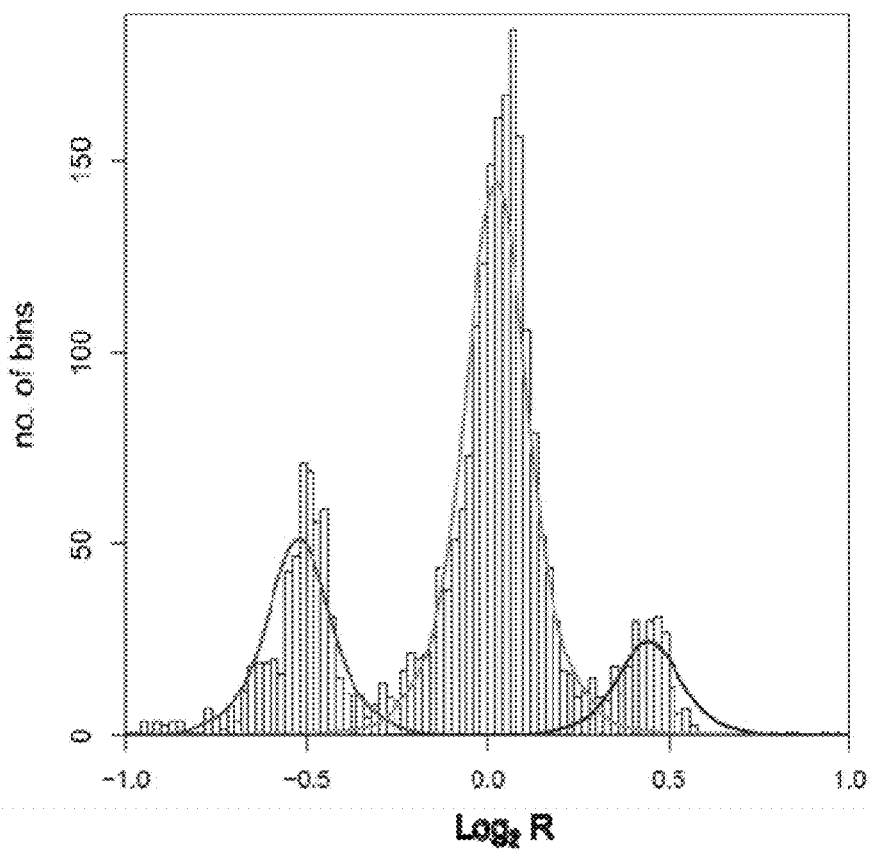
FIG. 10A shows a distribution plot of the sequence read densities of the tumor sample of an HCC patient according to embodiments of the present invention.

FIG. 10A shows a distribution plot 1000 of the sequence read densities of the tumor sample of an HCC patient according to embodiments of the present invention. The tumor tissue was obtained following surgical resection from the HCC patient. The x-axis represents the $\log_2$ of the ratio (R) of the sequence read density between the tumor tissue and the buffy coat of the patient. The y-axis represents the number of bins.

Peaks can be fitted to the distribution curve to represent the regions with deletion, amplification, and without chromosomal aberrations using the normal mixture model. In one embodiment, the number of peaks can be determined by the Akaike's information criterion (AIC) across different plausible values. The central peak with a $\log_2 R=0$ (i.e. R=1) represents the regions without any chromosomal aberration. The left peak (relative to the central one) represents regions with one copy loss. The right peak (relative to central one) represents regions with one copy amplification.

The fractional concentration of tumor-derived DNA can be reflected by the distance between the peaks representing the amplified and deleted regions. The larger the distance, the higher the fractional concentration of the tumor-derived DNA in the sample would be. The fractional concentration of tumor-derived DNA in the sample can be determined by this genomic representation approach, denoted as $F_{GR}$, using the following equation: $F_{GR}=R_{right}-R_{left}$, where $R_{right}$ is the R value of the right peak and $R_{left}$ is the R value of the left peak. The largest difference would be 1, corresponding to 100%. The fractional concentration of tumor-derived DNA in the tumor sample obtained from the HCC patient is estimated to be 66%, where the values of $R_{right}$ and $R_{left}$ are 1.376 and 0.712, respectively.

To verify this result, another method using the genomewide aggregated allele loss (GAAL) analysis was also used to independently determine the fractional concentration of proportion of tumoral DNA (Chan K C et al. Clin Chem 2013; 59:211-24). Table 3 shows the fractional concentrations of tumor-derived DNA in the tumor tissues of the four HCC patients using the genomic representation ($F_{GR}$) and the GAAL ($F_{GAAL}$) approaches. The values determined by these two different approaches agree well with each other.

| HCC tumor | $F_{GAAL}$ | $F_{GR}$ |
|---|---|---|
| 1 | 60.0% | 66.5% |
| 2 | 60.0% | 61.4% |
| 3 | 58.0% | 58.9% |
| 4 | 45.7% | 42.2% |

Table 3 showing fractional concentration determined by GAAL and genomic representation (GR).

2. Estimation in Sample with Low Tumor Concentration

The above analysis has shown that our genomic representation method can be used to measure the fractional concentration of tumor DNA when more than 50% of the sample DNA is tumor-derived, i.e. when the tumor DNA is a majority proportion. In the previous analysis, we have shown that this method can also be applied to samples in which the tumor-derived DNA represents a minor proportion (i.e., below 50%). Samples that may contain a minor proportion of tumor DNA include, but not limited to blood, plasma, serum, urine, pleural fluid, cerebrospinal fluid, tears, saliva, ascitic fluid and feces of cancer patients. In some samples, the fractional concentration of tumor-derived DNA can be 49%, 40%, 30%, 20%, 10%, 5%, 2%, 1%, 0.5%, 0.1% or lower.

For such samples, the peaks of sequence read density representing the regions with amplification and deletion may not be as obvious as in samples containing a relatively high concentration of tumor-derived DNA as illustrated above. In one embodiment, the regions with chromosomal aberrations in the cancer cells can be identified by making comparison to reference samples which are known to not contain cancer DNA. For example, the plasma of subjects without a cancer can be used as references to determine the normative range of sequence read densities for the chromosome regions. The sequence read density of the tested subject can be compared with the value of the reference group. In one embodiment, the mean and standard deviation (SD) of sequence read density can be determined. For each bin, the sequence read density of the tested subject is compared with the mean of the reference group to determine the z-score using the following formula:

$$z\text{-score} = \frac{(GR_{test} - \overline{GR}_{ref})}{SD_{ref}},$$

where $GR_{test}$ represents the sequence read density of the cancer patient; $\overline{GR}_{ref}$ represents the mean sequence read density of the reference subjects and $SD_{ref}$ represents the SD of the sequence read densities for the reference subjects.

Regions with z-score <−3 signifies significant underpresentation of the sequence read density for a particular bin in the cancer patient suggesting the presence of a deletion in the tumor tissue. Regions with z-score >3 signifies significant overpresentation of the sequence read density for a particular bin in the cancer patient suggesting the presence of an amplification in the tumor tissue Then, the distribution of the z-scores of all the bins can be constructed to identify regions with different numbers of copy gain and loss, for example, deletion of 1 or 2 copies of a chromosome; and amplification, resulting in of 1, 2, 3 and 4 additional copies of a chromosome. In some cases, more than one chromosome or more than one regions of a chromosome may be involved.

Figure 10B:
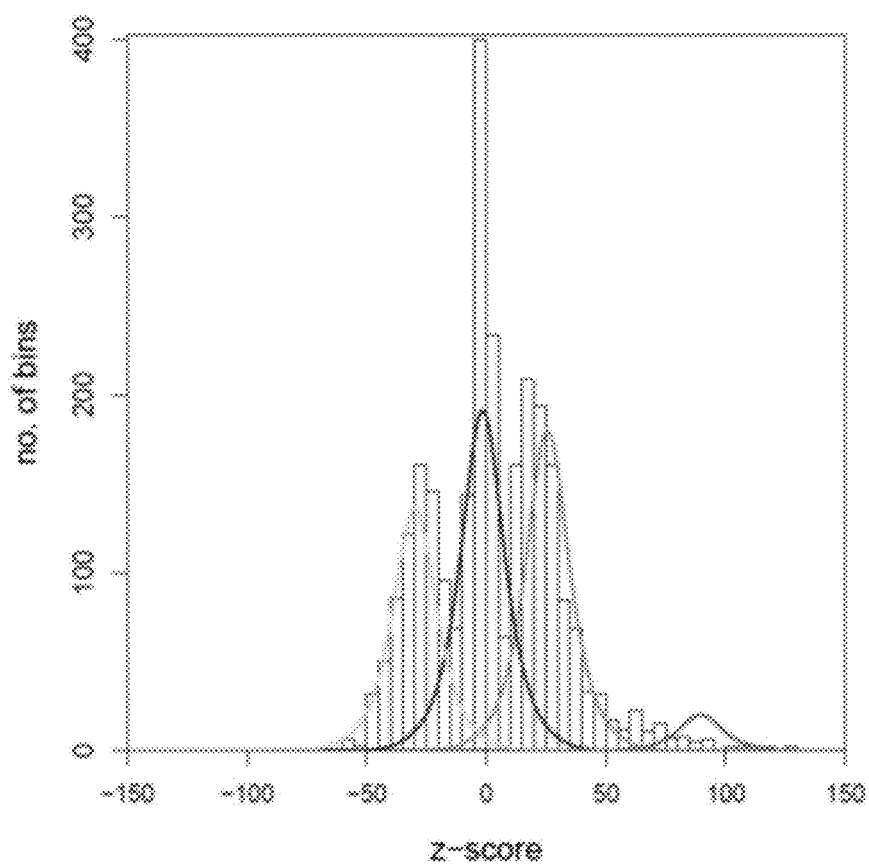
FIG. 10B shows a distribution plot 1050 of z-scores for all the bins in the plasma of a HCC patient according to embodiments of the present invention.

FIG. 10B shows a distribution plot 1050 of z-scores for all the bins in the plasma of a HCC patient according to embodiments of the present invention. The peaks (from left to right) representing 1-copy loss, no copy change, 1-copy gain and 2-copy gain are fitted to the z-score distribution. Regions with different types of chromosomal aberrations can then be identified, for example using the normal mixture model as described above.

The fractional concentration of the cancer DNA in the sample (F) can then be inferred from the sequence read densities of the bins that exhibit one-copy gain or one-copy loss. The fractional concentration determined for a particular bin can be calculated as $$F = \frac{|GR_{test} - \overline{GR}_{ref}| \times 2}{\overline{GR}_{ref}} \times 100\%.$$

This can also be expressed as:

$$F = \frac{|z\text{-score} \times SD_{ref}|}{\overline{GR}_{ref}} \times 2,$$

which can be rewritten as: $F=|z-\text{score}|\times CV\times 2$, where CV is the coefficient of variation for the measurement of the sequence read density of the reference subjects; and $$CV = \frac{SD_{ref}}{\overline{GR}_{ref}}.$$

In one embodiment, the results from the bins are combined. For example, the z-scores of bins showing a 1-copy gain can be averaged or the resulting F values averaged. In another implementation, the value of the z-score used for inferring F is determined by a statistical model and is represented by the peaks shown in FIG. 10B and FIG. 11. For example, the z-score of the right peak can be used to determine the fractional concentration for the regions exhibiting 1-copy gain.

In another embodiment, all bins with z-score <−3 and z-score >3 can be attributed to regions with single copy loss and single copy gain, respectively, because these two types of chromosomal aberrations are the most common. This approximation is most useful when the number of bins with chromosomal aberrations is relatively small and fitting of normal distribution may not be accurate.

Figure 11:
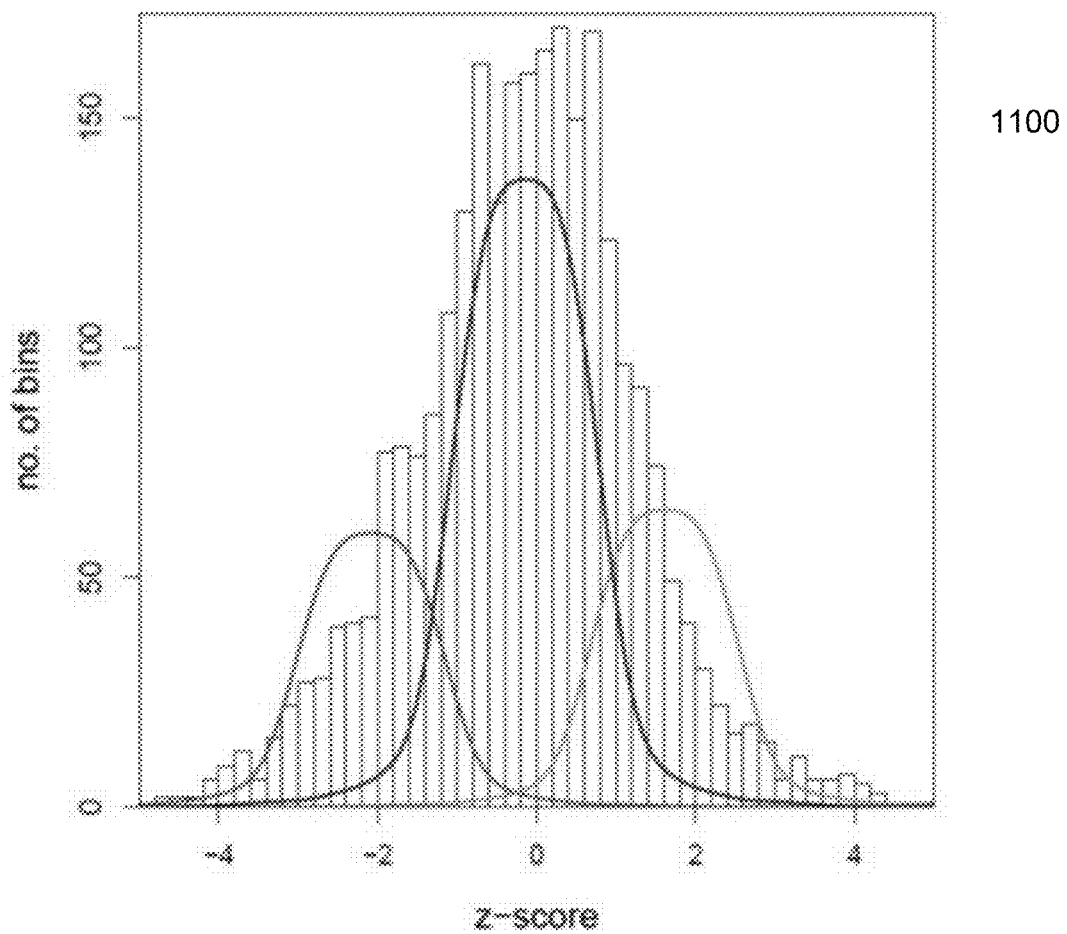
FIG. 11 shows a distribution plot 1100 of z-scores for the plasma of an HCC patient according to embodiments of the present invention.

FIG. 11 shows a distribution plot 1100 of z-scores for the plasma of an HCC patient according to embodiments of the present invention. While the number of bins overlapping with chromosomal aberrations is relatively small, all bins with z-score <−3 and z-score >3 were fitted to the normal distributions of single copy loss and single copy gain, respectively.

The fractional concentrations of tumor-derived DNA in the plasma of the four HCC patients were determined using GAAL analysis and this GR-based approach. The results are shown in Table 4. As can be seen, the deduced fractional representation correlates well between the GAAL analysis and the GR analysis.

TABLE 4

Fractional concentration of tumor-derived DNA in plasma deduced by the analysis of chromosomal aberrations.

| Samples | Fractional concentration of tumor-derived DNA in plasma | |
|---|---|---|
| | GAAL analysis | GR analysis |
| case11 | 4.3% | 4.5% |
| case13 | 5% | 5.5% |
| case23 | 52% | 62% |
| case27 | 7.6% | 6.1% |

C. Method of Determining Fractional Concentration

Figure 12:
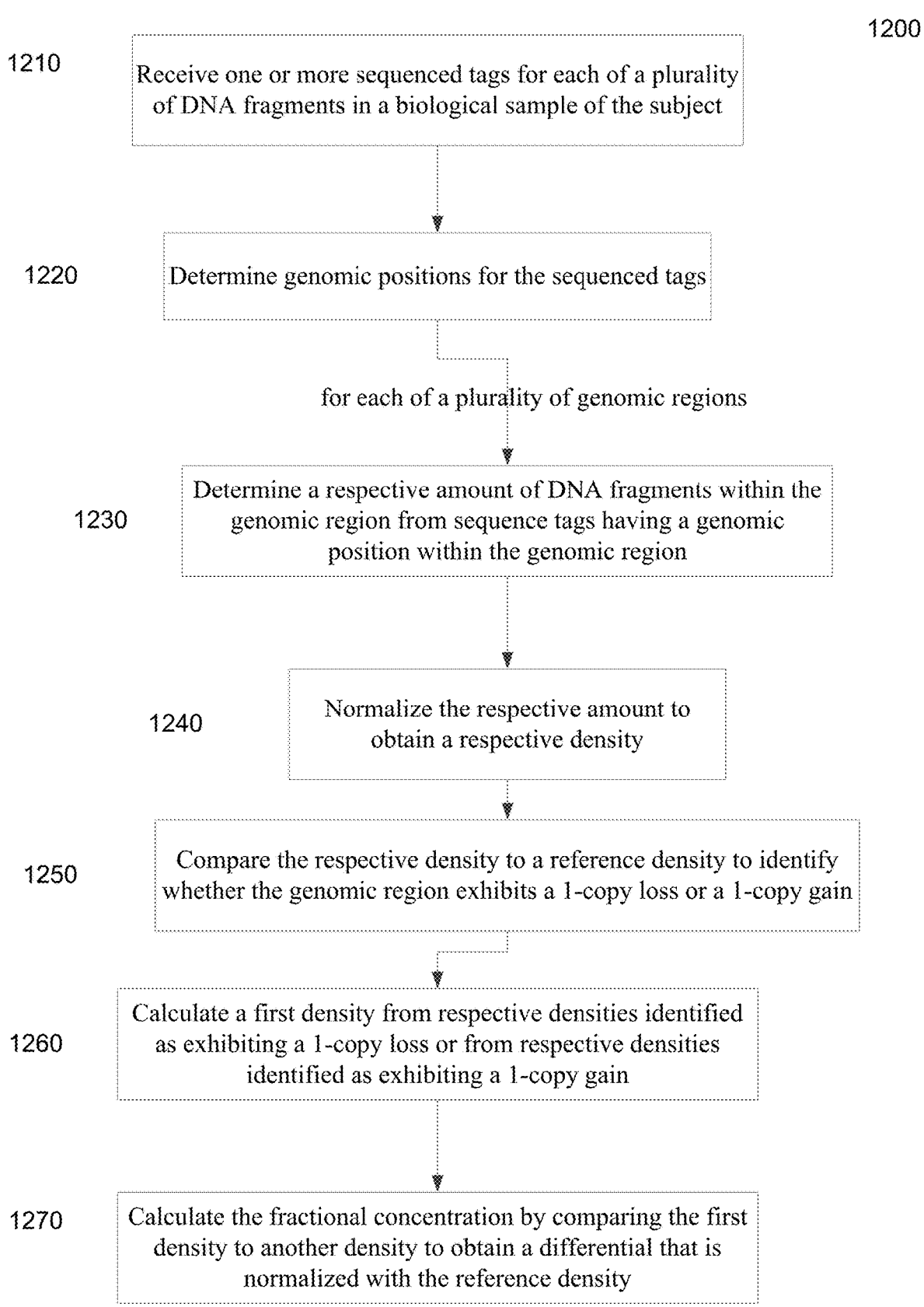
FIG. 12 is a flowchart of a method 1200 of determining a fractional concentration of tumor DNA in a biological sample including cell-free DNA according to embodiments of the present invention.

FIG. 12 is a flowchart of a method 1200 of determining a fractional concentration of tumor DNA in a biological sample including cell-free DNA according to embodiments of the present invention. Method 1200 may be performed via various embodiments, including embodiments described above.

At block 1210, one or more sequence tags are received for each of a plurality of DNA fragments in the biological sample. Block 1210 may be performed as described herein for other methods. For example, one end of a DNA fragment may be sequenced from a plasma sample. In another embodiment, both ends of a DNA fragment may be sequenced, thereby allowing a length of the fragment to be estimated.

At block 1220, genomic positions are determined for the sequence tags. The genomic positions can be determined, e.g., as described herein by aligning the sequence tags to a reference genome. If both ends of a fragment are sequenced, then the paired tags may be aligned as a pair with a distance between the two tags constrained to be less than a specified distance, e.g., 500 or 1,000 bases.

At block 1230, for each of a plurality of genomic regions, a respective amount of DNA fragments within the genomic region is determined from sequence tags having a genomic position within the genomic region. The genomic regions may be non-overlapping bins of equal length in the reference genome. In one embodiment, a number of tags that align to a bin can be counted. Thus, each bin can have a corresponding number of aligned tags. A histogram can be computed illustrating a frequency that bins have a certain number of aligned tags. Method 1200 may be performed for genomic regions each having a same length (e.g., 1 Mb bins), where the regions are non-overlapping. In other embodiments, different lengths can be used, which may be accounted for, and the regions may overlap.

At block 1240, the respective amount is normalized to obtain a respective density. In one embodiment, normalizing the respective amount to obtain a respective density includes using a same total number of aligned reference tags to determine the respective density and the reference density. In another embodiment, the respective amount can be divided by a total number of aligned reference tags.

At block 1250, the respective density is compared to a reference density to identify whether the genomic region exhibits a 1-copy loss or a 1-copy gain. In one embodiment, a difference is computed between the respective density and the reference density (e.g., as part of determining a z-score) and compared to a cutoff value. In various embodiments, the reference density can be obtained from a sample of healthy cells (e.g., from the buffy coat) or from the respective amounts themselves (e.g., by taking an median or average value, under an assumption that most regions do not exhibit a loss or a gain).

At block 1260, a first density is calculated from one or more respective densities identified as exhibiting a 1-copy loss or from one or more respective densities identified as exhibiting a 1-copy gain. The first density can correspond to just one genomic region, or may be determined from densities of multiple genomic regions. For example, the first density may be computed from respective densities having a 1-copy loss. The respective densities provide a measure of the amount of the density difference resulting from the deletion of the region in a tumor, given the tumor concentration. Similarly, if the first density is from respective densities having a 1-copy gain, then a measure of the amount of density difference resulting from the duplication of the region in a tumor can be obtained. Sections above describe various examples of how the densities of multiple regions can be used to determine an average density to be used for the first density.

At block 1270, the fractional concentration is calculated by comparing the first density to another density to obtain a differential. The differential is normalized with the reference density, which may be done in block 1270. For example, the differential can be normalized with the reference density by dividing the differential by the reference density. In another embodiment, the differential can be normalized in earlier blocks.

In one implementation, the another density is the reference density, e.g., as in section 2 above. Thus, calculating the fractional concentration may include multiplying the differential by two. In another implementation, the another density is a second density calculated from respective densities identified as exhibiting a 1-copy loss (where the first density is calculated using respective densities identified as exhibiting a 1-copy gain), e.g., as described in section 1 above. In this case, the normalized differential can be determined by computing a first ratio (e.g., $R_{right}$) of the first density and the reference density and computing a second ratio ($R_{left}$) of the second density and the reference density, where the differential is between the first ratio and the second ratio. As described above, the identification of genomic region exhibiting a 1-copy loss or a 1-copy gain can be performed by fitting peaks to a distribution curve of a histogram of the respective densities.

In summary, embodiments can analyze the genomic representation of plasma DNA in different chromosomal regions to simultaneously determine if the chromosomal region is amplified or deleted in the tumor tissue and, if the region is amplified or deleted, to use its genomic representation to deduce the fractional concentration of the tumor-derived DNA. Some implementations use a normal mixture model to analyze the overall distribution of the genomic representation of different regions so as to determine the genomic representation associated with different types of aberrations, namely gains of 1, 2, 3 or 4 copies and the losses of 1 or 2 copies.

Embodiments have several advantages over other methods, for example genomewide aggregated allelic loss (GAAL) approach (U.S. patent application Ser. No. 13/308, 473; Chan K C et al. Clin Chem 2013; 59:211-24) and the analysis of tumor-associated single nucleotide mutations (Forshew T et al. Sci Transl Med. 2012; 4:136ra68). All sequence reads mapping to regions with chromosomal aberrations can be used to determine the sequence read density of the region and, hence, are informative regarding the fractional concentration of tumoral DNA. On the other hand, in GAAL analysis, only sequence reads covering single nucleotides that are heterozygous in the individual and located within a chromosomal region with chromosome gain or loss would be informative. Similarly, for the analysis of cancer-associated mutations, only sequence reads covering the mutations would be useful for the deduction of the tumoral DNA concentration. Therefore, embodiments can allow a more cost-effective use of the sequencing data as relatively fewer sequencing reads may be needed to achieve the same degree of accuracy in the estimation of fractional concentration of tumor-derived DNA when compared with other approaches.

X. ALTERNATIVE METHODOLOGIES

Apart from using the number of times that a particular mutation is seen on a sequence tag as a criteria for identifying a locus as being a true mutation (thereby adjusting the positive predictive value), one could employ other techniques instead of or in addition to using a cutoff value to provide greater predictive value in identifying a cancerous mutation. For example, one could use bioinformatics filters of different stringencies when processing the sequencing data, e.g., by taking into account the quality score of a sequenced nucleotide. In one embodiment, one could use DNA sequencers and sequencing chemistries with different sequencing error profiles. Sequencers and chemistries with lower sequencing error rates would give a higher positive predictive values. One can also use repeated sequencing of the same DNA fragment to increase the sequencing accuracy. One possible strategy is the circular consensus sequencing strategy of Pacific Biosciences.

In another embodiment, one could incorporate size information on the sequenced fragments into the interpretation of the data. As tumor-derived DNA is shorter than the non-tumor-derived DNA in plasma (see U.S. patent application Ser. No. 13/308,473), the positive predictive value of a shorter plasma DNA fragment containing a potential tumor-derived mutation will be higher than that of a longer plasma DNA fragment. The size data will be readily available if one performs paired-end sequencing of the plasma DNA. As an alternative, one could use DNA sequencers with long read lengths, thus yielding the complete length of a plasma DNA fragment. One could also perform size fractionation of the plasma DNA sample prior to DNA sequencing. Examples of methods that one could use for size fractionation include gel electrophoresis, the use of microfluidics approach (e.g. the Caliper LabChip XT system) and size-exclusion spin columns.

In yet another embodiment, the fractional concentration of tumor-associated mutations in plasma in a patient with non-hematologic cancer would be expected to increase if one focuses on the shorter DNA fragments in plasma. In one implementation, one can compare the fractional concentration of tumor-associated mutations in plasma in DNA fragments of two or more different size distributions. A patient with a non-hematologic cancer will have higher fractional concentrations of tumor-associated mutations in the shorter fragments when compared with the larger fragments.

In some embodiments, one could combine the sequencing results from two or more aliquots of the same blood sample, or from two or more blood samples taken on the same occasions or on different occasions. Potential mutations seen in more than one aliquot or samples would have a higher positive predictive value of tumor-associated mutations. The positive predictive value would increase with the number of samples that show such a mutation. The potential mutations that are present in plasma samples taken at different time points can be regarded as potential mutations.

XI. EXAMPLES

The following are example techniques and data, which should not be considered limiting on embodiments of the present invention.

A. Materials and Methods

Regarding sample collection, hepatocellular carcinoma (HCC) patients, carriers of chronic hepatitis B, and a patient with synchronous breast and ovarian cancers were recruited. All HCC patients had Barcelona Clinic Liver Cancer stage A1 disease. Peripheral blood samples from all participants were collected into EDTA-containing tubes. The tumor tissues of the HCC patients were obtained during their cancer resection surgeries.

Peripheral blood samples were centrifuged at 1,600 g for 10 min at 4° C. The plasma portion was recentrifuged at 16,000 g for 10 min at 4° C. and then stored at 80° C. Cell-free DNA molecules from 4.8 mL of plasma were extracted according to the blood and body fluid protocol of the QIAamp DSP DNABlood Mini Kit (Qiagen). The plasma DNA was concentrated with a SpeedVac Concentrator (Savant DNA120; Thermo Scientific) into a 40-μl final volume per case for subsequent preparation of the DNA-sequencing library Genomic DNA was extracted from patients' buffy coat samples according to the blood and body fluid protocol of the QIAamp DSP DNA Blood Mini Kit. DNA was extracted from tumor tissues with the QIAamp DNA Mini Kit (Qiagen).

Sequencing libraries of the genomicDNAsamples were constructed with the Paired-End Sample Preparation Kit (Illumina) according to the manufacturer's instructions. In brief, 1-5 micrograms of genomic DNA was first sheared with a Covaris S220 Focused-ultrasonicator to 200-bp fragments. Afterward, DNA molecules were end-repaired with T4 DNA polymerase and Klenow polymerase; T4 polynucleotide kinase was then used to phosphorylate the 5' ends. A 3' overhang was created with a 3'-to-5' exonuclease-deficient Klenow fragment. Illumina adapter oligonucleotides were ligated to the sticky ends. The adapter-ligated DNA was enriched with a 12-cycle PCR. Because the plasma DNA molecules were short fragments and the amounts of total DNA in the plasma samples were relatively small, we omitted the fragmentation steps and used a 15-cycle PCR when constructing the DNA libraries from the plasma samples.

An Agilent 2100 Bioanalyzer (Agilent Technologies) was used to check the quality and size of the adapter-ligated DNA libraries. DNA libraries were then measured by a KAPA Library Quantification Kit (Kapa Biosystems) according to the manufacturer's instructions. The DNA library was diluted and hybridized to the paired-end sequencing flow cells. DNA clusters were generated on a cBot cluster generation system (Illumina) with the TruSeq PE Cluster Generation Kit v2 (Illumina), followed by 51_2 cycles or 76_2 cycles of sequencing on a HiSeq 2000 system (Illumina) with the TruSeq SBS Kit v2 (Illumina).

The paired-end sequencing data were analyzed by means of the Short Oligonucleotide Alignment Program 2 (SOAP2) in the paired-end mode. For each paired-end read, 50 bp or 75 bp from each end was aligned to the non-repeat-masked reference human genome (hg18). Up to 2 nucleotide mismatches were allowed for the alignment of each end. The genomic coordinates of these potential alignments for the 2 ends were then analyzed to determine whether any combination would allow the 2 ends to be aligned to the same chromosome with the correct orientation, spanning an insert size less than or equal to 600 bp, and mapping to a single location in the reference human genome. Duplicated reads were defined as paired-end reads in which the insert DNA molecule showed identical start and end locations in the human genome; the duplicate reads were removed as previously described (Lo et al. *Sci Transl Med* 2010; 2: 61ra91).

In some embodiments, the paired tumor and constitutional DNA samples were sequenced to identify the tumor-associated single nucleotide variants (SNVs). In some implementations, we focused on the SNVs occurring at homozygous sites in the constitutional DNA (in this example being the buffy coat DNA). In principle, any nucleotide variation detected in the sequencing data of the tumor tissues but absent in the constitutional DNA could be a potential mutation (i.e., a SNV). Because of sequencing errors (0.1%-0.3% of sequenced nucleotides), however, millions of false positives would be identified in the genome if a single occurrence of any nucleotide change in the sequencing data of the tumor tissue were to be regarded as a tumor-associated SNV. One way to reduce the number of false positives would be to institute the criterion of observing multiple occurrences of the same nucleotide change in the sequencing data in the tumor tissue before a tumor associated SNV would be called.

Because the occurrence of sequencing errors is a stochastic process, the number of false positives due to sequencing errors would decrease exponentially with the increasing number of occurrences required for an observed SNV to be qualified as a tumor-associated SNV. On the other hand, the number of false positives would increase with increasing sequencing depth. These relationships could be predicted with Poisson and binomial distribution functions. Embodiments can determine a dynamic cutoff of occurrence for qualifying an observed SNV as tumor associated. Embodiments can take into account the actual coverage of the particular nucleotide in the tumor sequencing data, the sequencing error rate, the maximum false-positive rate allowed, and the desired sensitivity for mutation detection.

In some examples, we set very stringent criteria to reduce false positives. For example, a mutation may be required to be completely absent in the constitutional DNA sequencing, and the sequencing depth for the particular nucleotide position had to be 20-fold. In some implementations, the cutoff of occurrence achieved a false-positive detection rate of less than $10^{-7}$. In some examples, we also filtered out SNVs that were within centromeric, telomeric, and low-complexity regions to minimize false positives due to alignment artifacts. In addition, putative SNVs mapping to known SNPs in the dbSNP build 135 database were also removed.

B. Before and after Resection

FIG. 13A shows a table 1300 of the analysis of mutations in the plasma of the patient with ovarian cancers and a breast cancer at the time of diagnosis according to embodiments of the present invention. Here, we demonstrate an example for a patient with bilateral ovarian cancers and a breast cancer. The sequencing data of the plasma were compared to the sequencing results of the constitutional DNA of the patient (buffy coat). Single nucleotide changes that were present in the plasma but not in the constitutional DNA were regarded as potential mutations. The ovarian cancers on the right and left side of the patient were each sampled at two sites, making a total of four tumor samples. The tumor mutations were mutations detected in all the four ovarian tumor tissues at four different sites.

Over 3.6 million single nucleotide changes were detected in the plasma for at least one time by sequencing. Among these changes, only 2,064 were also detected in the tumor tissues giving a positive prediction value of 0.06%. Using the criterion of being detected at least two times in plasma, the number of potential mutations was significantly reduced by 99.5% to 18,885. The number of tumor mutations was only reduced by 3% to 2,003, and the positive prediction value increased to 11%.

Using the criteria of detecting at least five times in plasma, only 2,572 potential mutations were detected and amongst them, 1,814 were mutations detected in all the tumor tissues, thus, giving a positive predictive value of 71%. Other criteria for the number of occurrences (e.g. 2, 3, 4, 6, 7, 8, 9, 10, etc.) can be used for defining potential mutations depending on the sensitivity and positive predictive value required. The higher the number of occurrences is used as the criterion, the higher the positive predictive value would be with a reduction in the sensitivity.

FIG. 13B shows a table 1350 of the analysis of mutations in the plasma of the patient with bilateral ovarian cancers and a breast cancer after tumor resection according to embodiments of the present invention. Surgical resection of the patient was performed. A blood sample was taken one day after the resection of the ovarian tumors and the breast cancer. The plasma DNA was then sequenced. For this example, only the mutations from the ovarian cancers were analyzed. Over 3 million potential mutations were detected at least once in a plasma sample. However, using a criterion of having at least five occurrences, the number of potential mutations was reduced to 238. A significant reduction was observed when compared with the number of potential mutations for the sample taken at diagnosis and using the same criterion of five mutations.

In one embodiment, the number of single nucleotide changes detected in plasma can be used as a parameter for the detection, monitoring and prognostication of a cancer patient. Different number of occurrences can be used as the criterion to achieve the desired sensitivity and specificity. A patient with a higher tumor load and thus worse prognosis will be expected to have a higher mutational load seen in plasma.

For such analysis, one could establish the mutational load profile for different types of cancer. For monitoring purposes, one would see that the mutational load in plasma of a patient who responds to treatment would reduce. If the tumor has recurred, e.g. during a relapse, then the mutational load will be expected to increase. Such monitoring would allow one to monitor the efficacy of the selected modality of treatment for a patient and to detect the emergence of resistance to a particular treatment.

Through the analysis of the specific mutations that one could see in the plasma DNA sequencing results, one could also identify targets that would predict sensitivity (e.g. mutations in the epidermal growth factor receptor gene and response to tyrosine kinase inhibitor treatment) and resistance to particular targeted treatment (e.g. KRAS mutations in colorectal cancer and resistance to treatment by panitumumab and cetuximab), and could guide the planning of treatment regimes.

The example above was for the bilateral ovarian cancers. One could also perform the same analysis on the mutations of the breast cancer and then would be able to track the mutations of both of these cancer types in the plasma. One can also use a similar strategy to track the mutations of a primary cancer and its metastasis or metastases.

Embodiments would be useful to the screening of cancer in apparently healthy subjects or in subjects with particular risk factors (e.g. smoking status, viral status (such as hepatitis virus carriers, human papillomavirus infected subjects)). The mutational load that one could see in the plasma of such subjects would give a risk that the subject would develop symptomatic cancer within a particular timeframe. Thus, subjects with a higher mutational load in plasma would be expected to have a higher risk than those with a lower mutational load. Furthermore, the temporal profile of such mutational load in plasma would also be a powerful indicator of risk. For example, if a subject has one plasma mutational load performed each year and if the mutational loads are progressively increasing, then this subject should be referred for additional screening modalities for cancer, e.g. using chest X ray, ultrasound, computed tomography, magnetic resonance imaging or positron emission tomography.

C. Dynamic Cutoffs to Deduce Mutations from Sequencing Plasma

Four patients with hepatocellular carcinoma (HCC) and one patient with ovarian and breast cancer were recruited for this study. For the latter patient, we focused on the analysis of the ovarian cancer. Blood samples were collected from each patient before and after surgical resection of the tumors. The resected tumor tissues were also collected. The DNA extracted from the tumor tissue, the white blood cells of the preoperative blood sample and the pre- and postoperative plasma samples was sequenced using the HiSeq2000 sequencing system (Illumina). The sequencing data were aligned to the reference human genome sequence (hg18) using Short Oligonucleotide Analysis Package 2 (SOAP2) (Li R et al. Bioinformatics 2009; 25: 1966-1967). The DNA sequences of the white blood cells were regarded as constitutional DNA sequence for each study subject.

In this example, tumor-associated SNMs were first deduced from the plasma DNA sequencing data and the CG without reference to the tumor tissues. Then, the deduced results from plasma were compared with sequencing data generated from the tumor tissues (as a gold standard) to ascertain the accuracy of the deduced results. In this regard, the gold standard was made by comparing sequencing data from the tumor tissues and the constitutional sequence to work out the mutations in the tumor tissues. In this analysis, we focused on nucleotide positions at which the constitutional DNA of the studied subject was homozygous.

1. Non-Targeted Whole Genome Analysis

The sequencing depths for the white cells, the tumor tissues and the plasma DNA of each patient are shown in Table 5.

TABLE 5

Median sequencing depths of different samples for the four HCC cases.

| | Median sequencing depth (folds) | | | |
|---|---|---|---|---|
| Case | White blood cells | Tumor tissue | Preoperative plasma | Postoperative plasma |
| HCC1 | 39 | 29 | 23 | 24 |
| HCC2 | 39 | 29 | 25 | 28 |
| HCC3 | 46 | 33 | 18 | 21 |
| HCC4 | 46 | 27 | 20 | 23 |
| Ovarian cancer patient | 44 | 53 | 37 | 28 |

The dynamic cutoffs for the minimum occurrences for defining plasma mutations (r) as shown in table 1 are used for identifying the mutations in the plasma of each patient. As the sequencing depth of each locus may vary, the cutoff may vary, which effectively provides a dependence of the cutoff on the total number of reads for a locus. For example, although the median depth is less than 50 (Table 5), the sequencing depth of individual loci can vary a lot and be covered >100 times.

In addition to sequencing errors, another source of error would be alignment errors. To minimize this type of errors, the sequence reads carrying a mutation was realigned to the reference genome using the Bowtie alignment program (Langmead B et al. Genome Biol 2009, 10:R25). Only reads that could be aligned to a unique position of the reference genome by SOAP2 and Bowtie were used for the downstream analysis for plasma mutations. Other combinations of alignment software packages based on different algorithms could also be used.

In order to further minimize the sequencing and alignment errors in the actual sequencing data, we applied two additional filtering algorithms for calling the nucleotide positions which showed single nucleotide variations in the sequence reads: (1) ≥70% of the sequence reads carrying the mutation could be realigned to the same genomic coordinate using Bowtie with mapping quality ≥Q20 (i.e. misalignment probability <1%); (2) ≥70% of the sequence reads carrying the mutation were not within 5 bp of both ends (i.e. 5' and 3' ends) of the sequence reads. This filtering rule was instituted because sequencing errors were more prevalent at both ends of a sequence read.

We also investigated the factors affecting the deducing of a tumor without prior knowledge of the tumor genome. One such parameter was the fractional concentration of tumor-derived DNA in plasma. This parameter could be regarded as another gold standard parameter and was deduced for reference purpose with prior knowledge of the tumor genome using GAAL.

Table 6 shows nucleotide variations detected in plasma before and over treatment. For HCC1, without prior knowledge of the tumor genome, a total of 961 single nucleotide variations were detected. Amongst these nucleotide variations detected in plasma, 828 were cancer-associated mutations. After surgical resection of the HCC, the total number of nucleotide variations was reduced to 43 and none of them was cancer-associated mutations.

For reference purposes, the fractional concentration of tumor-derived DNA in the pre-operative plasma sample was 53% and was deduced with prior knowledge of the tumor genome. For HCC2, HCC3 and HCC4, without prior knowledge of the tumor genomes, the numbers of single nucleotide variations in plasma were deduced as ranging from 27 to 32 for the pre-operative plasma samples. These results are compatible with the mathematical prediction that, with a sequencing depth of approximately 20-fold, a very low percentage of cancer-associated mutations could be detected in the plasma and most of the sequence variations detected in the plasma were due to sequencing errors. After tumor resection, there was no significant change in the number of sequence variations detected. For reference purposes, the fractional concentrations of tumor-derived DNA in plasma were deduced as ranging from 2.1% to 5% and were deduced with prior knowledge of the tumor genomes.

TABLE 6

| | Pre-operative plasma | | | Post-operative plasma | | |
|---|---|---|---|---|---|---|
| | Fractional concentration of tumor-derived DNA | Total no. of single nucleotide variations | No. of cancer-associated mutations identified | Fractional concentration of tumor-derived DNA | Total no. of single nucleotide variations | No. of cancer-associated mutations identified |
| HCC1 | 53% | 961 | 828 | 0.4% | 43 | 0 |
| HCC2 | 5% | 32 | 0 | 0.6% | 49 | 0 |
| HCC3 | 2.1% | 29 | 0 | 0.2% | 32 | 0 |
| HCC4 | 2.6% | 27 | 0 | 1.3% | 35 | 1 |
| Ovarian (and breast) cancer patient | 46% | 1718 | 1502 | 0.2% | 2 | 0 |

2. Target Enrichment of the Exons

As discussed above, increasing the sequencing depth for the region-of-interest can increase both the sensitivity and specificity for identifying cancer-associated mutations in plasma and, hence, increasing the discrimination power between the cancer patients and non-cancer subjects. While the increase of sequencing depth for the whole genome is still very costly, one alternative is to enrich for certain regions for sequencing. In one embodiment, selected exons or indeed the whole exome can be target-enriched for sequencing. This approach can significantly increase the sequencing depth of the target region without increasing the total amount of sequence reads.

The sequencing libraries of the plasma DNA of the HCC patients and the patient with ovarian (and breast) cancer were captured using the Agilent SureSelect All Exon kit for target enrichment of the exome. The exon-enriched sequencing libraries were then sequenced using the HiSeq 2000 sequencing system. The sequence reads were aligned to the human reference genome (hg18). After alignment, sequence reads uniquely mapped to the exons were analyzed for single nucleotide variations. For the identification of single nucleotide variations in plasma for the exome capture analysis, the dynamic cutoff values shown in table 2 are used.

FIG. 14A is a table 1400 showing detection of single nucleotide variations in plasma DNA for HCC1. Without prior knowledge of the tumor genome, we deduced from the targeted sequencing data a total of 57 single nucleotide variations in plasma. In subsequent validation from the sequencing data obtained from the tumor tissues, 55 were found to be true tumor-associated mutations. As discussed before, fractional concentration of tumor-derived DNA in the pre-operative plasma was 53%. After tumor resection, no single nucleotide variations were detected in the targeted sequencing data obtained from the plasma. These results indicate that the quantitative analysis of the number of single nucleotide variations in plasma can be used for monitoring the disease progression of cancer patients.

FIG. 14B is a table 1450 showing detection of single nucleotide variations in plasma DNA for HCC2. Without prior knowledge of the tumor genome, we deduced from the targeted sequencing data of the plasma a total of 18 single nucleotide variations. All of these mutations were found in the tumor tissues. As discussed before, fractional concentration of tumor-derived DNA in the pre-operative plasma was 5%. After tumor resection, no single nucleotide variations were detected in the plasma. Compared with HCC1 which had a higher fractional concentration of tumor-derived DNA in plasma, fewer single nucleotide variations were detected in the plasma of the case involving HCC2. These results suggest that the number of single nucleotide variations in plasma can be used as a parameter to reflect the fractional concentration of tumor-derived DNA in plasma and, hence, the tumor load in the patient as it has been showed that the concentration of tumor-derived DNA in plasma is positively correlated with the tumor load (Chan K C et al. Clin Chem 2005; 51:2192-5).

FIG. 15A is a table 1500 showing detection of single nucleotide variations in plasma DNA for HCC3. Without prior knowledge of the tumor genome, we did not observe from the targeted sequencing data any single nucleotide variations in both the pre- and post-resection plasma samples. This is likely to be due to the relatively low fractional concentration (2.1%) of tumor-derived DNA in plasma in this patient. Further increase in the sequencing depth is predicted to improve the sensitivity for detecting cancer-associated mutations in cases with low fractional concentration of tumor-derived DNA.

FIG. 15B is a table 1550 showing detection of single nucleotide variations in plasma DNA for HCC4. Without prior knowledge of the tumor genome, we deduced from the targeted sequencing data of the plasma a total of 3 single nucleotide variations. All of these mutations were found in the tumor tissues. Compared with HCC1 and HCC2 which had higher fractional concentrations of tumor-derived DNA in plasma, fewer single nucleotide variations were detected in the plasma of case HCC4 which had a fractional tumor DNA in plasma of 2.6%. These results suggest that the number of single nucleotide variations in plasma can be used as a parameter to reflect the fractional concentration of tumor-derived DNA in plasma and tumor load in a patient.

FIG. 16 is a table 1600 showing detection of single nucleotide variations in plasma DNA for the patient with ovarian (and breast) cancer. Without prior knowledge of the tumor genome, we deduced from the targeted sequencing data of the plasma a total of 64 single nucleotide variations. Amongst these 59 were found in the ovarian tumor tissues. The estimated fractional concentration of ovarian tumor-derived DNA in the plasma was 46%. A significant reduction in the total number of single nucleotide variations were detected in plasma after resection of the ovarian cancer.

In addition to the use of the SureSelect target enrichment system (Agilent), we also used the Nimblegen SeqCap EZ Exome+UTR target enrichment system (Roche) for enriching sequences from exons for sequencing. The Nimblegen SeqCap system covers the exon regions of the genome as well as the 5' and 3' untranslated region. The pre-treatment plasma samples of the four HCC patients, two healthy control subjects and two chronic hepatitis B carriers without a cancer were analyzed (Table 7). In other embodiments, other target enrichment systems, including but not limited to those using solution phase or solid phase hybridization, can be used.

TABLE 7

Exome sequencing results for the four HCC patients (HCC1-4) using the Nimblegen SeqCap EZ Exome + UTR target enrichment system for sequence capture. The sequencing analysis of the pre-treatment plasma of HCC3 was sub-optimal due to a higher percentage of PCR-duplicated reads.

| | | Pre-treatment plasma | | Post-treatment plasma | |
|---|---|---|---|---|---|
| | Fractional concentration of tumor-derived DNA in plasma by GAAL analysis | No. of sequence variation detected in plasma fulfilling the dynamic cutoffs | No. of sequence variation that overlap with mutations detected in the corresponding tumor tissue | No. of sequence variation detected in plasma fulfilling the dynamic cutoffs | No. of sequence variation that overlap with mutations detected in the corresponding tumor tissue |
| HCC1 | 53% | 69 | 64 | 1 | 1 |
| HCC2 | 5% | 51 | 47 | 3 | 0 |
| HCC3 | 2.1% | 0 | 0 | 1 | 0 |
| HCC4 | 2.6% | 8 | 7 | 0 | 0 |

In the two chronic hepatitis B carriers and the two healthy control subjects, one or less single nucleotide variations that fulfilled the dynamic cutoff criteria were detected (Table 8). In three of the four HCC patients, the number of sequence variations detected in plasma that fulfilled the dynamic cutoff requirement was at least 8. In HCC3, no SNV that fulfilled the dynamic cutoff was detected. In this sample, there was a high proportion PCR-duplicated read in the sequenced reads leading to a lower number of non-duplicated sequenced reads. Marked reduction of SNVs detectable in plasma was observed after surgical resection of the tumor.

TABLE 8

Exome sequencing results for 2 chronic hepatitis B carriers (HBV1 and HBV2) and 2 healthy control subjects (Ctrl1 and Ctrl2) using the Nimblegen SeqCap EZ Exome + UTR target enrichment system for sequence capture.

| | No. of sequence variation detected in plasma fulfilling the dynamic cutoffs |
|---|---|
| HBV1 | 0 |
| HBV2 | 1 |
| Ctrl1 | 1 |
| Ctrl2 | 1 |

XII. TUMOR HETEROGENEITY

The quantification of single nucleotide mutations in a biological sample (e.g., plasma/serum) is also useful for the analysis of tumor heterogeneity, both intra-tumoral and inter-tumoral heterogeneity. Intra-tumoral heterogeneity relates to the existence of multiple clones of tumor cells within the same tumor. Inter-tumoral heterogeneity relates to the existence of multiple clones of tumor cells for two or more tumors of the same histologic type, but present in different sites (either in the same organs, or in different organs). In certain types of tumors, the existence of tumoral heterogeneity is a bad prognostic indicator (Yoon H H et al. J Clin Oncol 2012; 30: 3932-3938; Merlo L M F et al. Cancer Prev Res 2010; 3: 1388-1397). In certain types of tumors, the higher the degree of tumoral heterogeneity, the higher would be the chance of tumor progression or the development of resistant clones following targeted treatment.

Although cancers are believed to arise from the clonal expansion of one tumor cell, the growth and evolution of a cancer would lead to the accumulation of new and different mutations in different parts of a cancer. For example, when a cancer patient develops metastasis, the tumor located at the original organ and the metastatic tumor would share a number of mutations. However, the cancer cells of the two sites would also carry a unique set of mutations that are absent in the other tumor site. The mutations that are shared by the two sites are expected to be present at higher concentrations than those mutations that are only observed in one tumor site.

A. Example

We analyzed the blood plasma of a patient who had bilateral ovarian cancers and a breast cancer. Both ovarian tumors were serous adenocarcinoma. The left one measured 6 cm and the right one measured 12 cm in the longest dimension. There were also multiple metastatic lesions at the colon and the omentum. The DNA extracted from the leukocytes were sequenced using the sequencing-by-synthesis platform from Illumina to an average of 44-fold haploid genome coverage. The nucleotide locations showing only one allele, i.e. homozygous, were analyzed further for single nucleotide mutations in plasma.

DNA was extracted from four different sites of the left and right tumors and was sequenced using the Illumina sequencing platform. Two sites (sites A and B) were from the right tumor and the other two sites (sites C and D) were from the left tumor. Sites A and B were approximately 4 cm apart. The distance between sites C and D was also approximately 4 cm. Plasma samples were collected from the patient before and after surgical resection of the ovarian tumors. DNA was then extracted from the plasma of the patient. The sequencing depth of the tumor from sites A, B, C and D, as well as the plasma samples, are shown in the table 9.

TABLE 9

Sequencing depth of the tumor from sites A, B, C and D.

| Sample | No. of raw sequencing reads | No. of aligned reads | Folds of haploid genome coverage |
|---|---|---|---|
| Constitutional DNA from buffy coat | 1,091,250,072 | 876,269,922 | 43.81 |
| Right ovarian tumor (site A) | 1,374,495,256 | 1,067,277,229 | 53.36 |
| Right ovarian tumor (site B) | 934,518,588 | 803,007,464 | 40.15 |
| Left ovarian tumor (site C) | 1,313,051,122 | 1,036,643,946 | 51.83 |
| Left ovarian tumor (site D) | 1,159,091,833 | 974,823,207 | 48.74 |
| Plasma sample collected before | 988,697,457 | 741,982,535 | 37.10 |
| Plasma sample collected after | 957,295,879 | 564,623,127 | 28.23 |

In the current example, for defining a single tumor-associated single nucleotide mutation, the nucleotide location is sequenced at least 20 times in the tumor tissue and 30 times in the constitutional DNA. In other embodiments, other sequencing depths can be used, e.g. 35, 40, 45, 50, 60, 70, 80, 90, 100 and >100 folds. The reduction of sequencing costs would allow increased depths to be performed much more readily. The nucleotide position is homozygous in the constitutional DNA whereas a nucleotide change is observed in the tumor tissue. The criterion for the occurrence of the nucleotide change in the tumor tissue is dependent on the total sequencing depth of the particular nucleotide position in the tumor tissue. For nucleotide coverage from 20 to 30 folds, the occurrence of the nucleotide change (cutoff value) is at least five times. For coverage from 31 to 50 folds, the occurrence of the nucleotide change is at least six times. For coverage from 51 to 70 folds, the occurrence needs is at least seven times. These criteria are derived from the prediction of sensitivity of detecting the true mutations and the expected number of false positive loci using the Poisson distribution.

FIG. 17 is a table 1700 showing the predicted sensitivities of different requirements of occurrence and sequencing depths. The sensitivity would correspond to the number of true mutations detected at a particular fold depth using a particular cutoff. The higher sequencing depth, the more likely it is for a mutation to be detected for a given cutoff, as more mutation sequence reads will be obtained. For higher cutoff values, the less likely a mutant would be detected, since the criteria are more stringent.

FIG. 18 is a table 1800 showing the predicted numbers of false positive loci for different cutoffs and different sequencing depths. The number of false positives increases with increasing sequencing depth, as more sequence reads are obtained. However, no false positives are predicted for a cutoff of five or more, even up to a sequencing depth of 70. In other embodiments, different criteria of occurrence can be used so as to achieve the desired sensitivity and specificity.

Figure 19:
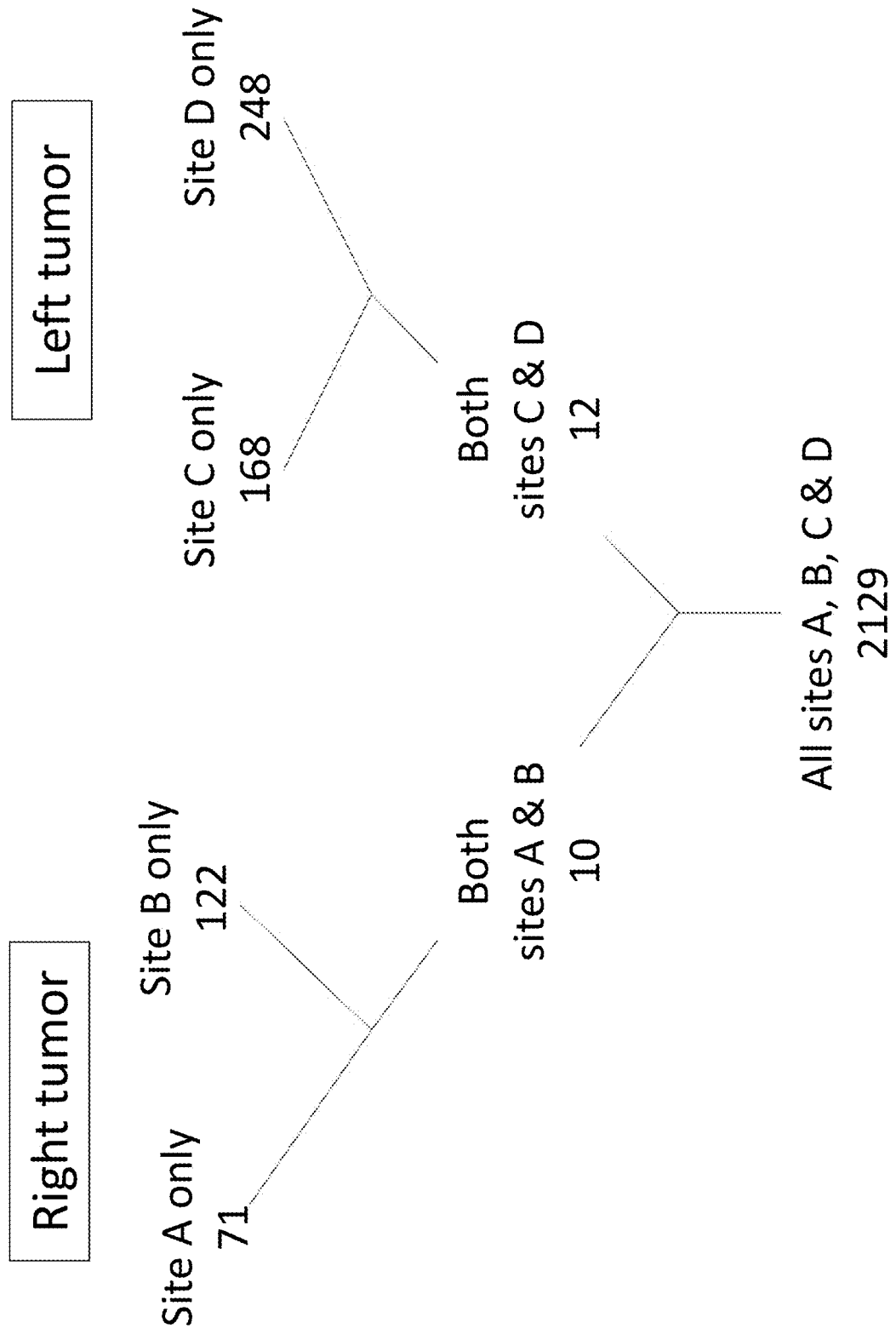
FIG. 19 shows a tree diagram illustrating the number of mutations detected in the different tumor sites.

FIG. 19 shows a tree diagram illustrating the number of mutations detected in the different tumor sites. The mutations were determined by sequencing the tumors directly. Site A has 71 mutations that are specific to that tumor, and site B has 122 site-specific mutations, even though they were only 4 cm apart. 10 mutations were seen in both sites A and B. Site C has 168 mutations that are specific to that tumor, and site D has 248 site-specific mutations, even though they were only 4 cm apart. 12 mutations were seen in both sites C and D. There is significant heterogeneity in the mutational profiles for the different tumor sites. For example, 248 mutations were only detected in the site D tumor but not detected in the other three tumor sites. A total of 2,129 mutations were seen across all sites. Thus, many mutations were shared among the different tumors. Thus, there were seven SNV groups. There were no observable differences among these four regions in terms of copy number aberrations FIG. 20 is a table 2000 showing the number of fragments carrying the tumor-derived mutations in the pre-treatment and post-treatment plasma sample. The inferred fractional concentrations of tumor-derived DNA carrying the respective mutations were also shown. The category of mutation refers to the tumor site(s) where the mutations were detected. For example, category A mutations refer to mutations only present in site A whereas category ABCD mutations refer to mutations present in all the four tumor sites.

For the 2,129 mutations that were present in all four tumor sites, 2,105 (98.9%) were detectable in at least one plasma DNA fragment. On the other hand, for the 609 mutations that were present in only one of the four tumor sites, only 77 (12.6%) were detectable in at least one plasma DNA fragment. Therefore, the quantification of single nucleotide mutations in plasma can be used for reflecting the relative abundance of these mutations in the tumor tissues. This information would be useful for the study of the cancer heterogeneity. In this example, a potential mutation was called when it had been seen once in the sequencing data.

The fractional concentrations of circulating tumor DNA were determined with each SNV group. The fractional concentrations of tumor DNA in plasma before surgery and after surgery, as determined by SNVs shared by all 4 regions (i.e., group ABCD), were 46% and 0.18%, respectively. These latter percentages correlated well with those obtained in GAAL analyses, 46% and 0.66%. Mutations that were shared by all 4 regions (i.e., group ABCD) contributed the highest fractional contribution of tumor-derived DNA to the plasma.

The fractional concentrations of tumor-derived DNA in preoperative plasma determined with SNVs from groups AB and CD were 9.5% and 1.1%, respectively. These concentrations were consistent with the relative sizes of the right and left ovarian tumors. The fractional concentrations of tumor-derived DNA determined with the region-unique SNVs (i.e., those in groups A, B, C, and D) were generally low. These data suggest that for an accurate measurement of the total tumor load in a cancer patient, the use of a genomewide shotgun approach might provide a more representative picture, compared with the more traditional approach of targeting specific tumor-associated mutations. For the latter approach, if only a subset of the tumor cells possesses the targeted mutations, one might miss important information regarding imminent relapse or disease progression caused by tumor cells not possessing the targeted mutations, or one might miss the emergence of a treatment-resistant clone.

Figure 21:
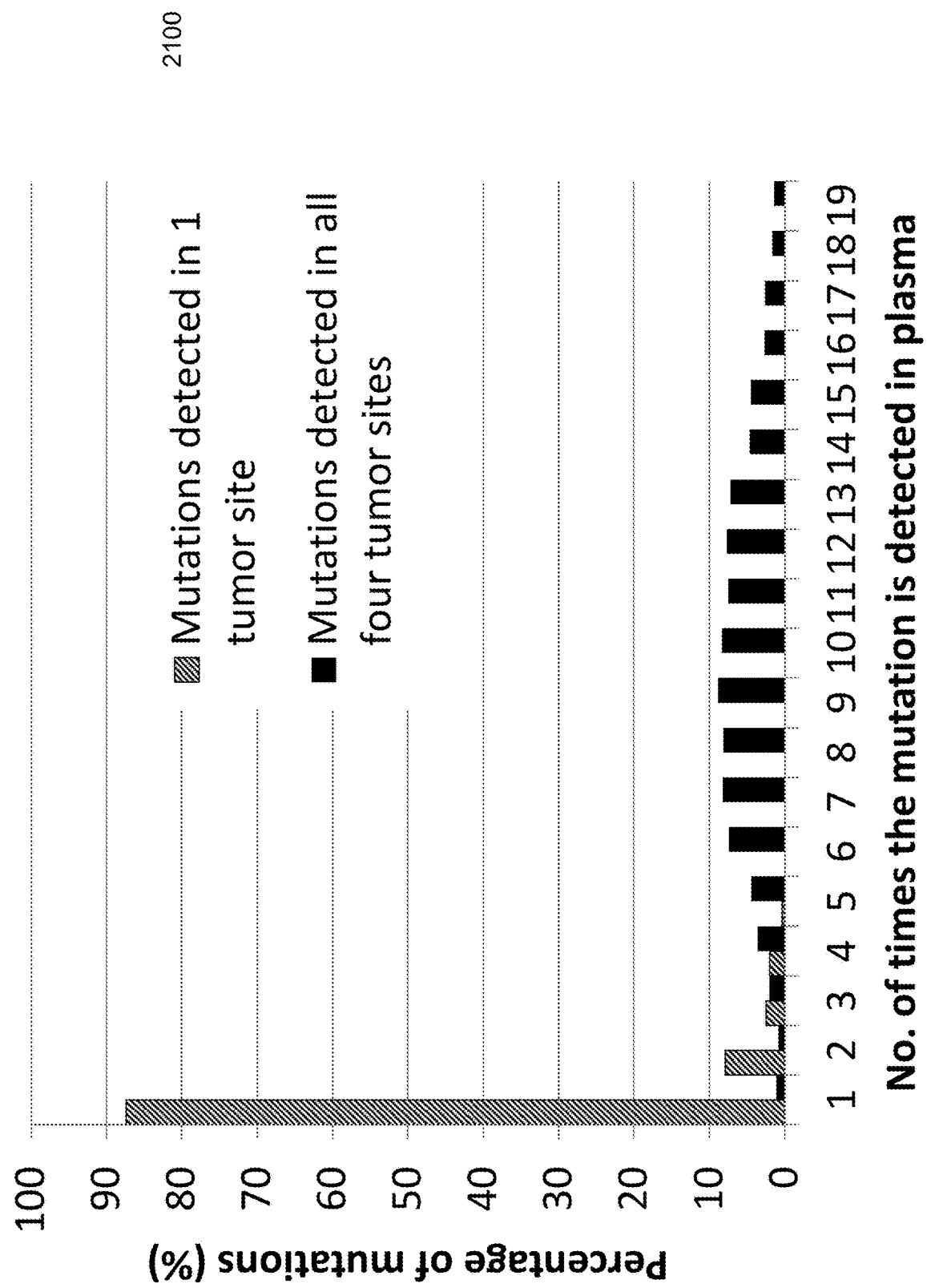
FIG. 21 is a graph 2100 showing distributions of occurrence in plasma for the mutations detected in a single tumor site and mutations detected in all four tumor sites.

FIG. 21 is a graph 2100 showing distributions of occurrence in plasma for the mutations detected in a single tumor site and mutations detected in all four tumor sites. The bar graph 2100 shows data for two types of mutation: (1) mutations detected in only one site and (2) mutations detected in all four tumor sites. The horizontal axis is the number of times that a mutation is detected in the plasma. The vertical axis shows the percentage of mutations that correspond to a particular value on the horizontal axis. For example, about 88% of type (1) mutations showed up only once in the plasma. As you can see, the mutations that showed up in one site were detected mostly once, and not more than four times. The mutations present in a single tumor site were much less frequently detected in the plasma compared with the mutations present in all four tumor sites.

One application of this technology would be to allow the clinicians to estimate the load of tumor cells carrying the different classes of mutations. A proportion of these mutations would potentially be treatable with targeted agents. Agents targeting mutations carried by a higher proportion of tumor cells would be expected to have a more prominent therapeutic effects.

Figure 22:
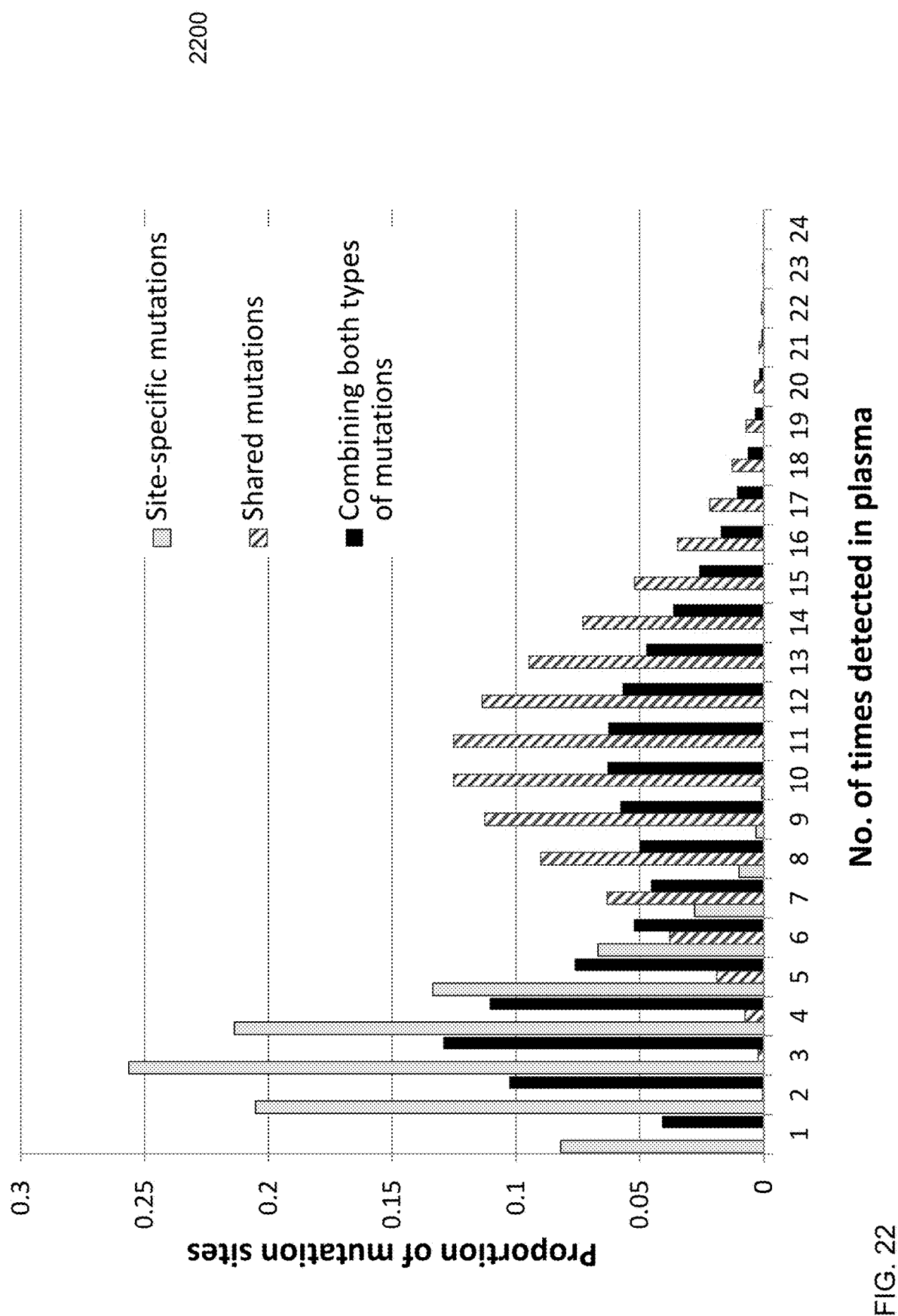
FIG. 22 is a graph 2200 showing predicted distribution of occurrence in plasma for mutations coming from a heterogeneous tumor FIG. 23 demonstrates the specificity of embodiments for 16 healthy control subjects were recruited.

FIG. 22 is a graph 2200 showing predicted distribution of occurrence in plasma for mutations coming from a heterogeneous tumor. The tumor contains two groups of mutations. One group of mutations are present in all tumor cells and the other group of mutations are only present in ¼ of the tumor cells, based on an approximation that two sites are representative of each ovarian tumor. The total fractional concentration of tumor-derived DNA in plasma is assumed to be 40%. The plasma sample is assumed to be sequenced to an average depth of 50 times per nucleotide position. According to this predicted distribution of occurrence in plasma, the mutations that are present in all tumor tissues can be differentiated from the mutations only present in ¼ tumor cells by their occurrence in plasma. For example, the occurrence of 6 times can be used as a cutoff. For the mutations present in all tumor cells, 92.3% of the mutations would be present in the plasma for at least 6 times. In contrast, for the mutations that are present in ¼ tumor cells, only 12.4% of mutations would be present in the plasma for at least 6 times.

FIG. 23 is a table 2300 demonstrating the specificity of embodiments for 16 healthy control subjects. Their plasma DNA samples were sequenced to a median coverage of 30 folds. Detection of the mutations that were present in the plasma of the above ovarian cancer patient was performed in the plasma samples of these healthy subjects. The mutations present in the tumor of the ovarian cancer patient were very infrequently detected in the sequencing data of the plasma of the healthy control subjects and none of the category of mutations had an apparent fractional concentration of >1%. These results show that this detection method is highly specific.

B. Method

Figure 24:
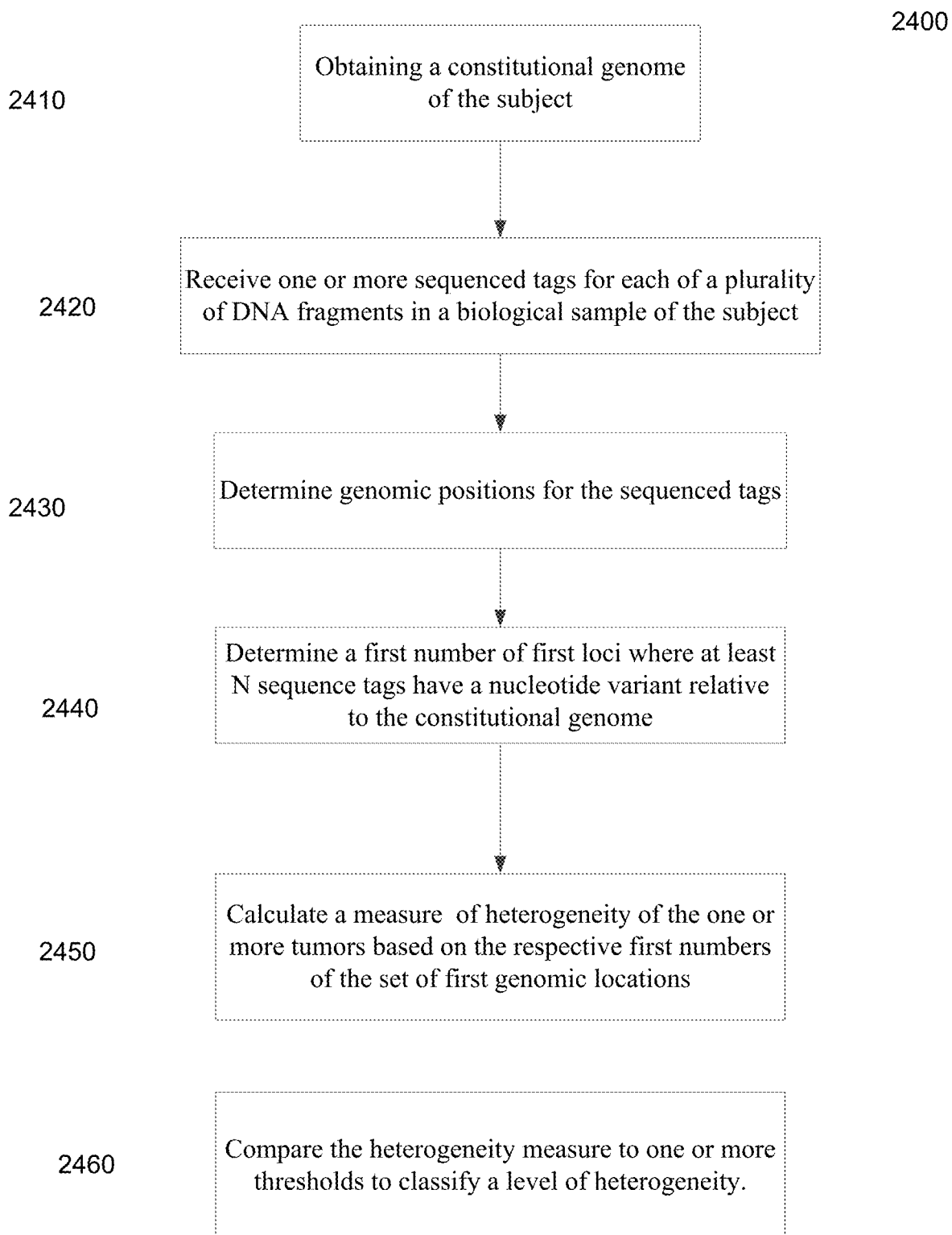
FIG. 24 is a flowchart of a method 2400 for analyzing a heterogeneity of one or more tumors of a subject according to embodiments of the present invention.

FIG. 24 is a flowchart of a method 2400 for analyzing a heterogeneity of one or more tumors of a subject according to embodiments of the present invention. Certain steps of method 2400 may be performed as described herein, At block 2410, a constitutional genome of the subject is obtained. At block 2420, one or more sequence tags are received for each of a plurality of DNA fragments in a biological sample of the subject, where the biological sample includes cell-free DNA. At block 2430, genomic positions are determined for the sequence tags. At block 2440, the sequence tags are compared to the constitutional genome to determine a first number of first loci. At each first loci, a number of the sequence tags having a sequence variant relative to the constitutional genome is above a cutoff value, where the cutoff value is greater than one.

At block 2450, a measure of heterogeneity of the one or more tumors are calculated based on the respective first numbers of the set of first genomic locations. In one aspect, the measures can provide a value that represents a number of mutations that are shared by tumors relative to a number of mutations that are not shared by tumors. Here, various tumors can exist as a single object, with different tumors within the object, which may represent what is normally called intra-tumor heterogeneity. The measure can also relate to whether some mutations are in one or a few tumors compared to mutations that are in many or most tumors. More than one measure of heterogeneity can be calculated.

At block 2460, the heterogeneity measure can be compared to a threshold value to determine a classification of a level of heterogeneity. The one or more measured can be used in various ways. For example, one or more heterogeneity measure measures can be used to predict the chance of tumor progression. In some tumors, the more heterogeneity the higher is the chance of progression and the higher is the chance of emergence of a resistant clone following treatment (e.g. targeted treatment).

C. Tumor Heterogeneity Measures

One example of a heterogeneity measure is number of 'concentration bands' of different groups of mutations in plasma. For example, if there are two predominant tumor clones within a patient, and if these clones are present in different concentrations, then we would expect to see two different mutations with different concentrations in plasma. These different values can be computed by determining the fractional concentration for different sets of mutations, where each set corresponds to one of the tumors.

Each of these concentrations can be called a 'concentration band' or 'concentration class'. If a patient has more clones, then more concentration bands/classes will be seen. Thus, the more bands, the more heterogeneous. The number of concentration bands can be seen by plotting the fractional concentrations for various mutations. A histogram can be made for the various concentrations, where different peaks correspond to different tumors (or different clones of one tumor). A large peak will likely be for mutations that are shared by all or some tumors (or clones of a tumor). These peaks may be analyzed to determine which smaller peaks are combined to determine a larger peak. A fitting procedure may be used, e.g., similar to the fitting procedure for FIGS. 10B and 11.

In one implementation, the histogram is a plot with Y-axis being the amount (e.g., number or proportion) of loci and x-axis being the fractional concentration. Mutations that are shared by all or some tumors would result in a higher fractional concentration. The peak size would represent the amount of loci that give rise to a particular fractional concentration. The relative size of the peaks at low and high concentration would reflect the degree of heterogeneity of the tumors (or clones of a tumor). A larger peak at the high concentration reflects that most mutations are shared by most or all tumors (or clones of a tumor) and indicate a lower degree of tumor heterogeneity. If the peak at the low concentration is larger, then most mutations are shared by a few tumors (or a few clones of a tumor). This would indicate a higher degree of tumor heterogeneity The more peaks that exist, the more site-specific mutations there are. Each peak can correspond to a different set of mutations, where the set of mutations are from a subset of the tumors (e.g., just one or two tumors—as illustrated above). For the example of FIG. 19, there might be a total of 7 peaks, with the 4 site-only peaks likely having the smallest concentration (depending on the relative size of the tumors), two peaks for AB sites and CD sites, and a peak for mutations shared by all sites.

The location of the peaks can also provide a relative size of the tumors. A larger concentration would correlate to a larger tumor, as a larger tumor would release more tumor DNA into the sample, e.g., into plasma. Thus, one could estimate the load of tumor cells carrying the different classes of mutations.

Another example of a heterogeneity measure is the proportion of mutation sites having relatively few variant reads (e.g., 4, 5, or 6) compared to the proportion of mutation reads having relatively high variant reads (e.g., 9-13). Referring back to FIG. 22, one can see that the sire-specific mutations had fewer variant reads (which also results in a smaller fractional concentration). The share mutations have more variant reads (which also results in a larger fractional concentration). A ratio of a first proportion at 6 (smaller count) divided by a second proportion at 10 (larger count) conveys a heterogeneity measure. If the ratio is small, then there are few mutations that are site-specific, and thus the level of heterogeneity is low. If the ratio is large (or at least larger than values calibrated from known specimens), then the level of heterogeneity is larger.

D. Determining Thresholds

The threshold values can be determined from subjects whose tumors are biopsied (e.g., as described above) to directly determine a level of heterogeneity. The level may be defined in various ways, such as ratios of site-specific mutations to shared mutations. Biological samples (e.g., plasma samples) can then be analyzed to determine heterogeneity measures, where a heterogeneity measure from the biological samples can be associated with the level of heterogeneity determined by analyzing the cells of the tumors directly.

Such a procedure can provide a calibration of thresholds relative to heterogeneity levels. If the test heterogeneity measure falls between two thresholds, then the level of heterogeneity can be estimated as being between the levels corresponding to the thresholds.

In one embodiment, a calibration curve can be calculated between the heterogeneity levels determined from the biopsies and the corresponding heterogeneity measure determined from the plasma sample (or other sample). In such an example, the heterogeneity levels are numeric, where these numeric levels can correspond to different classifications. Different ranges of numeric levels can correspond to different diagnoses, e.g., different stages of cancer.

E. Method Using Fractional Concentration from Genomic Representation

Tumor heterogeneity can also be analyzed using the fractional concentration, e.g., as determined using embodiments of method 1200. The genomic regions that exhibit one copy loss might come from different tumors. Thus, the fractional concentration determined for various genomic regions might differ depending on whether the amplification (or deletion for 1-copy loss) exists in just one tumor or multiple tumors. Thus, the same heterogeneity measures may be used for fractional concentrations determined via embodiments of method 1200.

For example, one genomic region can be identified as corresponding to a 1-copy loss, and a fractional concentration can be determined just from a respective density at that genomic region (the respective density could be used as a fractional concentration). A histogram can be determined from the various respective densities by counting the number of regions having various densities. If only one tumor or one tumor clone or one tumor deposit had a gain in a particular region, then the density of that region would be less than the density in a region that had a gain in multiple tumors or multiple tumor clones or multiple tumor deposits (i.e., the fractional concentration of tumor DNA in the shared region would be larger than the site-specific region). The heterogeneity measures described above can thus be applied to peaks identified using the copy number gain or loss in various regions, just as the fractional concentration of different sites showed a distribution of fractional concentrations.

In one implementation, if the respective densities are used for the histogram, one would have gains and losses separated. The regions showing a gain could be analyzed separately by creating a histogram just for gains, and a separate histogram can be created just for losses. If the fractional concentration is used, then the peaks of losses and gains can be analyzed together. For example, the fractional concentrations use a difference (e.g., as an absolute value) to the reference density, and thus the fractional concentrations for gains and losses can contribute to the same peak.

XIII. COMPUTER SYSTEM

Figure 25:
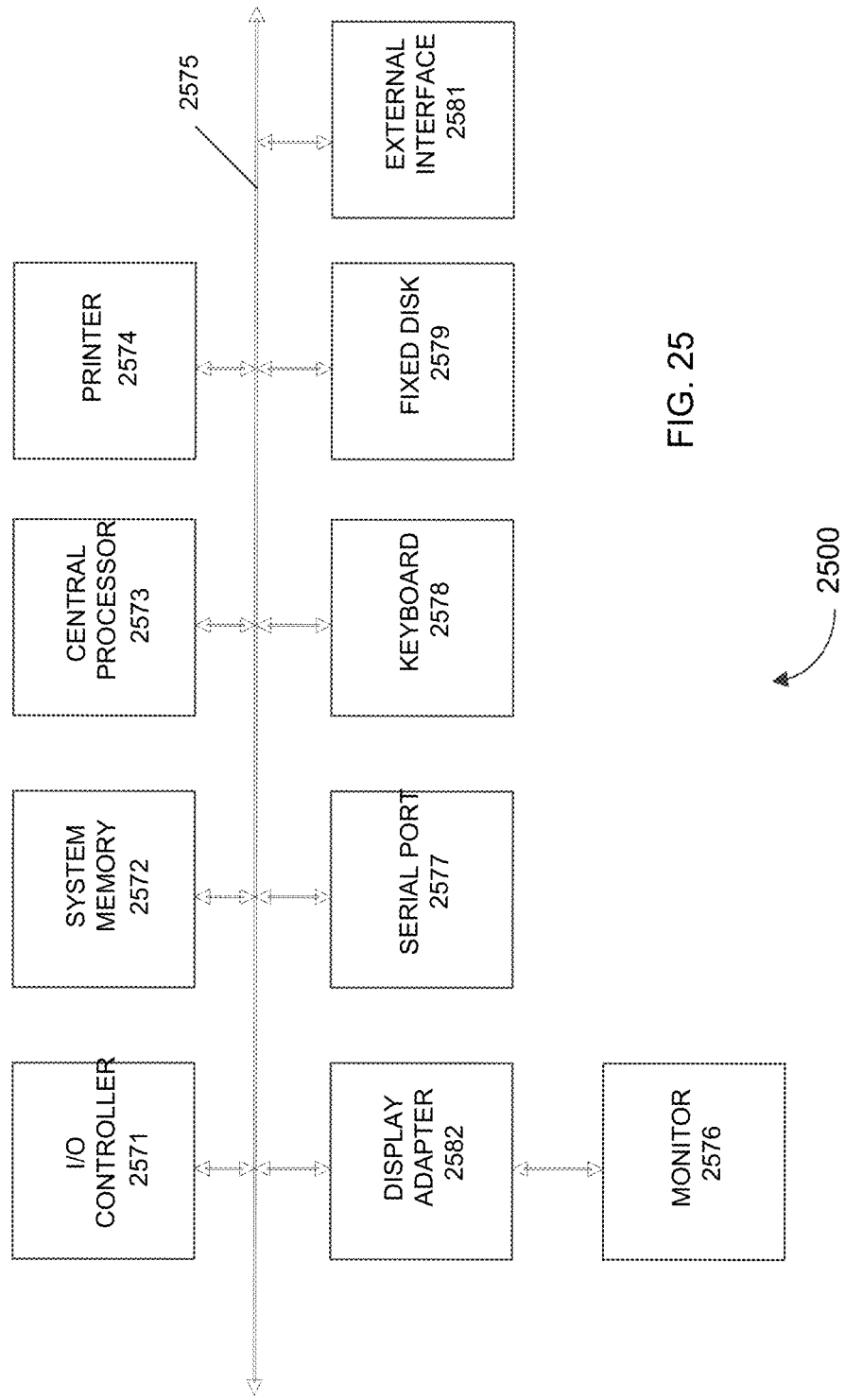
FIG. 25 shows a block diagram of an example computer system 2500 usable with system and methods according to embodiments of the present invention.

Any of the computer systems mentioned herein may utilize any suitable number of subsystems. Examples of such subsystems are shown in FIG. 25 in computer apparatus 2500. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 25 are interconnected via a system bus 2575. Additional subsystems such as a printer 2574, keyboard 2578, fixed disk 2579, monitor 2576, which is coupled to display adapter 2582, and others are shown. Peripherals and input/output (I/O) devices, which couple to I/O controller 2571, can be connected to the computer system by any number of means known in the art, such as serial port 2577. For example, serial port 2577 or external interface 2581 (e.g. Ethernet, Wi-Fi, etc.) can be used to connect computer system 2500 to a wide area network such as the Internet, a mouse input device, or a scanner. The interconnection via system bus 2575 allows the central processor 2573 to communicate with each subsystem and to control the execution of instructions from system memory 2572 or the fixed disk 2579, as well as the exchange of information between subsystems. The system memory 2572 and/or the fixed disk 2579 may embody a computer readable medium. Any of the values mentioned herein can be output from one component to another component and can be output to the user.

A computer system can include a plurality of the same components or subsystems, e.g., connected together by external interface 2581 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. As used herein, a processor includes a multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer program product (e.g. a hard drive, a CD, or an entire computer system), and may be present on or within different computer program products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

A recitation of "a", "an" or "the" is intended to mean "one or more" unless specifically indicated to the contrary.

All patents, patent applications, publications, and descriptions mentioned here are incorporated by reference in their entirety for all purposes. None is admitted to be prior art.

What is claimed is:

1. A method of measuring a fractional concentration of tumor DNA in a biological sample including cell-free DNA, the method comprising:
   (a) sequencing a plurality of DNA fragments from the biological sample to obtain one or more sequence tags for each of the plurality of DNA fragments, thereby obtaining at least 15,000 sequence tags, without having previously determined a tumor-specific marker from tumor cells of a subject from whom the biological sample was obtained, wherein the plurality of DNA fragments include at least 15,000 DNA fragments;
   (b) receiving, at a computer system, the one or more sequence tags for each of the plurality of DNA fragments in the biological sample, wherein a portion of the plurality of DNA fragments is tumor DNA;
   (c) determining, by the computer system, genomic positions for the at least 15,000 sequence tags in a human reference genome;
   (d) counting, by the computer system, a total number of the at least 15,000 sequence tags;
   (e) for each genomic region of a plurality of genomic regions:
      (1) determining which of the at least 15,000 sequence tags have a genomic position within the genomic region;
      (2) counting, by the computer system, a respective amount of the at least 15,000 DNA fragments within the genomic region from the sequence tags having the genomic position within the genomic region;
      (3) normalizing, by the computer system, the respective amount to obtain a respective density of sequence tags in the genomic region using the total number of the sequence tags;
      (4) comparing, by the computer system, the respective density to a reference density of sequence tags, representing a genomic region that does not exhibit a copy number aberration; and
      (5) identifying, based on the comparing, whether the genomic region exhibits a 1-copy loss or a 1-copy gain based on the respective density differing from the reference density by a statistically significant amount;
   (f) calculating, by the computer system, a first density from one or more respective densities identified as exhibiting a 1-copy loss or from one or more respective densities identified as exhibiting a 1-copy gain;
   (g) calculating, by the computer system, the fractional concentration of tumor DNA in the biological sample by:
      (1) determining a difference between the first density and another density to obtain a differential, wherein the differential is normalized with the reference density, wherein the another density is determined from one or more respective densities identified as exhibiting an opposite copy number aberration or no copy number aberration; and
   (h) outputting, by the computer system, the fractional concentration of tumor DNA in the biological sample.

2. The method of claim 1, further comprising:
   creating a histogram of a number of genomic regions having various respective densities;
   identifying a plurality of peaks in the histogram; and
   calculating a heterogeneity measure from a ratio of a number of genomic regions of one or more first peaks to a number of genomic regions of one or more second peaks.

3. The method of claim 2, wherein the histogram uses values of fractional concentrations determined separately for each genomic region in creating the histogram.

4. The method of claim 2, wherein the one or more first peaks have respective densities of a first specified amount, and the one or more second peaks have respective densities of a second specified amount.

5. The method of claim 4, wherein the first specified amount is a first range and the second specified amount is a second range, and wherein the first range is less than the second range.

6. The method of claim 1, wherein comparing the respective density to the reference density to identify whether the genomic region exhibits a 1-copy loss or a 1-copy gain includes:
computing a difference between the respective density and the reference density; and
comparing the difference to a cutoff value.

7. The method of claim 1, wherein the differential is normalized with the reference density by:
dividing the differential by the reference density.

8. The method of claim 1, wherein the another density is the reference density.

9. The method of claim 8, wherein calculating the fractional concentration further includes multiplying the differential by two.

10. The method of claim 1, wherein the first density is calculated using respective densities identified as exhibiting a 1-copy gain, and wherein the another density is a second density calculated from respective densities identified as exhibiting a 1-copy loss.

11. The method of claim 10, wherein the differential is normalized with the reference density by:
computing a first ratio of the first density and the reference density; and
computing a second ratio of the second density and the reference density, wherein the differential is between the first ratio and the second ratio.

12. The method of claim 1, wherein comparing the respective density to the reference density to identify whether the genomic region exhibits a 1-copy loss or a 1-copy gain includes:
fitting peaks to a distribution curve of a histogram of the respective densities, wherein the first density corresponds to a first peak and the another density corresponds to a second peak.

13. The method of claim 1, wherein all genomic regions determined to exhibit a statistically significant gain in the respective density relative to the reference density are identified as exhibiting a 1-copy gain.

14. The method of claim 1, wherein determining the genomic position for a sequence tag includes:
aligning at least a portion of the sequence tags to the human reference genome.

15. The method of claim 14, wherein the alignment of the sequence tag allows for one or more mismatches between the sequence tag and the human reference genome.

16. The method of claim 14, wherein normalizing the respective amount to obtain the respective density of a first genomic region of the plurality of genomic regions includes using a same total number of aligned sequence tags to determine the respective density and the reference density, the same total number of aligned sequence tags corresponding to the number of the sequence tags.

17. The method of claim 14, wherein normalizing the respective amount to obtain the respective density of a first genomic region of the plurality of genomic regions includes dividing the respective amount by a total number of aligned sequence tags, the total number of aligned sequence tags corresponding to the number of the sequence tags.

18. The method of claim 1, wherein the plurality of genomic regions each have a same length.

19. The method of claim 1, wherein the plurality of genomic regions are non-overlapping.

20. The method of claim 1, further comprising:
obtaining a blood sample from the subject; and
extracting the cell-free DNA from the blood sample, wherein the biological sample is plasma or serum.

21. The method of claim 1, wherein the biological sample is from a subject who has hepatocellular carcinoma (HCC).

22. The method of claim 1, further comprising:
providing treatment to the subject after measuring the fractional concentration of tumor DNA in the biological sample of the subject; and
repeating the method of claim 1 for a new sample obtained from the subject after treatment to measure a new fractional concentration of tumor DNA in the new sample.

23. The method of claim 1, wherein the first density is determined using a statistical analysis of a distribution of the respective densities identified as exhibiting a 1-copy loss or of the respective densities identified as exhibiting a 1-copy gain.

24. The method of claim 1, wherein the plurality of genomic regions include at least 400 genomic regions.

25. The method of claim 1, wherein at least one of the plurality of genomic regions includes at least 500 kilobases.

26. The method of claim 1, further comprising:
responsive to the outputting of the fractional concentration of tumor DNA, providing treatment to the subject.

27. The method of claim 1, further comprising:
providing treatment to the subject after measuring the fractional concentration of tumor DNA in the biological sample of the subject, wherein the treatment includes surgery.

28. A computer product comprising a non-transitory computer readable medium storing a plurality of instructions that when executed control a measurement and computing system to measure a fractional concentration of tumor DNA in a biological sample including cell-free DNA, the instructions comprising:
sequencing, by a sequencing machine of the system, a plurality of DNA fragments from the biological sample to obtain one or more sequence tags for each of the plurality of DNA fragments, thereby obtaining at least 15,000 sequence tags, without having previously determined a tumor-specific marker from tumor cells of a subject from whom the biological sample was obtained, wherein the plurality of DNA fragments include at least 15,000 DNA fragments;
receiving, at a processor of the system, one or more sequence tags for each of the plurality of DNA fragments in the biological sample, wherein a portion of the plurality of DNA fragments is tumor DNA;
determining, by the processor of the system, genomic positions for the at least 15,000 sequence tags in a human reference genome;
counting, by the processor of the system, a total number of the at least 15,000 sequence tags;
for each genomic region of a plurality of genomic regions:
determining, by the processor of the system, which of the at least 15,000 sequence tags have a genomic position within the genomic region;

counting, by the processor of the system, a respective amount of the at least 15,000 DNA fragments within the genomic region from the sequence tags having the genomic position within the genomic region;

normalizing, by the processor of the system, the respective amount to obtain a respective density of sequence tags in the genomic region using the total number of the sequence tags;

comparing, by the processor of the system, the respective density to a reference density of sequence tags, representing a genomic region that does not exhibit a copy number aberration; and identifying, by the processor of the system based on the comparing, whether the genomic region exhibits a 1-copy loss or a 1-copy gain based on the respective density differing from the reference density by a statistically significant amount;

calculating, by the processor of the system, a first density from one or more respective densities identified as exhibiting a 1-copy loss or from one or more respective densities identified as exhibiting a 1-copy gain, wherein the first density is determined using a statistical analysis of a distribution of the respective densities identified as exhibiting a 1-copy loss or of the respective densities identified as exhibiting a 1-copy gain; and calculating, by the processor of the system, the fractional concentration of tumor DNA in the biological sample by:
determining a difference between the first density and another density to obtain a differential, wherein the differential is normalized with the reference density, wherein the another density is determined from one or more respective densities identified as exhibiting an opposite copy number aberration or no copy number aberration.

29. The computer product of claim 28, wherein the instructions further comprise:
creating a histogram of a number of genomic regions having various respective densities;
identifying a plurality of peaks in the histogram; and
calculating a heterogeneity measure from a ratio of a number of genomic regions of one or more first peaks to a number of genomic regions of one or more second peaks.

30. The computer product of claim 29, wherein the histogram uses values of fractional concentrations determined separately for each genomic region in creating the histogram.

31. The computer product of claim 29, wherein the one or more first peaks have respective densities of a first specified amount, and the one or more second peaks have respective densities of a second specified amount.

32. The computer product of claim 31, wherein the first specified amount is a first range and the second specified amount is a second range, and wherein the first range is less than the second range.

33. The computer product of claim 28, wherein comparing the respective density to the reference density to identify whether the genomic region exhibits a 1-copy loss or a 1-copy gain includes:

computing a difference between the respective density and the reference density; and
comparing the difference to a cutoff value.

34. The computer product of claim 28, wherein the differential is normalized with the reference density by:
dividing the differential by the reference density.

35. The computer product of claim 28, wherein the another density is the reference density.

36. The computer product of claim 35, wherein calculating the fractional concentration further includes multiplying the differential by two.

37. The computer product of claim 28, wherein the first density is calculated using respective densities identified as exhibiting a 1-copy gain, and wherein the another density is a second density calculated from respective densities identified as exhibiting a 1-copy loss.

38. The computer product of claim 37, wherein the differential is normalized with the reference density by:
computing a first ratio of the first density and the reference density; and
computing a second ratio of the second density and the reference density, wherein the differential is between the first ratio and the second ratio.

39. The computer product of claim 28, wherein comparing the respective density to the reference density to identify whether the genomic region exhibits a 1-copy loss or a 1-copy gain includes:
fitting peaks to a distribution curve of a histogram of the respective densities, wherein the first density corresponds to a first peak and the another density corresponds to a second peak.

40. The computer product of claim 28, wherein all genomic regions determined to exhibit a statistically significant gain in the respective density relative to the reference density are identified as exhibiting a 1-copy gain.

41. The computer product of claim 28, wherein determining the genomic position for a sequence tag includes:
aligning at least a portion of the sequence tags to the human reference genome.

42. The computer product of claim 41, wherein the alignment of the sequence tag allows for one or more mismatches between the sequence tag and the human reference genome.

43. The computer product of claim 41, wherein normalizing the respective amount to obtain the respective density of a first genomic region of the plurality of genomic regions includes using a same total number of aligned sequence tags to determine the respective density and the reference density, the same total number of aligned sequence tags corresponding to the number of the sequence tags.

44. The computer product of claim 41, wherein normalizing the respective amount to obtain the respective density of a first genomic region of the plurality of genomic regions includes dividing the respective amount by a total number of aligned sequence tags, the total number of aligned sequence tags corresponding to the number of the sequence tags.

45. The computer product of claim 28, wherein the plurality of genomic regions each have a same length.

46. The computer product of claim 28, wherein the plurality of genomic regions are non-overlapping.

* * * * *